US009883991B2

(12) United States Patent
Behler et al.

(10) Patent No.: US 9,883,991 B2
(45) Date of Patent: Feb. 6, 2018

(54) ALKYL SULFOSUCCINATE MIXTURES, AND USE THEREOF

(75) Inventors: Ansgar Behler, Bottrop (DE); Rainer Eskuchen, Langenfeld (DE); Almud Folge, Solingen (DE); Helga Gondek, Dusseldorf (DE); Catherine Weichold, Aachen (DE)

(73) Assignee: Cognis IP Management GmbH, Düsseldorf (DE)

( * ) Notice: Subject to any disclaimer, the term of this patent is extended or adjusted under 35 U.S.C. 154(b) by 66 days.

(21) Appl. No.: 13/124,998

(22) PCT Filed: Oct. 15, 2009

(86) PCT No.: PCT/EP2009/007382
§ 371 (c)(1),
(2), (4) Date: Apr. 19, 2011

(87) PCT Pub. No.: WO2010/046048
PCT Pub. Date: Apr. 29, 2010

(65) Prior Publication Data
US 2012/0128601 A1    May 24, 2012

(30) Foreign Application Priority Data

Oct. 24, 2008 (EP) .................................... 08018623
Aug. 5, 2009 (EP) .................................... 09010116
Sep. 4, 2009 (EP) .................................... 09011350

(51) Int. Cl.
| | | |
|---|---|---|
| A61K 8/00 | (2006.01) |
| A61K 8/06 | (2006.01) |
| A61K 8/46 | (2006.01) |
| A61Q 1/02 | (2006.01) |
| A61Q 1/06 | (2006.01) |
| A61Q 5/06 | (2006.01) |
| A61Q 5/10 | (2006.01) |

(Continued)

(52) U.S. Cl.
CPC ............... *A61K 8/06* (2013.01); *A61K 8/062* (2013.01); *A61K 8/064* (2013.01); *A61K 8/466* (2013.01); *A61Q 1/02* (2013.01); *A61Q 1/06* (2013.01); *A61Q 5/065* (2013.01); *A61Q 5/10* (2013.01); *A61Q 17/04* (2013.01); *A61Q 19/00* (2013.01); *C07C 309/17* (2013.01); *A61K 2800/596* (2013.01); *A61Q 15/00* (2013.01); *A61Q 19/08* (2013.01)

(58) Field of Classification Search
CPC .......... A61K 8/06; A61K 8/062; A61K 8/064; A61K 8/466; A61K 2800/596; A61Q 1/02; A61Q 5/065; A61Q 5/10; A61Q 17/04; A61Q 19/00; A61Q 19/08; A61Q 1/06; C07C 309/17
See application file for complete search history.

(56) References Cited

U.S. PATENT DOCUMENTS 2,176,423 A    10/1939 Jaeger
4,039,562 A    8/1977 Bloch et al.
(Continued)

FOREIGN PATENT DOCUMENTS

DE    868154 C    2/1953
DE    2507520    9/1976
(Continued)

OTHER PUBLICATIONS

International Search Report in PCT/EP2009/007382, dated Mar. 31, 2010, 3 pgs.
Comission Directive 2005/9/EC of Jan. 28, 2005 amending Council Directive 76/768/EEC.
Finkel, P. "Formulierung Kosmetischer Sonnenschutzmittel", SOFW-Journal 122, Aug. 1996, p. 543-548.
(Continued)

*Primary Examiner* — Robert Cabral
(74) *Attorney, Agent, or Firm* — Marshall, Gerstein & Borun LLP

(57) ABSTRACT

The invention relates to mixtures of alkyl sulfosuccinate monoesters of general formulas (I) and/or (II), in which R represents a linear or branched, saturated or unsaturated alkyl group having 6 to 22 C atoms, and X and Y independently represent a hydrogen atom or a cation that can form a water-soluble salt and is selected from among the group composed of alkali metal, alkaline earth metal, ammonia, and organic ammonia. The invention is characterized in that the mixture contains 30 to 70 percent by weight of C16 alkyl sulfosuccinate monoester and 30 to 70 percent by weight of C18 alkyl sulfosuccinate monoester, the percentages by weight being in relation to the total amount of alkyl sulfosuccinate monoesters of formulas (I) and (II). The invention also relates to the use of said mixtures in cosmetic and/or pharmaceutical preparations.

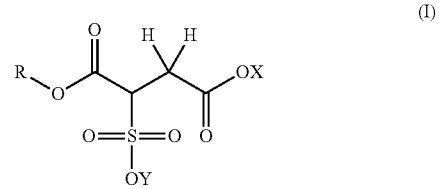

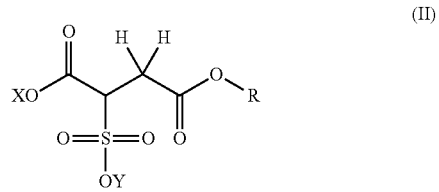

11 Claims, No Drawings

(51) Int. Cl.
*A61Q 17/04* (2006.01)
*A61Q 19/00* (2006.01)
*C07C 309/17* (2006.01)
*A61Q 19/08* (2006.01)
*A61Q 15/00* (2006.01)

(56) References Cited

U.S. PATENT DOCUMENTS

| | | | |
|---|---|---|---|
| 5,705,169 | A | 1/1998 | Stein et al. |
| 5,730,960 | A | 3/1998 | Stein et al. |
| 5,840,943 | A | 11/1998 | Ansmann et al. |
| 6,193,960 | B1 | 2/2001 | Metzger et al. |
| 2005/0136026 | A1* | 6/2005 | Qiu et al. ............ 424/70.24 |

FOREIGN PATENT DOCUMENTS

| | | |
|---|---|---|
| DE | 2507520 A1 | 9/1976 |
| DE | 4325923 | 2/1995 |
| DE | 4325923 A1 | 2/1995 |
| DE | 19712033 | 9/1998 |
| DE | 19712033 A1 | 9/1998 |
| EP | 0766661 A1 | 12/1995 |
| EP | 0693471 | 1/1996 |
| EP | 0693471 A1 | 1/1996 |
| EP | 0694521 A1 | 1/1996 |
| EP | 0766661 | 4/1997 |
| EP | 0694521 | 1/1998 |
| EP | 0818450 | 1/1998 |
| EP | 0818450 A1 | 1/1998 |
| EP | 1371359 | 12/2003 |
| EP | 1371359 A2 | 12/2003 |
| GB | 636462 A * | 5/1950 |
| WO | WO-95/34528 | 12/1995 |
| WO | WO-2007/048757 | 5/2007 |
| WO | WO-2007/048757 A1 | 5/2007 |

OTHER PUBLICATIONS

Finkel, P.,"Formulierung Kosmetischer Sonnenschutzmittel", Parf. Kosm., vol. 80, No. Mar. 1999, p. 10-16.
Griffin, W.C., J. Soc. Cosmet. Chem. 1 (1949) 311.
Griffin, W.C., J. Soc. Cosmet. Chem. 5 (1954) 249.
Kirk-Othmer, Encyclopedia of Chemical Technology, $3^{rd}$ edition, 1979, vol. 8, 5 pages.
Zviak, Charles, The Science of Hair Care, Ch 7. p. 248-250, Ch. 8 p. 264-267, New York (1986).
European Commission, European Inventory of cosmetic ingredients, 1996 [Hnhd-01938 (203-058-I)].
Comission Directive 2007/22/EC of Apr. 17, 2007 amending Council Directive 76/768/EEC.
Commission Directive 2007/22/EC of Apr. 17, 2007 amending Council Directive 76/768/EEC.
Commission Directive 2005/9/EC of Jan. 28, 2005 amending Council Directive 76/768/EEC.
DIN 55944: 1990-04.
DIN 55944: 2003-11.
"International Search Report in PCT/EP2009/007382", dated Mar. 31, 2010, 3 pgs.
Translation of DE-4325923, 5 pgs.
Translation of DE-868154, 2 pgs.
Finkel, P. "Formulierung Kosmetischer Sonnenschutzmittel" *SOFW—Journal 122* 1996 , pp. 543-548.
Finkel, P. , "Formulierung Kosmetischer Sonnenschutzmittel", *Parf. Kosm.*, vol. 80, No. 3 1999 , pp. 10-16.
Griffin, W.C., *J. Soc. Cosmet. Chem. 5* 1954 , p. 249.
Griffin, W.C., *J. Soc. Cosmet. Chem. 1* 1949 , p. 311.
Kirk-Othermer, *Encyclopedia of Chemical Technology, 3rd Edition*, vol. 8 1979 , 5 pgs.
Zviak, Charles, "The Science of Hair Care", Ch. 7 & 8 1986 , pp. 248-250 & 264-267.
Examination Report, Indian patent application No. 2710/CHENP/2011, dated Apr. 26, 2017.

* cited by examiner

ALKYL SULFOSUCCINATE MIXTURES, AND USE THEREOF

The present invention relates to mixtures of alkyl sulfosuccinates and to the use thereof in cosmetic and/or pharmaceutical formulations.

STATE OF THE ART

In cosmetic and pharmaceutical formulations, a multitude of substances have to be present in stable and homogeneous form. For example, the stable and simple emulsification of oil and water in different emulsion types is a constant task. In addition, a multitude of (active) ingredients, some of which are in solid form, must also be homogeneously dispersed or stabilized in the formulations, in order to ensure, inter alia, homogeneous distribution of the active ingredient in the cosmetic and/or pharmaceutical carrier. The same applies to liquid (active) ingredients. In spite of the multitude of compounds already available on the market, there is a constant interest in providing novel compounds which solve this problem. In the case of known products (for example emulsifiers, dispersants or stabilizers), in particular electrolyte compatibility, pigment compatibility and alkali stability are in need of improvement. It is additionally of interest that the products can be formulated as a powder via a spray-drying operation, since this makes both the handling of the products and the processability much easier. It is additionally of interest to provide products which make it possible to obtain cosmetic and/or pharmaceutical formulations which are stable even at low pH. Especially in the case of formulations in emulsion form, storage stability is additionally of interest: mention should be made of: phase stability (no phase separation), a stable particle size and stable viscosity.

It was an object of the present invention to provide novel products which are suitable as ingredients, especially as interface-active substances, for example as emulsifiers and/or dispersants, in cosmetic and/or pharmaceutical formulations. In this context, in particular, high electrolyte compatibility, good pigment compatibility and high alkali stability were of interest. In addition, the products were to be producible in a simple manner as powders. It was additionally of interest that the cosmetic and/or pharmaceutical formulations obtainable with the products are stable over a wide pH range. It was additionally of interest that the formulations have a high storage stability; in this context, the avoidance of phase separation and/or a stable particle size of the emulsions, and the stability of the viscosity, were of interest.

It has been found that, surprisingly, the inventive mixtures of the alkyl sulfosuccinates achieve these objects.

DESCRIPTION OF THE INVENTION

Mixtures of Alkyl Sulfosuccinate Monoesters

The term "alkyl sulfosuccinate" is used in the context of the present invention synonymously with the term alkyl sulfosuccinate monoester, and refers to all compounds of the general formula (I) and/or (II)

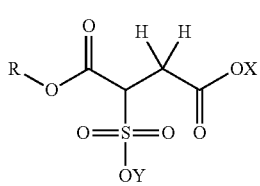
(I)

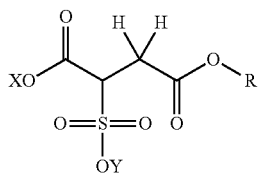
(II)

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium.

The invention provides mixtures of alkyl sulfosuccinate monoesters of the general formula (I) and/or (II)

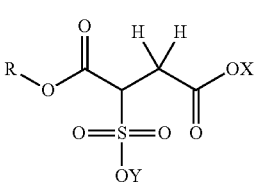
(I)

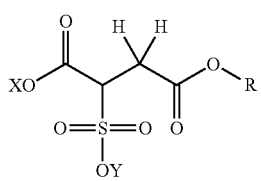
(II)

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises
- 30 to 70% by weight of C16-alkyl sulfosuccinate monoester and
- 30 to 70% by weight of C18-alkyl sulfosuccinate monoester, where the percentages by weight are based on the alkyl sulfosuccinate monoesters of the formulae (I) and (II).

These inventive mixtures may comprise the alkyl sulfosuccinate monoesters of the formulae (I) and (II) in any desired proportions. The inventive mixtures may comprise, for example, 0 to 90%, 0 to 80%, 0 to 70%, 0 to 60%, 0 to 50%, 0 to 40%, 0 to 30%, 0 to 20%, or 0 to 10% of the alkyl sulfosuccinate monoesters of the general formula (I). The inventive mixtures may comprise, for example, 10 to 100%, 20 to 100%, 30 to 100%, 40 to 100%, 50 to 100%, 60 to 100%, 70 to 100%, 80 to 100% or 90 to 100% of the alkyl sulfosuccinate monoesters of the general formula (I). The inventive mixtures may comprise, for example, 0 to 90%, 0 to 80%, 0 to 70%, 0 to 60%, 0 to 50%, 0 to 40%, 0 to 30%, 0 to 20%, or 0 to 10% of the alkyl sulfosuccinate monoesters of the general formula (II). The inventive mixtures may comprise, for example, 10 to 100%, 20 to 100%, 30 to 100%, 40 to 100%, 50 to 100%, 60 to 100%, 70 to 100%, 80 to 100% or 90 to 100% of the alkyl sulfosuccinate monoesters of the general formula (II).

These inventive mixtures may comprise the alkyl sulfosuccinate monoesters of the formulae (I) and (II) in any desired proportions. In a preferred embodiment of the invention, the inventive mixtures comprise the alkyl sulfosuccinate monoesters of the formula (I) and the alkyl sulfosuccinate monoesters of the formula (II) in a weight ratio of [10-1]:1, especially [8-1]:1, preferably [6-1.5]:1, especially [4-2]:1, more preferably [3.5-2.5]:1. In one embodiment of the invention, the mixtures comprise the alkyl sulfosuccinates of the formula (I) and the alkyl sulfosuccinates of the formula (II) in a weight ratio of 3:1.

These inventive mixtures may comprise the alkyl sulfosuccinate monoesters of the formulae (I) and (II) in any desired proportions. In a further embodiment of the invention, the inventive mixtures comprise the alkyl sulfosuccinate monoesters of the formula (II) and the alkyl sulfosuccinate monoesters of the formula (I) in a weight ratio of [10-1]:1, especially [8-1]:1, preferably [6-1.5]:1, especially [4-2]:1, more preferably [3.5-2.5]:1.

Accordingly, the present invention comprises, as one embodiment, mixtures of alkyl sulfosuccinate monoesters of the general formula (I)

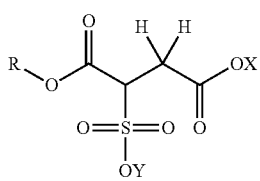

(I)

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and 30 to 70% by weight of C18-alkyl sulfosuccinate monoester, where the percentages by weight are based on the total amount of the alkyl sulfosuccinate monoesters of the formula (I).

Accordingly, the present invention comprises, as one embodiment, mixtures of alkyl sulfosuccinate monoesters of the general formula (II)

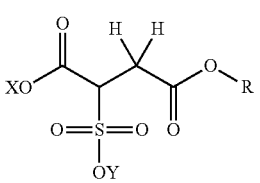

(II)

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and 30 to 70% by weight of C18-alkyl sulfosuccinate monoester, where the percentages by weight are based on the total amount of the alkyl sulfosuccinate monoesters of the formula (II).

In a preferred embodiment of the invention, X and Y are each independently selected from the group consisting of Na, K, Mg, Ca and $NH_4$. Particular preference is given to mixtures in which X and Y are identical; X and Y are preferably each Na.

R is a linear or branched, saturated or unsaturated alkyl radical having 6 to 22 and preferably 8 to 18 carbon atoms. Examples include n-octyl, i-octyl, n-nonyl, i-nonyl, n-decyl, i-decyl, n-undecyl, i-undecyl, n-dodecyl (trivial name lauryl), i-dodecyl, n-tridecyl, i-tridecyl, n-tetradecyl, i-tetradecyl, n-pentadecyl, i-pentadecyl, n-hexadecyl (trivial name cetyl), i-hexadecyl, n-heptadecyl, i-heptadecyl, n-octadecyl (trivial name stearyl), i-octadecyl and n-octadecenyl (oleyl).

In a preferred embodiment of the invention, the inventive mixture comprises less than 15, especially less than 10 and preferably less than 5% by weight of alkyl sulfosuccinate monoesters of the general formulae (I) and (II), in which R is a branched alkyl radical, based on the total amount of the alkyl sulfosuccinate monoesters.

In a preferred embodiment of the invention, the inventive mixture comprises less than 15, especially less than 10 and preferably less than 5% by weight of alkyl sulfosuccinate monoesters of the general formulae (I) and (II), in which R is an unsaturated alkyl radical, based on the total amount of the alkyl sulfosuccinate monoesters.

The inventive mixture comprises 30 to 70 and preferably 40 to 60% by weight, especially 45 to 55% by weight, of C16-alkyl sulfosuccinate monoester. The term "C16-alkyl sulfosuccinate monoester" refers to compounds of the general formula (I) and/or (II) in which R is an alkyl radical having 16 carbon atoms. The mixture preferably comprises compounds of the general formula (I) and/or (II) in which R is a linear and saturated alkyl radical having 16 carbon atoms (=hexadecyl radical, trivial name cetyl radical).

The inventive mixture comprises 30 to 70 and preferably 40 to 60% by weight, especially 45 to 55% by weight, of C18-alkyl sulfosuccinate monoester. The term "C18-alkyl sulfosuccinate monoester" refers to compounds of the general formula (I) and/or (II) in which R is an alkyl radical having 18 carbon atoms. The mixture preferably comprises compounds of the general formula (I) and/or (II) in which R is a linear and saturated alkyl radical having 18 carbon atoms (=Octadecyl radical, trivial name stearyl radical).

The percentages by weight of the C16-alkyl sulfosuccinate monoesters and of the C18-alkyl sulfosuccinate monoesters are based on the total amount of the alkyl sulfosuccinate monoesters of the general formulae (I) and (II) present in the mixture.

As a result of the preparation, the inventive alkyl sulfosuccinate mixtures may comprise up to 30% by weight of secondary ingredients. These are, for example, unconverted reactants from the esterification reaction (such as fatty alcohols or maleic anhydride) or by-products which form in the preparation, for example diesters. The term "mixtures of alkyl sulfosuccinate monoesters" thus includes mixtures which comprise at least 70% by weight of alkyl sulfosuccinate monoesters of the general formulae (I) and (II), and 0 to 30% by weight of secondary constituents.

In a preferred embodiment of the invention, the content of fatty alcohols is less than or equal to 10% by weight, preferably less than or equal to 5% by weight, based on the total amount of alkyl sulfosuccinate monoesters in the mixture.

Fatty alcohols in the context of the invention are understood to mean linear, saturated or unsaturated, primary alcohols (alkan-1-ols) having 6 to 22 carbon atoms.

It has been found that, surprisingly, mixtures of alkyl sulfosuccinate monoesters with a content of fatty alcohols of less than or equal to 10% by weight—based on the alkyl sulfosuccinate monoesters—can be spray-dried particularly efficiently, and it is thus possible in a technically simple manner to obtain powders.

The invention further provides mixtures of alkyl sulfosuccinate monoesters of the general formulae (I) and/or (II)

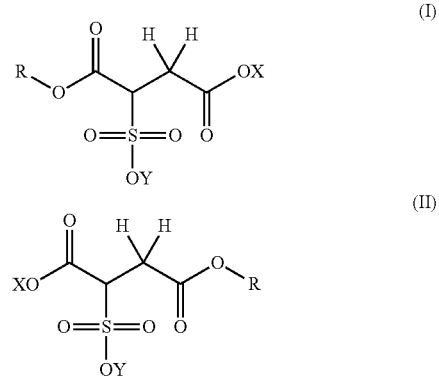

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and 30 to 70% by weight of C18-alkyl sulfosuccinate monoester, where the percentages by weight are based on the total amount of the C16- and C18-alkyl sulfosuccinate monoesters present in the mixture of the formulae (I) and (II);

and where the mixture comprises at least 50% by weight of C16- and C18-alkyl sulfosuccinate monoesters based on the sum of the alkyl sulfosuccinate monoesters of the formulae (I) and (II).

In a preferred embodiment of the invention, this mixture comprises at least 60% by weight, preferably at least 70% by weight, especially at least 80% by weight, of C16- and C18-alkyl sulfosuccinate monoesters, based on the sum of the alkyl sulfosuccinate monoesters of the formulae (I) and (II).

These inventive mixtures may comprise the alkyl sulfosuccinate monoesters of the formulae (I) and (II) in any desired proportions. The inventive mixtures may comprise, for example, 0 to 90%, 0 to 80%, 0 to 70%, 0 to 60%, 0 to 50%, 0 to 40%, 0 to 30%, 0 to 20%, or 0 to 10% of the alkyl sulfosuccinate monoesters of the general formula (I). The inventive mixtures may comprise, for example, 10 to 100%, 20 to 100%, 30 to 100%, 40 to 100%, 50 to 100%, 60 to 100%, 70 to 100%, 80 to 100% or 90 to 100% of the alkyl sulfosuccinate monoesters of the general formula (I). The inventive mixtures may comprise, for example, 0 to 90%, 0 to 80%, 0 to 70%, 0 to 60%, 0 to 50%, 0 to 40%, 0 to 30%, 0 to 20%, or 0 to 10% of the alkyl sulfosuccinate monoesters of the general formula (II). The inventive mixtures may comprise, for example, 10 to 100%, 20 to 100%, 30 to 100%, 40 to 100%, 50 to 100%, 60 to 100%, 70 to 100%, 80 to 100% or 90 to 100% of the alkyl sulfosuccinate monoesters of the general formula (II).

These inventive mixtures may comprise the alkyl sulfosuccinate monoesters of the formulae (I) and (II) in any desired proportions. In a preferred embodiment of the invention, the inventive mixtures comprise the alkyl sulfosuccinate monoesters of the formula (I) and the alkyl sulfosuccinate monoesters of the formula (II) in a weight ratio of [10-1]:1, especially [8-1]:1, preferably [6-1.5]:1, especially [4-2]:1, more preferably [3.5-2.5]:1. In one embodiment of the invention, the mixtures comprise the alkyl sulfosuccinates of the formula (I) and the alkyl sulfosuccinates of the formula (II) in a weight ratio of 3:1.

These inventive mixtures may comprise the alkyl sulfosuccinate monoesters of the formulae (I) and (II) in any desired proportions. In a further embodiment of the invention, the inventive mixtures comprise the alkyl sulfosuccinate monoesters of the formula (II) and the alkyl sulfosuccinate monoesters of the formula (I) in a weight ratio of [10-1]:1, especially [8-1]:1, preferably [6-1.5]:1, especially [4-2]:1, more preferably [3.5-2.5]:1.

Accordingly, the present invention comprises, as one embodiment, mixtures of alkyl sulfosuccinate monoesters of the general formula (I)

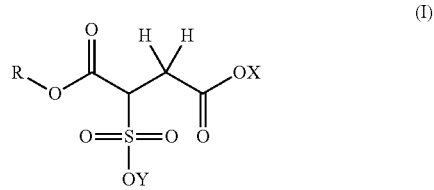

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and 30 to 70% by weight of C18-alkyl sulfosuccinate monoester, where the percentages by weight are based on the total amount of the C16- and C18-alkyl sulfosuccinate monoesters present in the mixture of the formula (I), and where the mixture comprises at least 50% by weight of C16- and C18-alkyl sulfosuccinate monoesters based on the sum of the alkyl sulfosuccinate monoesters of the formula (I).

In a preferred embodiment of the invention, this mixture comprises at least 60% by weight, preferably at least 70% by weight, especially at least 80% by weight, of C16- and C18-alkyl sulfosuccinate monoesters, based on the sum of the alkyl sulfosuccinate monoesters of the formula (I).

Accordingly, the present invention comprises, as one embodiment, mixtures of alkyl sulfosuccinate monoesters of the general formula (II)

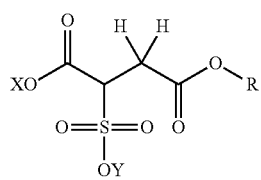

(II)

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises
- 30 to 70% by weight of C16-alkyl sulfosuccinate monoester and
- 30 to 70% by weight of C18-alkyl sulfosuccinate monoester, where the percentages by weight are based on the total amount of the C16- and C18-alkyl sulfosuccinate monoesters present in the mixture of the formula (II), and where the mixture comprises at least 50% by weight of C16- and C18-alkyl sulfosuccinate monoesters based on the sum of the alkyl sulfosuccinate monoesters of the formula (II).

In a preferred embodiment of the invention, this mixture comprises at least 60% by weight, preferably at least 70% by weight, especially at least 80% by weight, of C16- and C18-alkyl sulfosuccinate monoesters, based on the sum of the alkyl sulfosuccinate monoesters of the formula (II).

In a preferred embodiment of the invention, X and Y are each independently selected from the group consisting of Na, K, Mg, Ca and $NH_4$. Particular preference is given to mixtures in which X and Y are identical; X and Y are preferably each Na.

R is a linear or branched, saturated or unsaturated alkyl radical having 6 to 22 and preferably 8 to 18 carbon atoms. Examples include n-octyl, i-octyl, n-nonyl, i-nonyl, n-decyl, i-decyl, n-undecyl, i-undecyl, n-dodecyl (trivial name lauryl), i-dodecyl, n-tridecyl, i-tridecyl, n-tetradecyl, i-tetradecyl, n-pentadecyl, i-pentadecyl, n-hexadecyl (trivial name cetyl), hexadecyl, n-heptadecyl, i-heptadecyl, n-octadecyl (trivial name stearyl), i-octadecyl and n-octadecenyl (oleyl).

In this embodiment, the inventive mixture comprises 30 to 70 and preferably 40 to 60% by weight, especially 45 to 55% by weight, of C16-alkyl sulfosuccinate monoester, based on the total amount of the C16- and C18-alkyl sulfosuccinate monoesters present in the mixture. The term "C16-alkyl sulfosuccinate monoester" refers to compounds of the general formula (I) and/or (II) in which R is an alkyl radical having 16 carbon atoms. The mixture preferably comprises compounds of the general formula (I) and/or (II) in which R is a linear and saturated alkyl radical having 16 carbon atoms (=hexadecyl radical, trivial name cetyl radical).

In this embodiment, the inventive mixture comprises 30 to 70% by weight and preferably 40 to 60% by weight, especially 45 to 55% by weight, of C18-alkyl sulfosuccinate monoester, based on the total amount of the C16- and C18-alkyl sulfosuccinate monoesters present in the mixture. The term "C18-alkyl sulfosuccinate monoester" refers to compounds of the general formula (I) and/or (II) in which R is an alkyl radical having 18 carbon atoms. The mixture preferably comprises compounds of the general formula (I) and/or (II) in which R is a linear and saturated alkyl radical having 18 carbon atoms (=Octadecyl radical, trivial name stearyl radical).

As a result of the preparation, the inventive alkyl sulfosuccinate mixtures may comprise up to 30% by weight of secondary constituents. These are, for example, unconverted reactants from the esterification reaction (such as fatty alcohols or maleic anhydride) or by-products which form in the preparation, for example diesters. The term "mixtures of alkyl sulfosuccinate monoesters" thus includes mixtures which comprise at least 70% by weight of alkyl sulfosuccinate monoesters of the general formulae (I) and (II), and 0 to 30% by weight of secondary constituents.

In a preferred embodiment of the invention, the content of fatty alcohols is less than or equal to 10% by weight, preferably less than or equal to 5% by weight, based on the total amount of alkyl sulfosuccinate monoesters in the mixture.

Fatty alcohols in the context of the invention are understood to mean linear, saturated or unsaturated, primary alcohols (alkan-1-ols) having 6 to 22 carbon atoms.

It has been found that, surprisingly, mixtures of alkyl sulfosuccinate monoesters with a content of fatty alcohols of less than or equal to 10% by weight—based on the alkyl sulfosuccinate monoesters—can be spray-dried particularly efficiently, and it is thus possible in a technically simple manner to obtain powders.

Preparation

The inventive alkyl sulfosuccinate mixtures can be obtained, for example, by mixing C16-alkyl sulfosuccinate monoesters and C18-alkyl sulfosuccinate monoesters in the ratios claimed. The individual alkyl sulfosuccinate monoesters are obtainable, for example, by reaction of maleic anhydride with the appropriate C16 or C18 fatty alcohol by methods known to those skilled in the art. However, they can also be obtained, for example, by reaction of maleic anhydride with appropriate fatty alcohol mixtures. An example of a suitable fatty alcohol mixture is the C16/C18 fatty alcohol mixture, which is obtainable under the Lanette®O trade name from Cognis GmbH (technical name: cetearyl alcohol). Free fatty alcohol can be removed from the reaction mixture by methods known to those skilled in the art, for example by distillation.

Use

It has been found that, surprisingly, the inventive alkyl sulfosuccinate mixtures give stable cosmetic and/or pharmaceutical formulations. The inventive alkyl sulfosuccinate mixtures have especially been found to be advantageous emulsifiers. The inventive alkyl sulfosuccinate mixtures have additionally been found to be advantageous for the stabilization or dispersion of solid (active) ingredients in cosmetic and/or pharmaceutical formulations. Surprisingly, formulations with a high content of electrolytes are also obtained in stable form. In addition, the inventive alkyl sulfosuccinic mixtures enable stable incorporation or emulsification of pigments or UV filters into cosmetic and/or pharmaceutical formulations. In addition, the inventive alkyl sulfosuccinate mixtures exhibit surprising stability in alkaline formulations. They additionally enable cosmetic and/or pharmaceutical formulations to be obtained in stable form even at low pH. In addition, the inventive alkyl sulfosuccinate mixtures enable the production of stable emulsions. The inventive alkyl sulfosuccinate mixtures are therefore suitable as constituents of cosmetic and/or pharmaceutical formulations.

The invention provides for the use of a mixture of alkyl sulfosuccinate monoesters of the general formula (I) and/or (II)

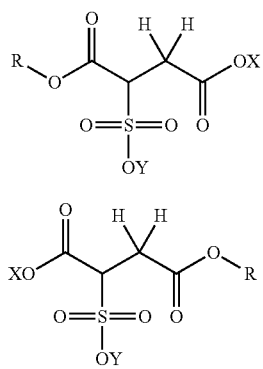

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises
- 30 to 70% by weight of C16-alkyl sulfosuccinate monoester and
- 30 to 70% by weight of C18-alkyl sulfosuccinate monoester, where the percentages by weight are based on the total amount of the alkyl sulfosuccinate monoesters of the formulae (I) and (II),
in cosmetic and/or pharmaceutical formulations.

These inventive mixtures may comprise the alkyl sulfosuccinate monoesters of the formulae (I) and (II) in any desired proportions. The inventive mixtures may comprise, for example, 0 to 90%, 0 to 80%, 0 to 70%, 0 to 60%, 0 to 50%, 0 to 40%, 0 to 30%, 0 to 20%, or 0 to 10% of the alkyl sulfosuccinate monoesters of the general formula (I). The inventive mixtures may comprise, for example, 10 to 100%, 20 to 100%, 30 to 100%, 40 to 100%, 50 to 100%, 60 to 100%, 70 to 100%, 80 to 100% or 90 to 100% of the alkyl sulfosuccinate monoesters of the general formula (I). The inventive mixtures may comprise, for example, 0 to 90%, 0 to 80%, 0 to 70%, 0 to 60%, 0 to 50%, 0 to 40%, 0 to 30%, 0 to 20%, or 0 to 10% of the alkyl sulfosuccinate monoesters of the general formula (II). The inventive mixtures may comprise, for example, 10 to 100%, 20 to 100%, 30 to 100%, 40 to 100%, 50 to 100%, 60 to 100%, 70 to 100%, 80 to 100% or 90 to 100% of the alkyl sulfosuccinate monoesters of the general formula (II).

These inventive mixtures may comprise the alkyl sulfosuccinate monoesters of the formulae (I) and (II) in any desired proportions. In a preferred embodiment of the invention, the inventive mixtures comprise the alkyl sulfosuccinate monoesters of the formula (I) and the alkyl sulfosuccinate monoesters of the formula (II) in a weight ratio of [10-1]:1, especially [8-1]:1, preferably [6-1.5]:1, especially [4-2]:1, more preferably [3.5-2.5]:1. In one embodiment of the invention, the mixtures comprise the alkyl sulfosuccinates of the formula (I) and the alkyl sulfosuccinates of the formula (II) in a weight ratio of 3:1.

These inventive mixtures may comprise the alkyl sulfosuccinate monoesters of the formulae (I) and (II) in any desired proportions. In a further embodiment of the invention, the inventive mixtures comprise the alkyl sulfosuccinate monoesters of the formula (II) and the alkyl sulfosuccinate monoesters of the formula (I) in a weight ratio of [10-1]:1, especially [8-1]:1, preferably [6-1.5]:1, especially [4-2]:1, more preferably [3.5-2.5]:1.

Accordingly, the present invention comprises, as one embodiment, the use of a mixture of alkyl sulfosuccinate monoesters of the general formula (I)

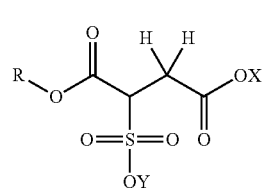

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises
- 30 to 70% by weight of C16-alkyl sulfosuccinate monoester and
- 30 to 70% by weight of C18-alkyl sulfosuccinate monoester, where the percentages by weight are based on the total amount of the alkyl sulfosuccinate monoesters of the formula (I),
in cosmetic and/or pharmaceutical formulations.

Accordingly, the present invention comprises, as one embodiment, the use of a mixture of alkyl sulfosuccinate monoesters of the general formula (II)

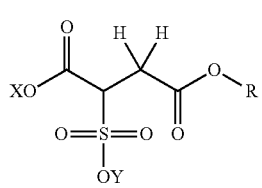

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises
- 30 to 70% by weight of C16-alkyl sulfosuccinate monoester and
- 30 to 70% by weight of C18-alkyl sulfosuccinate monoester, where the percentages by weight are based on the total amount of the alkyl sulfosuccinate monoesters of the formula (II),
in cosmetic and/or pharmaceutical formulations.

The inventive alkyl sulfosuccinate mixtures are especially suitable as an interface-active substance, for example as emulsifiers and/or disperants.

The invention further provides a cosmetic and/or pharmaceutical formulation comprising 0.1 to 50% by weight, preferably 0.5 to 10% by weight, based on the formulation, of a mixture of alkyl sulfosuccinate monoesters of the general formula (I) and/or (II)

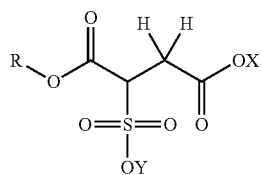
(I)

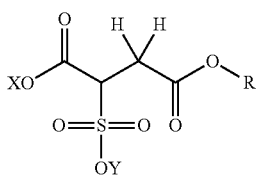
(II)

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and 30 to 70% by weight of C18-alkyl sulfosuccinate monoester, where the percentages by weight are based on the total amount of the alkyl sulfosuccinate monoesters of the formulae (I) and (II).

The invention more preferably provides a cosmetic and/or pharmaceutical formulation comprising 0.1 to 50% by weight, preferably 0.5 to 10% by weight, based on the formulation, of a mixture of alkyl sulfosuccinate monoesters of the general formula (I) and/or (II)

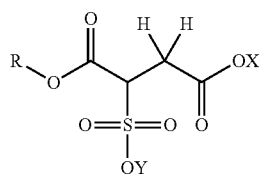
(I)

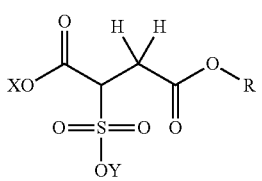
(II)

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and 30 to 70% by weight of C18-alkyl sulfosuccinate monoester, where the percentages by weight are based on the total amount of the alkyl sulfosuccinate monoesters of the formulae (I) and (II), characterized in that the formulation comprises less than 10% by weight, especially less than 5% by weight, of fatty alcohol—based on the alkyl sulfosuccinate monoesters of the general formulae (I) and (II).

The invention further provides for the use of a mixture of alkyl sulfosuccinate monoesters of the general formula (I) and/or (II)

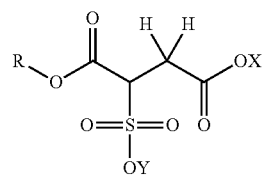
(I)

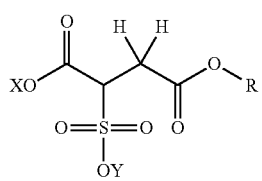
(II)

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and 30 to 70% by weight of C18-alkyl sulfosuccinate monoester, where the percentages by weight are based on the total amount of the C16- and C18-alkyl sulfosuccinate monoesters present in the mixture C16- and C18-alkyl sulfosuccinate monoesters of the formulae (I) and (II), and where the mixture comprises at least 50% by weight of C16- and C18-alkyl sulfosuccinate monoesters based on the sum of the alkyl sulfosuccinate monoesters of the formulae (I) and (II), in cosmetic and/or pharmaceutical formulations.

In a preferred embodiment of the invention, this mixture comprises at least 60% by weight, preferably at least 70% by weight, especially at least 80% by weight, of C16- and C18-alkyl sulfosuccinate monoesters, based on the sum of the alkyl sulfosuccinate monoesters of the formulae (I) and (II).

These inventive mixtures may comprise the alkyl sulfosuccinate monoesters of the formulae (I) and (II) in any desired proportions. The inventive mixtures may comprise, for example, 0 to 90%, 0 to 80%, 0 to 70%, 0 to 60%, 0 to 50%, 0 to 40%, 0 to 30%, 0 to 20%, or 0 to 10% of the alkyl sulfosuccinate monoesters of the general formula (I). The inventive mixtures may comprise, for example, 10 to 100%, 20 to 100%, 30 to 100%, 40 to 100%, 50 to 100%, 60 to 100%, 70 to 100%, 80 to 100% or 90 to 100% of the alkyl sulfosuccinate monoesters of the general formula (I). The inventive mixtures may comprise, for example, 0 to 90%, 0 to 80%, 0 to 70%, 0 to 60%, 0 to 50%, 0 to 40%, 0 to 30%, 0 to 20%, or 0 to 10% of the alkyl sulfosuccinate monoesters of the general formula (II). The inventive mixtures may comprise, for example, 10 to 100%, 20 to 100%, 30 to 100%, 40 to 100%, 50 to 100%, 60 to 100%, 70 to 100%, 80 to 100% or 90 to 100% of the alkyl sulfosuccinate monoesters of the general formula (II).

These inventive mixtures may comprise the alkyl sulfosuccinate monoesters of the formulae (I) and (II) in any desired proportions. In a preferred embodiment of the invention, the inventive mixtures comprise the alkyl sulfosuccinate monoesters of the formula (I) and the alkyl sulfosuccinate monoesters of the formula (II) in a weight ratio of [10-1]:1, especially [8-1]:1, preferably [6-1.5]:1, especially [4-2]:1, more preferably [3.5-2.5]:1. In one embodiment of the invention, the mixtures comprise the alkyl sulfosuccinates of the formula (I) and the alkyl sulfosuccinates of the formula (II) in a weight ratio of 3:1.

These inventive mixtures may comprise the alkyl sulfosuccinate monoesters of the formulae (I) and (II) in any desired proportions. In a further embodiment of the invention, the inventive mixtures comprise the alkyl sulfosuccinate monoesters of the formula (II) and the alkyl sulfosuccinate monoesters of the formula (I) in a weight ratio of [10-1]:1, especially [8-1]:1, preferably [6-1.5]:1, especially [4-2]:1, more preferably [3.5-2.5]:1.

Accordingly, the present invention comprises, as one embodiment, the use of a mixture of alkyl sulfosuccinate monoesters of the general formula (I)

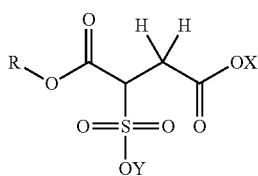

(I)

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises
- 30 to 70% by weight of C16-alkyl sulfosuccinate monoester and
- 30 to 70% by weight of C18-alkyl sulfosuccinate monoester, where the percentages by weight are based on the total amount of the C16- and C18-alkyl sulfosuccinate monoesters present in the mixture of the formula (I), and where the mixture comprises at least 50% by weight of C16- and C18-alkyl sulfosuccinate monoesters based on the sum of the alkyl sulfosuccinate monoesters of the formula (I), in cosmetic and/or pharmaceutical formulations.

In a preferred embodiment of the invention, this mixture comprises at least 60% by weight, preferably at least 70% by weight, especially at least 80% by weight, of C16- and C18-alkyl sulfosuccinate monoesters, based on the sum of the alkyl sulfosuccinate monoesters of the formula (I).

Accordingly, the present invention comprises, as one embodiment, the use of a mixture of alkyl sulfosuccinate monoesters of the general formula (II)

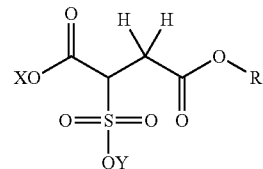

(II)

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises
- 30 to 70% by weight of C16-alkyl sulfosuccinate monoester and
- 30 to 70% by weight of C18-alkyl sulfosuccinate monoester, where the percentages by weight are based on the total amount of the C16- and C18-alkyl sulfosuccinate monoesters present in the mixture of the formula (II), and where the mixture comprises at least 50% by weight of C16- and C18-alkyl sulfosuccinate monoesters based on the sum of the alkyl sulfosuccinate monoesters of the formula (II), in cosmetic and/or pharmaceutical formulations.

In a preferred embodiment of the invention, this mixture comprises at least 60% by weight, preferably at least 70% by weight, especially at least 80% by weight, of C16- and C18-alkyl sulfosuccinate monoesters, based on the sum of the alkyl sulfosuccinate monoesters of the formula (II).

The inventive alkyl sulfosuccinate mixtures are especially suitable as an interface-active substance, for example as emulsifiers and/or disperants.

The invention further provides a cosmetic and/or pharmaceutical formulation comprising 0.1 to 50% by weight, preferably 0.5 to 10% by weight, based on the formulation, of a mixture of alkyl sulfosuccinate monoesters of the general formula (I) and/or (II)

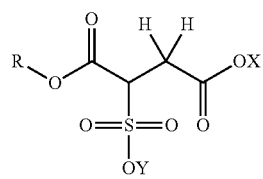

(I)

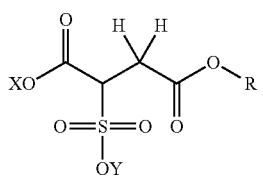

(II)

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and
30 to 70% by weight of C18-alkyl sulfosuccinate monoester, where the percentages by weight are based on the total amount of the C16- and C18-alkyl sulfosuccinate monoesters present in the mixture of the formulae (I) and (II),
and where the mixture comprises at least 50% by weight of C16- and C18-alkyl sulfosuccinate monoesters based on the sum of the alkyl sulfosuccinate monoesters of the formulae (I) and (II).

In a preferred embodiment of the invention, this mixture comprises at least 60% by weight, preferably at least 70% by weight, especially at least 80% by weight, of C16- and C18-alkyl sulfosuccinate monoesters, based on the sum of the alkyl sulfosuccinate monoesters of the formulae (I) and (II).

The invention more preferably provides a cosmetic and/or pharmaceutical formulation comprising 0.1 to 50% by weight, preferably 0.5 to 10% by weight, based on the formulation, of a mixture of alkyl sulfosuccinate monoesters of the general formula (I) and/or (II)

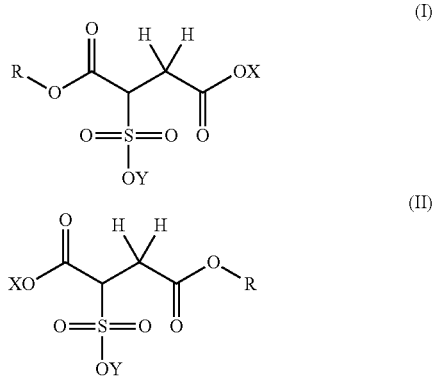

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and
30 to 70% by weight of C18-alkyl sulfosuccinate monoester, where the percentages by weight are based on the total amount of the C16- and C18-alkyl sulfosuccinate monoesters present in the mixture of the formulae (I) and (II),
and where the mixture comprises at least 50% by weight of C16- and C18-alkyl sulfosuccinate monoesters based on the sum of the alkyl sulfosuccinate monoesters of the formulae (I) and (II);
characterized in that the formulation comprises less than 10% by weight, especially less than 5% by weight, of fatty alcohol—based on the alkyl sulfosuccinate monoesters of the general formulae (I) and (II).

In a preferred embodiment of the invention, this mixture comprises at least 60% by weight, preferably at least 70% by weight, especially at least 80% by weight, of C16- and C18-alkyl sulfosuccinate monoesters, based on the sum of the alkyl sulfosuccinate monoesters of the formulae (I) and (II).

The cosmetic and/or pharmaceutical formulations may be formulations for bodycare, for example a body milk, creams, lotions, sprayable emulsions, products for eliminating body odor, etc. The inventive alkyl sulfosuccinate mixtures can also be used in surfactant-comprising formulations, for example shower and bath gels, shampoos and care rinses. According to the end application, the cosmetic and/or pharmaceutical formulations comprise a series of further assistants and additives, for example surfactants, oil bodies, (further) interface-active substances, such as emulsifiers or surfactants, pearlescent waxes, bodying agents, thickeners, superfatting agents, stabilizers, polymers, fats, waxes, lecithins, phospholipids, biogenic active ingredients, antidandruff agents, film formers, swelling agents, insect repellents, self-tanning agents, tyrosinase inhibitors (depigmenting agents), hydrotropes, solubilizers, preservatives, perfume oils, dyes, etc.

The inventive cosmetic and/or pharmaceutical formulations may be present, for example, as O/W or W/O care emulsions, as multiple emulsions, for example W/O/W or O/W/O emulsions, sunscreen formulations, antiperspirant/deodorant concepts, formulations for decorative cosmetics, oily care formulations, and impregnation liquids for substrates, for example paper and nonwoven products. Examples include wet wipes, tissues, diapers or hygiene products.

The inventive alkyl sulfosuccinate mixtures and the inventive cosmetic and/or pharmaceutical formulations are especially also suitable for light, sprayable applications and/or as constituents of care emulsions for tissues, papers, wipes, sponges (e.g. polyurethane sponges), plasters in the baby hygiene sector, babycare, skincare, sun protection, aftersun treatment, insect repellency, cleansing, face cleansing and antiperspirant/deodorant applications. They can be applied to tissues, papers, wipes, nonwoven products, sponges, puffs, plasters and bandages which find use in the cleansing, hygiene and/or care sectors (wet wipes for baby hygiene and babycare, cleansing wipes, face cleansing wipes, skincare wipes, care wipes with active ingredients to counteract skin aging, wipes with sunscreen formulations and insect repellents, and wipes for decorative cosmetics or for aftersun treatment, toilet wet wipes, antiperspirant wipes, diapers, tissues, wet wipes, hygiene products, self-tanning wipes, toilet paper, refreshing wipes, aftershave wipes). They can also be used in formulations for hair care, hair cleaning or hair coloring. The inventive alkyl sulfosuccinate mixtures are suitable especially as constituents of decorative cosmetics formulations, for example lipsticks, eye makeup, for example eyeshadow, mascara, eye pencils, kohl, nail varnish, etc., and makeup formulations.

The inventive alkyl sulfosuccinate mixtures can be used especially to stably emulsify or disperse UV photoprotective filters. The invention therefore further provides a cosmetic and/or pharmaceutical formulation comprising, in a cosmetically and/or pharmaceutically suitable carrier, 0.1 to 50% by weight, preferably 0.5 to 10% by weight, based on the formulation, of a mixture of alkyl sulfosuccinate monoesters of the general formula (I) and/or (II)

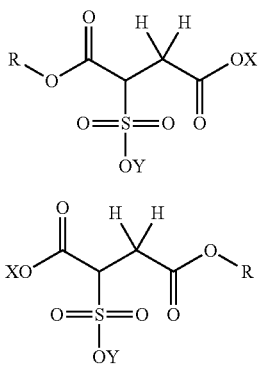

(I)

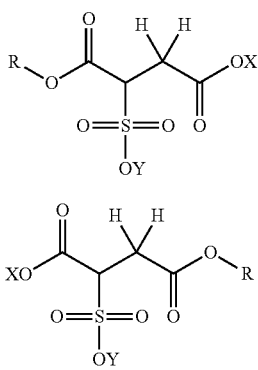

(II)

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and
30 to 70% by weight of C18-alkyl sulfosuccinate monoester, where the percentages by weight are based on the total amount of the alkyl sulfosuccinate monoesters of the formulae (I) and (II), and at least one UV photoprotective filter.

The invention further provides a cosmetic and/or pharmaceutical formulation comprising, in a cosmetically and/or pharmaceutically suitable carrier, 0.1 to 50% by weight, preferably 0.5 to 10% by weight, based on the formulation, of a mixture of alkyl sulfosuccinate monoesters of the general formula (I) and/or (II)

(I)

(II)

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and
30 to 70% by weight of C18-alkyl sulfosuccinate monoester, where the percentages by weight are based on the total amount of the C16- and C18-alkyl sulfosuccinate monoesters present in the mixture of the formulae (I) and (II), and where the mixture comprises at least 50% by weight of C16- and C18-alkyl sulfosuccinate monoesters based on the sum of the alkyl sulfosuccinate monoesters of the formulae (I) and (II), and at least one UV photoprotective filter.

In a preferred embodiment of the invention, this mixture comprises at least 60% by weight, preferably at least 70% by weight, especially at least 80% by weight, of C16- and C18-alkyl sulfosuccinate monoesters, based on the sum of the alkyl sulfosuccinate monoesters of the formulae (I) and (II).

According to the invention, suitable UV photoprotective filters are room temperature liquid or crystalline organic substances (photoprotective filters) which are capable of absorbing ultraviolet rays and releasing the energy absorbed again in the form of longer-wave radiation, for example heat. UV filters may be oil-soluble or water-soluble. Examples of typical oil-soluble UV B filters or broad-spectrum UV A/B filters include:

3-benzylidenecamphor or 3-benzylidenenorcamphor (Mexoryl SDS 20) and derivatives thereof, e.g. 3-(4-methylbenzylidene)camphor as described in EP 0693471 B1

3-(4'-trimethylammonium)benzylidenebornan-2-one methylsulfate (Mexoryl SO)

3,3'-(1,4-phenylenedimethine)bis(7,7-dimethyl-2-oxobicyclo[2.2.1]heptane-1-methanesulfonic acid) and salts (Mexoryl SX)

3-(4'-sulfo)benzylidenebornan-2-one and salts (Mexoryl SL)

polymer of N-{(2 and 4)-[(2-oxoborn-3-ylidene)-methyl]benzyl}acrylamide (Mexoryl SW)

2-(2H-benzotriazol-2-yl)-4-methyl-6-(2-methyl-3-(1,3,3,3-tetramethyl-1-(trimethylsilyloxy)-disiloxanyl)propyl)phenol (Mexoryl SL)

4-aminobenzoic acid derivatives, preferably 2-ethylhexyl 4-(dimethylamino)benzoate, 2-octyl 4-(dimethylamino)benzoate and amyl 4-(dimethylamino) benzoate;

esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di-2-ethylhexyl 4-methoxybenzmalonate;

triazine derivatives, for example 2, 4,6-trianilino(p-carbo-2'-ethyl-1'-hexyloxy)-1,3,5-triazine and 2,4,6-tris[p-(2-ethylhexyloxycarbonyl)-anilino]-1,3,5-triazine (Uvinul T 150), as described in EP 0818450 A1 or bis(2-ethylhexyl) 4,4'-[(6-[((1,1-dimethylethyl)aminocarbonyl)phenylamino]-1,3,5-triazine-2,4-diyl)diimino]benzoate (Uvasorb® HEB);

2,2-methylenebis(6-(2H-benzotriazol-2-yl)-4-(1,1,3,3-tetramethylbutyl)phenol) (Tinosorb M);

2,4-bis[4-(2-ethylhexyloxy)-2-hydroxyphenyl]-6-(4-methoxyphenyl)-1,3,5-triazine (Tinosorb S);

propane-1,3-diones, for example 1-(4-tert-butylphenyl)-3-(4'-methoxyphenyl)propane-1,3-dione;
ketotricyclo(5.2.1.0)decane derivatives, as described in EP 0694521 B1;
dimethicodiethylbenzal malonate (Parsol SLX).
Useful water-soluble UV filters include:
2-phenylbenzimidazole-5-sulfonic acid and the alkali metal, alkaline earth metal, ammonium, alkyl-ammonium, alkanolammonium and glucammonium salts thereof;
2,2-(1,4-phenylene)bis(1H-benzimidazole-4,6-disulfonic acid, monosodium salt) (Neo Heliopan AP);
sulfonic acid derivatives of benzophenones, preferably 2-hydroxy-4-methoxybenzophenone-5-sulfonic acid and its salts;
sulfonic acid derivatives of 3-benzylidenecamphor, for example 4-(2-oxo-3-bornylidenemethyl)benzene-sulfonic acid and 2-methyl-5-(2-oxo-3-bornylidene)-sulfonic acid and salts thereof.

Useful typical UV A filters are especially derivatives of benzoylmethane, for example 1-(4'-tert-butylphenyl)-3-(4'-methoxyphenyl)propane-1,3-dione, 4-tert-butyl-4'-methoxydibenzoylmethane (Parsol® 1789), 1-phenyl-3-(4'-isopropylphenyl)propane-1,3-dione, and enamine compounds, as described in DE 19712033 A1 (BASF), and also benzoic acid 2-[4-(diethylamino)-2-hydroxybenzoyl] hexyl ester (Uvinul® A plus).

The UV A and UV B filters can of course also be used in mixtures. Particularly favorable combinations consist of the derivatives of benzoylmethane, e.g. 4-tert-butyl-4'-methoxydibenzoylmethane (Parsol® 1789) and 2-ethylhexyl 2-cyano-3,3-phenylcinnamate(octocrylene) in combination with esters of cinnamic acid, preferably 2-ethylhexyl 4-methoxycinnamate and/or propyl 4-methoxycinnamate and/or isoamyl 4-methoxycinnamate. Combinations of this type are advantageously combined with water-soluble filters, for example 2-phenyl-benzimidazole-5-sulfonic acid and the alkali metal, alkaline earth metal, ammonium, alkylammonium, alkanolammonium and glucammonium salts thereof.

Suitable UV photoprotective filters are especially the substances approved according to Annex VII of the Commission Directive (in the version: Commission Directive 2005/9/EC of Jan. 28, 2005 amending Council Directive 76/768/EEC, concerning cosmetic products, for the purposes of adapting Annexes VII thereof to technical progress), to which reference is hereby explicitly made.

In addition to the aforementioned groups of primary photoprotective substances, it is also possible to use secondary photoprotective agents of the antioxidant type, which interrupt the photochemical reaction chain which is triggered when UV radiation penetrates into the skin. Typical examples thereof are amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. -carotene, -carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, linoleyl, cholesteryl and glyceryl esters thereof), and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to mol/kg), also (metal) chelating agents (e.g. α-hydroxy fatty acids, palmitic acid, phytic acid, lactoferrin), α-hydroxy acids (e.g. citric acid, lactic acid, malic acid), humic acid, gallic acid, bile extracts, bilirubin, biliverdin, EDTA, EGTA and derivatives thereof, unsaturated fatty acids and derivatives thereof (e.g. gamma-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, ZnSO$_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids), suitable in accordance with the invention, of these specified active ingredients.

The invention provides cosmetic and/or pharmaceutical formulations comprising, in a cosmetically and/or pharmaceutically suitable carrier, 0.1 to 50% by weight, preferably 0.5 to 10% by weight, based on the formulation, of a mixture of alkyl sulfosuccinate monoesters of the general formula (I) and/or (II)

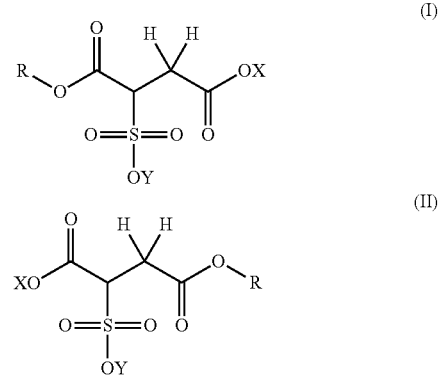

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises
   30 to 70% by weight of C16-alkyl sulfosuccinate monoester and
   30 to 70% by weight of C18-alkyl sulfosuccinate monoester,
where the percentages by weight are based on the total amount of the alkyl sulfosuccinate monoesters of the formulae (I) and (II),
and at least one UV photoprotective filter selected from the group consisting of 4-Methylbenzylidene Camphor, Benzophenone-3, Butyl Methoxydibenzoylmethane, Bis-Ethylhexyloxyphenol Methoxyphenyl Triazine, Methylene Bis-Benzotriazolyl Tetramethylbutylphenol, Diethylhexyl Butamido Triazone, Ethylhexyl Triazone and Diethylamino Hydroxybenzoyl Hexyl Benzoate, 3-(4'-trimethylammonium)benzylidenebornan-2-one methylsulfate, 3,3'-(1,4-phenylenedimethine)bis(7,7-dimethyl-2-oxobicyclo[2.2.1]heptane-1-methanesulfonic acid) and its salts, 3-(4'-sulfo)benzylidenebornan-2-one and its salts, polymer of N-{(2 and 4)-[(2-oxoborn-3-ylidene)methyl]benzyl}acrylamide, 2-(2H-benzotriazol-2-yl)-4-methyl-6-(2-methyl-3-(1,3,3,3-tetramethyl-1-(trimethylsilyloxy)disiloxanyl)propyl)phenol, dimethicodiethylbenzal malonate and mixtures thereof.

The invention provides cosmetic and/or pharmaceutical formulations comprising, in a cosmetically and/or pharmaceutically suitable carrier, 0.1 to 50% by weight, preferably 0.5 to 10% by weight, based on the formulation, of a mixture of alkyl sulfosuccinate monoesters of the general formula (I) and/or (II)

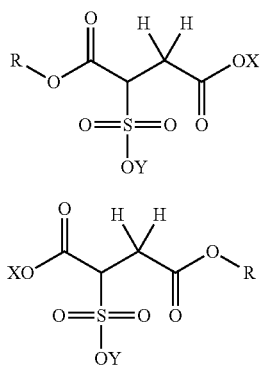

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises
  30 to 70% by weight of C16-alkyl sulfosuccinate monoester and
  30 to 70% by weight of C18-alkyl sulfosuccinate monoester,
where the percentages by weight are based on the total amount of the C16- and C18-alkyl sulfosuccinate monoesters present in the mixture of the formulae (I) and (II),
and where the mixture comprises at least 50% by weight of C16- and C18-alkyl sulfosuccinate monoesters based on the sum of the alkyl sulfosuccinate monoesters of the formulae (I) and (II);
and at least one UV photoprotective filter selected from the group consisting of 4-Methylbenzylidene Camphor, Benzophenone-3, Butyl Methoxydibenzoylmethane, Bis-Ethylhexyloxyphenol Methoxyphenyl Triazine, Methylene Bis-Benzotriazolyl Tetramethylbutylphenol, Diethylhexyl Butamido Triazone, Ethylhexyl Triazone and Diethylamino Hydroxybenzoyl Hexyl Benzoate, 3-(4'-trimethylammonium)benzylidenebornan-2-one methylsulfate, 3,3'-(1,4-phenylenedimethine)bis(7,7-dimethyl-2-oxobicyclo[2.2.1]heptane-1-methanesulfonic acid) and its salts, 3-(4'-sulfo)benzylidenebornan-2-one and its salts, polymer of N-{(2 and 4)-[(2-oxoborn-3-ylidene)methyl]benzyl}acrylamide, 2-(2H-benzotriazol-2-yl)-4-methyl-6-(2-methyl-3-(1,3,3,3-tetramethyl-1-(trimethylsilyloxy)disiloxanyl)propyl)phenol, dimethicodiethylbenzal malonate and mixtures thereof.

In a preferred embodiment of the invention, this mixture comprises at least 60% by weight, preferably at least 70% by weight, especially at least 80% by weight, of C16- and C18-alkyl sulfosuccinate monoesters based on the sum of the alkyl sulfosuccinate monoesters of the formulae (I) and (II).

These UV photoprotective filters are commercially available, for example, under the following trade names:
NeoHeliopan®MBC (INCI: 4-Methylbenzylidene Camphor; manufacturer: Symrise); NeoHeliopan®BB (INCI: Benzophenone-3, manufacturer: Symrise); Parsol®1789 (INCI: Butyl Methoxydibenzoylmethane, manufacturer: Hoffmann-La Roche (Givaudan)); Tinosorb®S (INCI: Bis-Ethylhexyloxyphenol Methoxyphenyl Triazine); Tinosorb®M (INCI: Methylene Bis-Benzotriazolyl Tetramethylbutylphenol: manufacturer: Ciba Specialty Chemicals Corporation); Uvasorb®HEB (INCI: Diethylhexyl Butamido Triazone, manufacturer: 3V Inc.); Uvinul® 150 (INCI: Ethylhexyl Triazone, manufacturer: BASF AG); Uvinul® A plus (INCI: Diethylamino Hydroxybenzoyl Hexyl Benzoate: manufacturer: BASF AG); Mexoryl® SO: 3-(4'-trimethylammonium)benzylidenebornan-2-one methylsulfate, INCI: Camphor Benzalkonium Methosulfate; Mexoryl®SX: 3,3'-(1,4-phenylenedimethine)bis(7,7-dimethyl-2-oxobicyclo[2.2.1]heptane-1-methanesulfonic acid), CTFA: INCI Terephthalylidene Dicamphor Sulfonic Acid; Mexoryl® SL: 3-(4'-sulfo)benzylidenebornan-2-one, INCI Benzylidene Camphor Sulfonic Acid; Mexoryl®SW: polymer of N-{(2 and 4)-[(2-oxoborn-3-ylidene)methyl]-benzyl}acrylamide, INCI Polyacrylamidomethyl Benzylidene Camphor; Mexoryl®SL: 2-(2H-benzotriazol-2-yl)-4-methyl-6-(2-methyl-3-(1,3,3,3-tetramethyl-1-(trimethylsilyloxy)disiloxanyl)propyl)phenol, INCI: Benzylidene camphor sulfonic acid; Parsol® SLX: dimethicodiethylbenzal malonate, INCI Polysilicone-15; Mexoryl®XL: 2-(2H-benzotriazol-2-yl)-4-methyl-6-(2-methyl-3-(1,3,3,3-tetramethyl-1-(trimethylsilyloxy)disiloxanyl)propyl)phenol, INCI: Drometrizole trisiloxane.

The invention provides cosmetic and/or pharmaceutical formulations comprising, in a cosmetically and/or pharmaceutically suitable carrier, 0.1 to 50% by weight, preferably 0.5 to 10% by weight, based on the formulation, of a mixture of alkyl sulfosuccinate monoesters of the general formula (I) and/or (II)

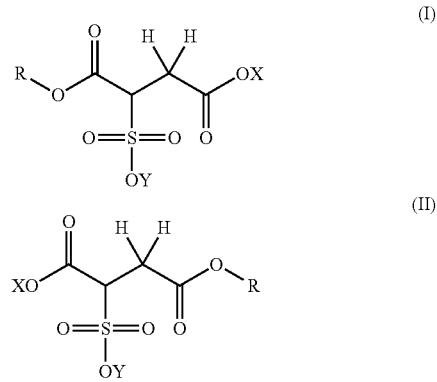

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and 30 to 70% by weight of C18-alkyl sulfosuccinate monoester, where the percentages by weight are based on the total amount of the alkyl sulfosuccinate monoesters of the formulae (I) and (II), and at least one UV photoprotective filter selected from the group of the photoprotective pigments, especially from the group of the zinc oxides and titanium oxides.

The invention provides cosmetic and/or pharmaceutical formulations comprising, in a cosmetically and/or pharmaceutically suitable carrier, 0.1 to 50% by weight, preferably 0.5 to 10% by weight, based on the formulation, of a mixture of alkyl sulfosuccinate monoesters of the general formula (I) and/or (II)

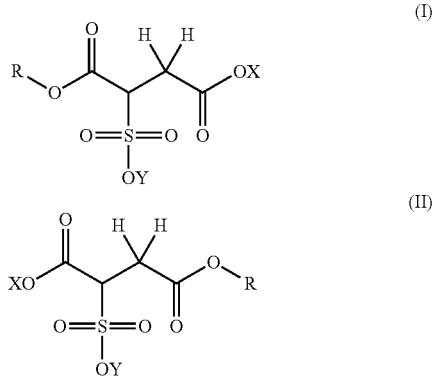

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and 30 to 70% by weight of C18-alkyl sulfosuccinate monoester, where the percentages by weight are based on the total amount of the C16- and C18-alkyl sulfosuccinate monoesters present in the mixture of the formulae (I) and (II), and where the mixture comprises at least 50% by weight of C16- and C18-alkyl sulfosuccinate monoesters based on the sum of the alkyl sulfosuccinate monoesters of the formulae (I) and (II);

and at least one UV photoprotective filter selected from the group of the photoprotective pigments, especially from the group of the zinc oxides and titanium oxides.

In a preferred embodiment of the invention, this mixture comprises at least 60% by weight, preferably at least 70% by weight, especially at least 80% by weight, of C16- and C18-alkyl sulfosuccinate monoesters, based on the sum of the alkyl sulfosuccinate monoesters of the formulae (I) and (II).

It has been found that, surprisingly, the inventive alkyl sulfosuccinate mixtures efficiently disperse or stabilize UV photoprotective filters, especially photoprotective pigments, and thus ensure homogeneous distribution of the UV photoprotective filter in the cosmetic and/or pharmaceutical formulation.

Useful photoprotective pigments include finely dispersed metal oxides and salts. Examples of suitable metal oxides are especially zinc oxide and titanium dioxide, and additionally oxides of iron, of zirconium, of silicon, of manganese, of aluminum and of cerium, and mixtures thereof. The salts used may be silicates (talc), barium sulfate or zinc stearate. The oxides and salts are used in the form of the pigments for skincare and skin-protecting emulsions, and also for decorative cosmetics. The particles should have a mean diameter of less than 100 nm, preferably between 5 and 50 nm and especially between 15 and 30 nm. They may have a spherical shape, but it is also possible to use those particles which have an ellipsoidal shape or a shape which deviates in some other way from the spherical configuration. The pigments may also be present in surface-treated form, i.e. hydrophilized or hydrophobized. Typical examples thereof are coated titanium dioxides, for example T 805 titanium dioxide (Degussa) or Eusolex® T, Eusolex® T-2000, Eusolex® T-Aqua, Eusolex® AVO, Eusolex® T-ECO, Eusolex® T-OLEO and Eusolex® T-S (Merck). Typical examples thereof are zinc oxides, for example Zinc Oxide neutral, Zinc Oxide NDM (Symrise) or Z-Cote® (BASF) or SUNZnO-AS and SUNZnO-NAS (Sunjun Chemical Co. Ltd.). Suitable hydrophobic coatings are in particular silicones and specifically trialkoxyoctylsilanes or simethicones. In sunscreen compositions, preference is given to using micropigments or nanopigments. Preference is given to using micronized zinc oxide. Further suitable UV photoprotective filters can be found in the review by P. Finkel in SÖFW-Journal 122, 8/1996, pp. 543-548 and Parf. Kosm., volume 80, no. 3/1999, p. 10 to 16.

The inventive formulations may comprise the UV photoprotective filters in amounts of 0.5 to 30% by weight, preferably 2.5 to 20% by weight, more preferably 5-15% by weight—based on the total weight of the cosmetic and/or pharmaceutical formulation.

The invention provides cosmetic formulations for coloring skin and hair, comprising, in a cosmetically and/or pharmaceutically suitable carrier, 0.1 to 50% by weight, preferably 0.5 to 10% by weight, based on the formulation, of a mixture of alkyl sulfosuccinate monoesters of the general formula (I) and/or (II)

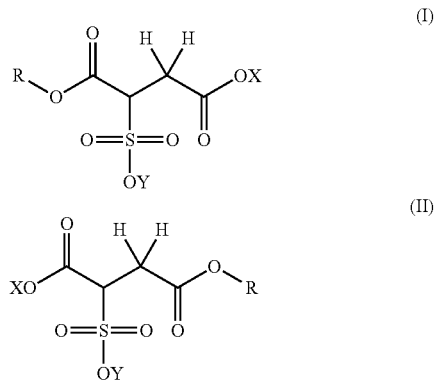

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises
- 30 to 70% by weight of C16-alkyl sulfosuccinate monoester and
- 30 to 70% by weight of C18-alkyl sulfosuccinate monoester, where the percentages by weight are based on the total amount of the alkyl sulfosuccinate monoesters of the formulae (I) and (II),
and at least one direct dye or an oxidation dye precursor.

The invention further provides for the use of this cosmetic formulation for coloring hair, and to a method for coloring hair or for refreshing hair color with this formulation.

The invention provides cosmetic formulations for coloring skin and hair, comprising, in a cosmetically and/or pharmaceutically suitable carrier, 0.1 to 50% by weight, preferably 0.5 to 10% by weight, based on the formulation, of a mixture of alkyl sulfosuccinate monoesters of the general formula (I) and/or (II)

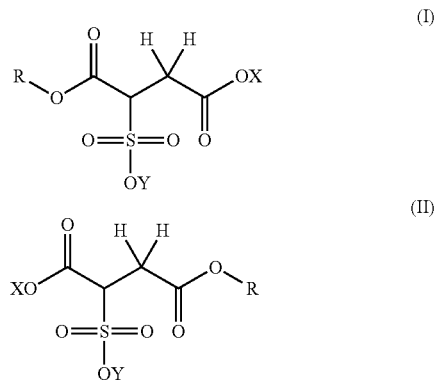

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises
- 30 to 70% by weight of C16-alkyl sulfosuccinate monoester and
- 30 to 70% by weight of C18-alkyl sulfosuccinate monoester, where the percentages by weight are based on the total amount of the C16- and C18-alkyl sulfosuccinate monoesters present in the mixture of the formulae (I) and (II),
and where the mixture comprises at least 50% by weight of C16- and C18-alkyl sulfosuccinate monoesters based on the sum of the alkyl sulfosuccinate monoesters of the formulae (I) and (II);
and at least one direct dye or an oxidation dye precursor.

In a preferred embodiment of the invention, this mixture comprises at least 60% by weight, preferably at least 70% by weight, especially at least 80% by weight, of C16- and C18-alkyl sulfosuccinate monoesters, based on the sum of the alkyl sulfosuccinate monoesters of the formulae (I) and (II).

The invention further provides for the use of this cosmetic formulation for coloring hair, and to a method for coloring hair or for refreshing hair color with this formulation.

For the coloring of hair, generally either direct dyes or oxidation dyes, which result from oxidative coupling of one or more developer components with one another or with one or more coupler components, are employed. Coupler and developer components are also referred to as oxidation dye precursors. The developer components used are typically primary aromatic amines with a further free or substituted hydroxyl or amino group in the para or ortho position, diaminopyridine derivatives, heterocyclic hydrazones, 4-aminopyrazolone derivatives, and 2,4,5,6-tetraminopyrimidine and derivatives thereof. Specific representatives are, for example, p-phenylenediamine, p-toluoylenediamine, 2,4,5,6-tetraminopyrimidine, p-aminophenol, N,N-bis(2-hydroxyethyl)-p-phenylenediamine, 2-(2,5-diaminophenyl)ethanol, 2-(2,5-diaminophenoxy)ethanol, 1-phenyl-3-carboxamido-4-amino-5-pyrazolone, 4-amino-3-methylphenol, 2-aminomethyl-4-aminophenol, 2-hydroxymethyl-4-aminophenol, 2-hydroxy-4,5,6-triaminopyrimidine, 2,4-dihydroxy-5,6-diaminopyrimidine and 2,5,6-triamino-4-hydroxypyrimidine. The coupler components used are generally m-phenylenediamine derivatives, naphthols, resorcinol and resorcinol derivatives, pyrazolones and m-aminophenols. Suitable coupler substances are especially c-naphtho" 1,5-, 2,7- and 1,7-dihydroxynaphthalene, 5-amino-2-methylphenol, m-aminophenol, resorcinol, resorcinol monomethyl ether, m-phenylenediamine, 2,4-diaminophenoxyethanol, 1-phenyl-3-methyl-5-pyrazolone, 2,4-dichloro-3-aminophenol, 1,3-bis(2,4-diaminophenoxy)propane, 2-chlororesorcinol, 4-chlororesorcinol, 2-chloro-6-methyl-3-aminophenol, 2-methylresorcinol and 5-methylresorcinol. With regard to further customary dye components, reference is made explicitly to the "Dermatology" series, edited by Ch. Culnan, H. Maibach, Marcel Dekker Inc. publishers, New York, Basle, 1986, Vol. 7, Ch. Zviak, The Science of Hair Care, Ch. 7, pages 248-250 (direct dyes), and Ch. 8, pages 264-267 (oxidation dyes), and the "European inventory of cosmetic ingredients", 1996, published by the European Commission [Hnhd-01938 (203-058-I)], obtainable in diskette form from the Bundesverband der deutschen Industrie- und Handelsunternehmen für Arzneimittel, Reformwaren und Korperpflegemittel e. V., Mannheim.

Hair colorants, especially when the coloring is effected oxidatively, whether with atmospheric oxygen or other oxidizing agents such as hydrogen peroxide, are typically weakly acidic to alkaline, i.e. have pH values in the range from about 5 to 11. For this purpose, the colorants comprise alkalizing agents, typically alkali metal or alkaline earth metal hydroxides, ammonia or organic amines. Preferred alkalizing agents are monoethanolamine, monoisopropanolamine, 2-amino-2-methylpropanol, 2-amino-2-methyl-1,3-propanediol, 2-amino-2-ethyl-1,3-propanediol, 2-amino-2-methylbutanol and triethanolamine, and also alkali metal and alkaline earth metal hydroxides. Especially monoethanolamine, triethanolamine, and also 2-amino-2-methylpropanol and 2-amino-2-methyl-1,3-propanediol, are preferred in the context of this group. The use of omega-amino acids such as omega-aminocaproic acid as alkalizing agents is also possible.

When the actual hair coloring proceeds within an oxidative process, it is possible to use customary oxidizing agents, such as especially hydrogen peroxide or addition products thereof onto urea, melamine or sodium borate. Oxidation with atmospheric oxygen as the sole oxidizing agent may, however, be preferred. It is additionally possible to perform the oxidation with the aid of enzymes, in which case the enzymes are used both to obtain oxidizing per compounds and to reinforce the action of a small amount of oxidizing agents present, or else enzymes which transfer electrons from suitable developer components (reducing agents) to atmospheric oxygen. Preference is given to oxidases such as tyrosinase, ascorbate oxidase and laccase, but also glucose oxidase, uricase or pyruvate oxidase. Mention should also be made of the method of enhancing the effect of small amounts (e.g. 1% or less, based on the overall formulation) of hydrogen peroxide by means of peroxidases.

Appropriately, the formulation of the oxidizing agent is then mixed with the formulation comprising the oxidation dye precursor immediately prior to the coloring of the hair. The ready-to-use hair-coloring preparation which forms should preferably have a pH in the range from 6 to 10. Particular preference is given to the use of the hair-coloring agent in a weakly alkaline medium. The use temperatures may be within a range between 15 and 40° C., preferably the temperature of the scalp. After a contact time of approx. 5 to 45 and especially 15 to 30 minutes, the hair-coloring agent is removed from the hair to be colored by rinsing. Subsequent washing with a shampoo is dispensed with when a carrier with a high surfactant content, for example a coloring shampoo, has been used.

Especially in the case of hair which is difficult to color, the formulation comprising the oxidation dye precursor can be applied to the hair without preceding mixing with the oxidation component. After a contact time of 20 to 30 minutes—optionally after an intermediate rinse—the oxidation component is then applied. A further contact time of 10 to 20 minutes is then followed by rinsing and, if desired, subsequent shampooing. In this embodiment, in a first variant in which the preceding application of the oxidation dye precursor is supposed to result in better penetration into the hair, the corresponding formulation is set to a pH of about 4 to 7. In a second variant, the first aim is air oxidation, in which case the formulation applied preferably has a pH of 7 to 10. In the subsequent accelerated post-oxidation, the use of acidified peroxodisulfate solutions as an oxidizing agent may be preferred.

In addition, the formation of the color can be promoted and enhanced by adding particular metal ions to the composition. Such metal ions are, for example, $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$ and $Al^{3+}$. Particularly suitable are $Zn^{2+}$, $Cu^{2+}$ and $Mn^{2+}$. The metal ions may in principle be used in the form of any physiologically compatible salt. Preferred salts are the acetates, sulfates, halides, lactates and tartrates. Use of these metal salts allows both the formation of the color to be accelerated and the color shade to be influenced in a controlled manner.

The direct dyes or oxidation dye precursors are typically used in concentrations of 0.001 to 0.1% by weight, based on the total weight of the formulation.

The pH of the inventive formulations may in principle be at values of 2-11. According to the purpose and the use of the inventive composition, the pH can be selected and adjusted in an entirely controlled manner. For colorants, it is, for example, preferably between 5 and 11, particular preference being given to values of 6 to 10. To establish this pH, it is possible to use virtually any acid or base usable for cosmetic purposes. Preferred bases are ammonia, alkali metal hydroxides, monoethanolamine, triethanolamine and N,N,N',N'-tetrakis(2-hydroxypropyl)ethylenediamine. Typically, the acids used are food acids. Food acids are understood to mean those acids which are consumed within typical food consumption and have positive effects on the human organism. Food acids are, for example, acetic acid, lactic acid, tartaric acid, citric acid, malic acid, ascorbic acid and gluconic acid.

The invention provides cosmetic and/or pharmaceutical formulations comprising, in a cosmetically and/or pharmaceutically suitable carrier, 0.1 to 50% by weight, preferably 0.5 to 10% by weight, based on the formulation, of a mixture of alkyl sulfosuccinate monoesters of the general formula (I) and/or (II)

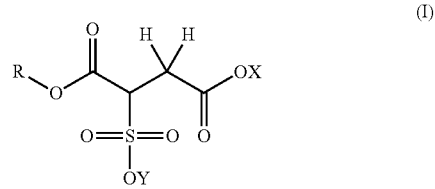

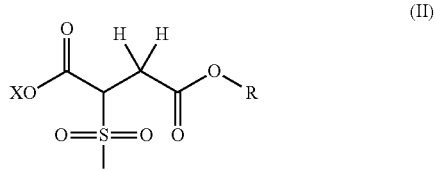

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and 30 to 70% by weight of C18-alkyl sulfosuccinate monoester, where the percentages by weight are based on the total amount of the alkyl sulfosuccinate monoesters of the formulae (I) and (II), and at least one active antiperspirant/deodorant ingredient.

The invention further provides cosmetic and/or pharmaceutical formulations comprising, in a cosmetically and/or pharmaceutically suitable carrier, 0.1 to 50% by weight, preferably 0.5 to 10% by weight, based on the formulation, of a mixture of alkyl sulfosuccinate monoesters of the general formula (I) and/or (II)

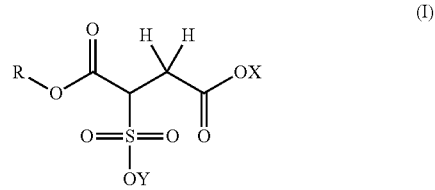

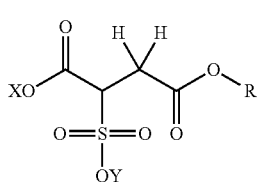

(II)

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises
  30 to 70% by weight of C16-alkyl sulfosuccinate monoester and
  30 to 70% by weight of C18-alkyl sulfosuccinate monoester,
where the percentages by weight are based on the total amount of the C16- and C18-alkyl sulfosuccinate monoesters present in the mixture of the formulae (I) and (II),
and where the mixture comprises at least 50% by weight of C16- and C18-alkyl sulfosuccinate monoesters based on the sum of the alkyl sulfosuccinate monoesters of the formulae (I) and (II);
and at least one active antiperspirant/deodorant ingredient.

In a preferred embodiment of the invention, this mixture comprises at least 60% by weight, preferably at least 70% by weight, especially at least 80% by weight, of C16- and C18-alkyl sulfosuccinate monoesters based on the sum of the alkyl sulfosuccinate monoesters of the formulae (I) and (II).

According to the invention, suitable active antiperspirant/deodorant ingredients are all active ingredients which counteract, mask or eliminate body odors. Body odors arise as a result of the action of skin bacteria on apocrine perspiration, which forms unpleasant-smelling degradation products. Suitable active antiperspirant/deodorant ingredients are especially compounds selected from the group consisting of antiperspirants, esterase inhibitors, bactericidal or bacteriostatic active ingredients and/or perspiration-absorbing substances.

Antiperspirants

Antiperspirants are salts of aluminum, of zirconium or of zinc. Such suitable antihydrotic active ingredients are, for example, aluminum chloride, aluminum chlorohydrate, aluminum dichlorohydrate, aluminum sesquichlorohydrate and complexes thereof, for example with 1,2-propylene glycol, aluminum hydroxy-allantoinate, aluminum chloride tartrate, aluminum zirconium trichlorohydrate, aluminum zirconium tetrachlorohydrate, aluminum zirconium penta-chlorohydrate and complexes thereof, for example with amino acids such as glycine. Preference is given to using aluminum chlorohydrate, aluminum zirconium tetrachlorohydrate, aluminum zirconium pentachloro-hydrate and complexes thereof.

The inventive formulations may comprise the antiperspirants in amounts of 1 to 50%, preferably 5 to 30% and especially 8 to 25% by weight—based on the total weight of the cosmetic and/or pharmaceutical formulation.

Esterase Inhibitors

In the presence of perspiration in the underarm region, bacteria form extracellular enzymes—esterases, preferably proteases and/or lipases—which cleave esters present in the perspiration and thus release odorants. Suitable esterase inhibitors are preferably trialkyl citrates such as trimethyl citrate, tripropyl citrate, triisopropyl citrate, tributyl citrate and especially triethyl citrate (Hydagen® CAT, Cognis GmbH, Dusseldorf/FRG). The substances inhibit enzyme activity and hence reduce odor formation. Further substances which are possible esterase inhibitors are sterol sulfates or phosphates, for example sulfates or phosphates of lanosterol, of cholesterol, of campesterol, of stigmasterol and of sitosterol, dicarboxylic acids and esters thereof, for example glutaric acid, monoethyl glutarate, diethyl glutarate, adipic acid, monoethyl adipate, diethyl adipate, malonic acid and diethyl malonate, hydroxycarboxylic acids and esters thereof, for example citric acid, malic acid, tartaric acid or diethyl tartrate, and zinc glycinate.

The inventive formulations may comprise the esterase inhibitors in amounts of 0.01 to 20%, preferably 0.1 to 10% and especially 0.3 to 5% by weight—based on the total weight of the cosmetic and/or pharmaceutical formulation.

Bactericidal or Bacteriostatic Active Ingredients

Typical examples of suitable bactericidal or bacteriostatic active ingredients are especially chitosan and phenoxyethanol. 5-Chloro-2-(2,4-dichloro-phenoxy)phenol has also been found to be particularly effective, and is sold under the Irgasan® brand by Ciba-Geigy, Basle, Switzerland. Suitable germicides are in principle all substances which act against Gram-positive bacteria, for example 4-hydroxybenzoic acid and the salts and esters thereof, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynylbutyl carbamate, chlorhexidine, 3,4,4'-trichlorocarbanilide (TTC), antibacterial odorants, thymol, thyme oil, eugenol, clove oil, menthol, mint oil, farnesol, phenoxyethanol, glyceryl monocaprate, glyceryl monocaprylate, glyceryl monolaurate (GML), diglyceryl monocaprate (DMC), and N-alkylsalicylamides, for example n-octylsalicylamide or n-decylsalicylamide.

The inventive formulations may comprise the bactericidal or bacteriostatic active ingredients in amounts of 0.01 to 5% and preferably 0.1 to 2% by weight—based on the total weight of the cosmetic and/or pharmaceutical formulation.

Perspiration-Absorbing Substances

Useful perspiration-absorbing substances include modified starches, for example Dry Flo Plus (from National Starch), silicates, talc and other substances of similar polymorphism, which appear suitable for absorption of perspiration. The inventive formulations may comprise the perspiration-absorbing substances in amounts of 0.1 to 30%, preferably 1 to 20% and especially 2 to 8% by weight—based on the total weight of the cosmetic and/or pharmaceutical formulation.

The invention provides cosmetic and/or pharmaceutical formulations comprising, in a cosmetically and/or pharmaceutically suitable carrier, 0.1 to 50% by weight, preferably 0.5 to 10% by weight, based on the formulation, of a mixture of alkyl sulfosuccinate monoesters of the general formula (I) and/or (II)

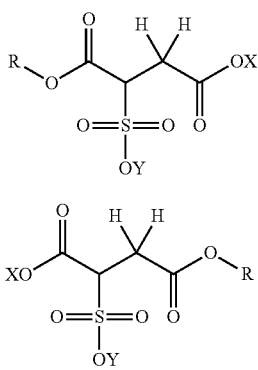

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and 30 to 70% by weight of C18-alkyl sulfosuccinate monoester, where the percentages by weight are based on the total amount of the alkyl sulfosuccinate monoesters of the formulae (I) and (II), and at least one self-tanning agent.

The invention further provides cosmetic and/or pharmaceutical formulations comprising, in a cosmetically and/or pharmaceutically suitable carrier, 0.1 to 50% by weight, preferably 0.5 to 10% by weight, based on the formulation, of a mixture of alkyl sulfosuccinate monoesters of the general formula (I) and/or (II)

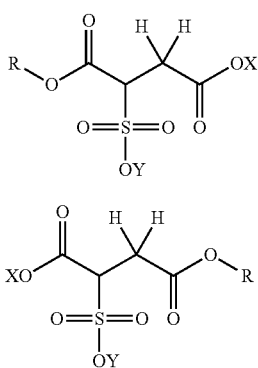

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and 30 to 70% by weight of C18-alkyl sulfosuccinate monoester, where the percentages by weight are based on the total amount of the C16- and C18-alkyl sulfosuccinate monoesters present in the mixture of the formulae (I) and (II), and where the mixture comprises at least 50% by weight of C16- and C18-alkyl sulfosuccinate monoesters based on the sum of the alkyl sulfosuccinate monoesters of the formulae (I) and (II);

and at least one self-tanning agent.

In a preferred embodiment of the invention, this mixture comprises at least 60% by weight, preferably at least 70% by weight, especially at least 80% by weight, of C16- and C18-alkyl sulfosuccinate monoesters based on the sum of the alkyl sulfosuccinate monoesters of the formulae (I) and (II).

Self-tanning agents are understood to mean substances which cause browning of the skin. Examples include alpha, beta-unsaturated aldehydes, which react with the amino acids in the skin in the manner of a Maillard reaction to give colored compounds. Useful active ingredients for self-tanning agents also include natural or synthetic ketols or aldols. Examples of suitable active ingredients include dihydroxyacetone, erythrulose, glyceroaldehyde, alloxan, hydroxymethylglyoxal, gamma-dialdehyde, 6-aldo-D-fructose, ninhydrin and meso-tartaraldehyde. Suitable self-tanning agents are especially dihydroxyacetone and/or erythrulose.

Mixtures of the abovementioned active ingredients with one another or with muconaldehyde and/or naphthoquinones, for example 5-hydroxy-1,4-naphthoquinone (juglone) and 2-hydroxy-1,4-naphthoquinone, have been found to be particularly advantageous.

The inventive formulations comprise the self-tanning agents typically in concentrations of 1 to 10% and especially of 2 to 5% by weight—based on the total weight of the cosmetic and/or pharmaceutical formulation.

In a preferred embodiment of the invention, the inventive cosmetic and/or pharmaceutical formulations comprise at least one self-tanning agent and at least one UV photoprotective filter.

The invention provides cosmetic and/or pharmaceutical formulations comprising, in a cosmetically and/or pharmaceutically suitable carrier, 0.1 to 50% by weight, preferably 0.5 to 10% by weight, based on the formulation, of a mixture of alkyl sulfosuccinate monoesters of the general formula (I) and/or (II)

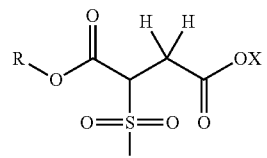

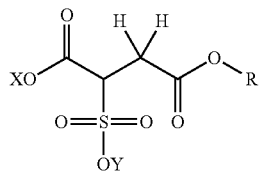

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and 30 to 70% by weight of C18-alkyl sulfosuccinate monoester, where the percentages by weight are based on the total amount of the alkyl sulfosuccinate monoesters of the formulae (I) and (II), and at least one pigment and/or a dye.

The invention further provides cosmetic and/or pharmaceutical formulations comprising, in a cosmetically and/or pharmaceutically suitable carrier, 0.1 to 50% by weight, preferably 0.5 to 10% by weight, based on the formulation, of a mixture of alkyl sulfosuccinate monoesters of the general formula (I) and/or (II)

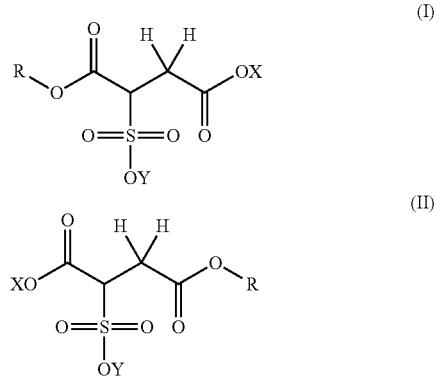

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and 30 to 70% by weight of C18-alkyl sulfosuccinate monoester, where the percentages by weight are based on the total amount of the C16- and C18-alkyl sulfosuccinate monoesters present in the mixture of the formulae (I) and (II), and where the mixture comprises at least 50% by weight of C16- and C18-alkyl sulfosuccinate monoesters based on the sum of the alkyl sulfosuccinate monoesters of the formulae (I) and (II), and at least one pigment and/or a dye.

In a preferred embodiment of the invention, this mixture comprises at least 60% by weight, preferably at least 70% by weight, especially at least 80% by weight, of C16- and C18-alkyl sulfosuccinate monoesters based on the sum of the alkyl sulfosuccinate monoesters of the formulae (I) and (II).

The term pigment encompasses particles of any kind which are white or colored, organic or inorganic, are insoluble in the formulations, and serve the purpose of coloring the formulation. In a preferred embodiment, inorganic pigments are used, particular preference being given to metal oxides.

Examples of inorganic pigments include: titanium dioxide, optionally surface-coated, zirconium or cerium oxides, and zinc, iron (black, yellow or red) and chromium oxides, manganese violet, ultramarine blue, chromium hydrates and iron(III) blue, and metal powders such as aluminum powder or copper powder.

In a preferred embodiment of the invention, the pigment is selected from the inorganic pigments, preferably from the metal oxides. In a preferred embodiment, the pigment is selected from the group consisting of titanium dioxide, zinc oxide, iron oxide and mixtures thereof.

The pigments may be present either individually or in mixtures.

Preference is given in the context of the present invention to pigment mixtures composed of white pigments (e.g. kaolin, titanium dioxide or zinc oxide) and inorganic color pigments (e.g. iron oxide pigments, chromium oxides), and the pigments may be present in coated or uncoated form. Among the color pigments, iron oxides are particularly preferred.

Advantageously in the context of the present invention, the pigment(s) may also be selected from the group of the effect pigments which impart to the cosmetic formulation, in addition to the pure color, an additional property—for example angular dependence of the color (flop), luster (not surface luster) or texture. Such effect pigments are used in accordance with the invention advantageously in addition to one or more white and/or color pigments.

The most important group of the effect pigments is that of the luster pigments, which, according to DIN 55944: 2003-11, include the metal effect pigments and the pearlescent pigments. Some specific effect pigments cannot be assigned to these two groups, for example graphite platelets, iron oxide platelets and micronized titanium dioxide, the latter not giving a luster effect, but rather an angle-dependent light-scattering effect. The luster pigments to DIN 55943: 2001-10 are predominantly effect pigment platelets. Aligned in parallel, luster pigments exhibit a characteristic luster. The visual effect of luster pigments is based on the directed reflection on metallic particles (metal effect pigments), on transparent particles with a high refractive index (pearlescent pigments) or on the phenomenon of interference (interference pigments) (DIN 55944: 2003-11).

Examples of commercial effect pigments preferred in accordance with the invention are: Timiron and #174; from Merck, Iriodin and #174; from Merck (pearlescent and color luster pigments for decorative industrial applications), Xirallic and #174; from Merck (intense-color crystal effect pigments).

In addition, the inventive formulations may advantageously also comprise organic color pigments, i.e. organic dyes which are virtually insoluble in the formulation. According to DIN 55944: 1990-04, organic pigments can be divided according to chemical aspects into azo pigments and polycyclic pigments, and according to color aspects into chromatic or black pigments.

In the context of the present invention, the pigments can advantageously also be employed in the form of commercially available oily or aqueous predispersions.

The inventive formulations comprise typically 0.1 to 40% by weight of pigments—based on the total weight of the cosmetic and/or pharmaceutical formulation.

It is also advantageous in the context of the present invention when the inventive formulation comprises one or more dyes.

The dyes may be either of synthetic or natural origin. A list of suitable dyes can be found in EP 1 371 359 A2, page 8, lines 25-57, page 9 and page 10, and also page 11, lines 1 to 54, to which reference is hereby explicitly made.

The inventive formulations comprise typically 0.01 to 5% and preferably 0.1 to 1.0% by weight of dyes—based on the total weight of the cosmetic and/or pharmaceutical formulation. The inventive formulations typically comprise a total amount of dyes and pigments in the range from 0.01 to 30% by weight, especially 0.1 to 15% by weight, preferably 1 to 10% by weight, based on the total weight of the cosmetic and/or pharmaceutical formulation.

Suitable dyes and pigments are especially the dyes and pigments approved according to Annex IV of the Commission Directive (in the version: Commission Directive 2007/22/EC of 17 Apr. 2007 amending Council Directive 76/768/EEC, concerning cosmetic products, for the purposes of adapting Annexes IV and VI thereto to technical progress) approved substances, to which reference is hereby explicitly made.

The invention provides cosmetic and/or pharmaceutical formulations comprising, in a cosmetically and/or pharmaceutically suitable carrier, 0.1 to 50% by weight, preferably 0.5 to 10% by weight, based on the formulation, of a mixture of alkyl sulfosuccinate monoesters of the general formula (I) and/or (II)

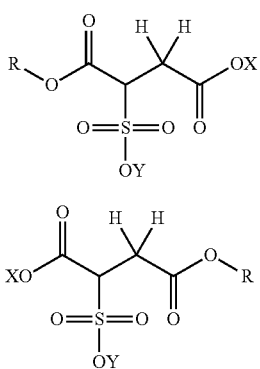

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and 30 to 70% by weight of C18-alkyl sulfosuccinate monoester, where the percentages by weight are based on the total amount of the alkyl sulfosuccinate monoesters of the formulae (I) and (II), and at least one (further) interface-active substance and/or a wax component and/or a polymer and/or an oily substance.

The invention further provides cosmetic and/or pharmaceutical formulations comprising, in a cosmetically and/or pharmaceutically suitable carrier, 0.1 to 50% by weight, preferably 0.5 to 10% by weight, based on the formulation, of a mixture of alkyl sulfosuccinate monoesters of the general formula (I) and/or (II)

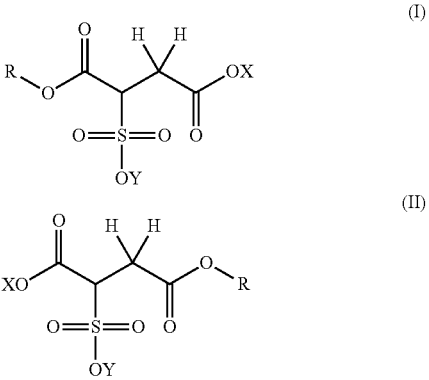

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and 30 to 70% by weight of C18-alkyl sulfosuccinate monoester, where the percentages by weight are based on the total amount of the C16- and C18-alkyl sulfosuccinate monoesters present in the mixture of the formulae (I) and (II), and where the mixture comprises at least 50% by weight of C16- and C18-alkyl sulfosuccinate monoesters based on the sum of the alkyl sulfosuccinate monoesters of the formulae (I) and (II);

and at least one (further) interface-active substance and/or a wax component and/or a polymer and/or an oily substance.

In a preferred embodiment of the invention, this mixture comprises at least 60% by weight, preferably at least 70% by weight, especially at least 80% by weight, of C16- and C18-alkyl sulfosuccinate monoesters based on the sum of the alkyl sulfosuccinate monoesters of the formulae (I) and (II).

Interface-Active Substance

In one embodiment of the invention, the inventive cosmetic and/or pharmaceutical formulations comprise at least one interface-active substance. The inventive formulations comprise the interface-active substance(s) [without the inventive alkyl sulfosuccinate mixtures] in an amount of 0 to 80% by weight, especially 0 to 40% by weight, preferably 0.1 to 20% by weight, preferably 0.1 to 15% by weight and especially 0.1 to 10% by weight, based on the total weight of the formulation.

A suitable interface-active substance is in principle any substance which lowers the surface tension between the aqueous and nonaqueous phases. Interface-active substances include emulsifiers and surfactants.

When the inventive cosmetic and/or pharmaceutical formulation comprises the inventive alkyl sulfosuccinate mixture as an interface-active substance, this claim relates to the presence of a further interface-active substance.

In one embodiment of the invention, the inventive formulation comprises more than one interface-active substance. The person skilled in the art uses customary systems (for example emulsifier and coemulsifier) depending on the other components.

A suitable emulsifier is in principle any interface-active substance, but especially substances with an HLB value of 1 to 20 by the Griffin scale. The Griffin scale is described in W C Griffin, J. Soc. Cosmet. Chem. (1949) 311; W C Griffin, J. Soc. Cosmet. Chem. 5 (1954) 249. Every emulsifier is assigned what is called an HLB value (a dimensionless number between 1 and 20, Griffin scale), which reports whether preferential water or oil solubility is present. Numbers below 9 indicate preferentially oil-soluble, hydrophobic emulsifiers, numbers above 11 water-soluble, hydrophilic emulsifiers. The HLB value makes a statement about the equilibrium of the size and strength of the hydrophilic and lipophilic groups of an emulsifier.

The solubility of the emulsifier in the two phases effectively determines the emulsion type. When the emulsifier has better water solubility, an O/W emulsion is obtained. When the emulsifier, in contrast, has a better solubility in the oil phase, a W/O emulsion forms under otherwise identical production conditions.

Nonionic Emulsifiers

The group of nonionic emulsifiers includes, for example:
(1) Addition products of 2 to 50 mol of ethylene oxide and/or 1 to 20 mol of propylene oxide onto linear fatty alcohols having 8 to 40 carbon atoms, onto fatty acids having 12 to 40 carbon atoms and onto alkylphenols having 8 to 15 carbon atoms in the alkyl group.
(2) $C_{12}$-$C_{18}$ fatty acid mono- and diesters of addition products of 1 to 50 mol of ethylene oxide onto glycerol.
(3) Sorbitan mono- and diesters of saturated and unsaturated fatty acids having 6 to 22 carbon atoms and ethylene oxide addition products thereof.
(4) Alkyl mono- and oligoglycosides having 8 to 22 carbon atoms in the alkyl radical and ethoxylated analogs thereof.
(5) Addition products of 7 to 60 mol of ethylene oxide onto castor oil and/or hydrogenated castor oil.
(6) Polyol and especially polyglyceryl esters, for example polyol poly-12-hydroxystearates, polyglyceryl polyricinoleate, polyglyceryl diisostearate or polyglyceryl dimerate. Likewise suitable are mixtures of compounds of two or more of these substance classes.
(7) Addition products of 2 to 15 mol of ethylene oxide onto castor oil and/or hydrogenated castor oil.
(8) Partial esters based on linear, branched, unsaturated or saturated $C_6$-$C_{22}$-fatty acids, ricinoleic acid and 12-hydroxystearic acid and polyglycerol, pentaerythritol, dipentaerythritol, sugar alcohols (e.g. sorbitol), alkyl glucosides (e.g. methyl glucoside, butyl glucoside, lauryl glucoside) and polyglucosides (e.g. cellulose), or mixed esters, for example glyceryl stearate lactate.
(9) Polysiloxane-polyalkyl-polyether copolymers and corresponding derivatives.
(10) Mixed esters of pentaerythritol, fatty acids, citric acid and fatty alcohol and/or mixed esters of fatty acids having 6 to 22 carbon atoms, methylglucose and polyols, preferably glycerol or polyglycerol.

The addition products of ethylene oxide and/or of propylene oxide onto fatty alcohols, fatty acids, alkylphenols, glyceryl mono- and diesters and also sorbitan mono- and diesters of fatty acids or onto castor oil are known, commercially available products. These are homolog mixtures whose mean degree of alkoxylation corresponds to the ratio of the amounts of ethylene oxide and/or propylene oxide and substrate with which the addition reaction is carried out. Depending on the degree of ethoxylation, they are W/O or O/W emulsifiers. $C_{12/18}$ fatty acid mono- and diesters of addition products of ethylene oxide onto glycerol are known as refatting agents for cosmetic formulations.

Mild emulsifiers which are particularly suitable in accordance with the invention are polyol poly-12-hydroxystearates and mixtures thereof, which are sold, for example, under the "Dehymuls® PGPH" (W/O emulsifier) or "Eumulgin® VL 75" (blend with Lauryl Glucosides in a weight ratio of 1:1, O/W emulsifier) or Dehymuls® SBL (W/O emulsifier) brands by Cognis Deutschland GmbH. In this connection, reference may be made especially to European patent EP 766 661 B1. The polyol component of these emulsifiers may derive from substances which have at least two, preferably 3 to 12 and especially 3 to 8 hydroxyl groups and 2 to 12 carbon atoms.

Particularly preferred emulsifiers are, for example, Cetyl Dimethicone Copolyol (e.g. Abil EM-90), Polyglyceryl-2 Dipolyhydroxystearate (e.g. Dehymuls PGPH), Polyglyceryl-3 Diisostearate (e.g. Lameform TGI), Polyglyceryl-4 Isostearate (e.g. Isolan GI 34), Polyglyceryl-3 Oleate (e.g. Isolan GO 33), Diisostearoyl Polyglyceryl-3 Diisostearate (e.g. Isolan PDI), Polyglyceryl-3 Methylglucose Distearate (e.g. Tego Care 450), Polyglyceryl-3 Beeswax (e.g. Cera Bellina), Polyglyceryl-4 Caprate (e.g. Polyglycerol Caprate T2010/90), Polyglyceryl-3 Cetyl Ether (e.g. Chimexane NL), Polyglyceryl-3 Distearate (e.g. Cremophor GS 32) and Polyglyceryl Polyricinoleate (e.g. Admul WOL 1403), Glyceryl Oleate (e.g. Monomuls 90-O 18), Alkyl Glucoside (e.g. Plantacare 1200, Emulgade PL 68/50, Montanov 68, Tego Care CG 90, Tego Glucosid L 55), Methyl Glucose Isostearate (e.g. Tego Care IS), Methyl Glucose Sesquistearate (Tego Care PS), Sodium Cocoyl Hydrolyzed Wheat Protein (e.g. Gluadin WK), Potassium Cetyl Phosphate (e.g. Amphisol K, Crodafos CKP), Sodium Alkylsulfate (e.g. Lanette E), Sucrose Ester (e.g. Crodesta F-10, F-20, F-50, F-70, F-110, F-160, SL-40, Emulgade® Sucro), ethoxylated and/or propoxylated fatty alcohols, fatty acids, castor oils and hydrogenated castor oils (e.g. Eumulgin B2, B2, B3, L, HRE 40, HRE 60, RO 40, Cremophor HRE 40, HRE 60, L, WO 7, Dehymuls HRE 7, Arlacel 989), PEG-30 Dipolyhydroxystearate (e.g. Arlacel P 135, Dehymuls LE), sorbitan esters, sorbitan esters ethoxylated and/or propoxylated, and mixtures thereof. A particularly effective mixture consists of Polyglyceryl-2 Dipolyhydroxystearate and Lauryl Glucoside and glycerol (e.g. Eumulgin VL 75). Also suitable are Polyglyceryl-4 Diisostearate/Polyhydroxy-stearate/Sebacate (Isolan® GPS), Diisostearoyl Polyglyceryl-3 Diisostearate (e.g. Isolan PDI), and alkali metal acylglutamates (e.g. Eumulgin SG).

Suitable lipophilic W/O emulsifiers are in principle emulsifiers with an HLB value of 1 to 8, which are summarized in numerous tabular works and are known to the person skilled in the art. Some of these emulsifiers are listed, for example, in Kirk-Othmer, "Encyclopedia of Chemical Technology", 3rd edition, 1979, volume 8, page 913. For ethoxylated products, the HLB value can also be calculated according to the following formula: HLB=(100−L):5, where L is the weight fraction of the lipophilic groups, i.e. of the fatty alkyl or fatty acyl groups in percent by weight, in the ethylene oxide adducts.

Particularly advantageous from the group of W/O emulsifiers are partial esters of polyols, especially of $C_4$-$C_6$-polyols, for example partial esters of pentaerythritol or sugar esters, e.g. sucrose distearate, sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical-grade mixtures thereof. Also suitable as emulsifiers are addition products of 1 to 30 and preferably 5 to 10 mol of ethylene oxide onto the specified sorbitan esters.

Depending on the formulation, it may be advantageous to additionally use at least one emulsifier from the group of nonionic O/W emulsifiers (HLB value: 8-18) and/or solubilizers. These are, for example, the ethylene oxide adducts already mentioned in the introduction and having a correspondingly high degree of ethoxylation, e.g. 10-20 ethylene oxide units for O/W emulsifiers and 20-40 ethylene oxide units for solubilizers. According to the invention, Ceteareth-12 and PEG-20 Stearate are particularly advantageous as O/W emulsifiers. Preferentially suitable solubilizers are Eumulgin® HRE 40 (INCI: PEG-40 Hydrogenated Castor Oil), Eumulgin®HRE 60 (INCI: PEG-60 Hydrogenated Castor Oil), Eumulgin® L (INCI: PPG-1-PEG-9 Lauryl Glycol Ether), and Eumulgin® SML 20 (INCI: Polysorbate-20).

Nonionic emulsifiers from the group of alkyl oligoglycosides are particularly skin-friendly and therefore preferentially suitable as O/W emulsifiers. $C_8$-$C_{22}$-alkyl mono- and oligoglycosides, their preparation and their use are known from the prior art. Their preparation takes place especially by reacting glucose or oligosaccharides with primary alcohols having 8 to 22 carbon atoms. As regards the glycoside radical, either monoglycosides, in which a cyclic sugar radical is glycosidically bonded to the fatty alcohol, or oligomeric glycosides with a degree of oligomerization up to preferably about 8 are suitable. The degree of oligomerization here is a statistical average based on a homolog distribution customary for such technical-grade products. Products which are available under the name Plantacare® comprise a glucosidically bonded $C_8$-$C_{16}$-alkyl group onto an oligoglucoside radical whose average degree of oligomerization is 1 to 2. The acylglucamides derived from glucamine are also suitable as nonionic emulsifiers. According to the invention, preference is given to a product which is sold under the name Emulgade® PL 68/50 by Cognis Deutschland GmbH and is a 1:1 mixture of alkyl polyglucosides and fatty alcohols. According to the invention, it is also advantageously possible to use a mixture of Lauryl Glucoside, Polyglyceryl-2 Dipolyhydroxystearate, glycerol and water, which is commercially available under the name Eumulgin® VL 75.

Also suitable as emulsifiers are substances such as lecithins and phospholipids. Examples of natural lecithins which may be mentioned are the cephalins, which are also referred to as phosphatidic acids and are derivatives of 1,2-diacyl-sn-glycerol-3-phosphoric acids. By contrast, phospholipids are usually understood to mean mono- and preferably diesters of phosphoric acid with glycerol (glycerol phosphates), which are generally included in the fats. In addition, sphingosines and sphingolipids are also suitable.

The emulsifiers present may, for example, be silicone emulsifiers. These may be selected, for example, from the group of alkylmethicone copolyols and/or alkyldimethicone copolyols, especially from the group of compounds which are characterized by the following chemical structure:

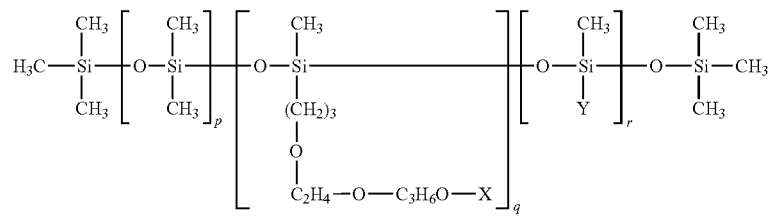

in which X and Y are each independently selected from the group of H (hydrogen) and the branched and unbranched alkyl groups, acyl groups and alkoxy groups having 1-24 carbon atoms, p is 0-200, q is 1-40, and r is 1-100.

One example of silicone emulsifiers to be used particularly advantageously within the context of the present invention is that of dimethicone copolyols, which are sold by Evonik Goldschmidt under the trade names AXIL® B 8842, ABIL® B 8843, ABIL® B 8847, ABIL® B 8851, ABIL® B 8852, ABIL® B 8863, ABIL® B 8873 and ABIL® B 88183.

A further example of interface-active substances to be used particularly advantageously within the context of the present invention is that of cetyl PEG/PPG-10/1 dimethicone (cetyl dimethicone copolyol), which is sold by Evonik Goldschmidt under the trade name ABIL® EM 90.

A further example of interface-active substances to be used particularly advantageously within the context of the present invention is that of cyclomethicone dimethicone copolyol, which is sold by Evonik Goldschmidt under the trade name ABIL® EM 97 and ABIL® WE 09.

In addition, the emulsifier lauryl PEG/PPG-18/18 methicone (laurylmethicone copolyol) has been found to be very particularly advantageous and is available under the trade name Dow Corning® 5200 Formulation Aid from Dow Corning Ltd. A further advantageous silicone emulsifier is octyl dimethicone ethoxy glucoside from Wacker.

For an inventive water-in-silicone oil emulsion, all known emulsifiers used for this type of emulsion can be used. Water-in-silicone emulsifiers which are particularly preferred in accordance with the invention are Cetyl PEG/PPG-10/1 Dimethicone and Lauryl PEG/PPG-18/18 Methicone [e.g. ABIL® EM 90 (Evonik Goldschmidt), DC5200 Formulation Aid (Dow Corning)] and any desired mixtures of the two emulsifiers.

In one embodiment of the invention, the inventive cosmetic and/or pharmaceutical formulation further comprises, as an interface-active substance, at least one surfactant.

The interface-active substances present may be anionic, nonionic, cationic and/or amphoteric or zwitterionic surfactants. In surfactant-comprising cosmetic formulations, for example shower gels, foam baths, shampoos, etc., at least one anionic surfactant is preferably present.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides and glucuronic acid derivatives, fatty acid N-alkylglucamides, protein hydrolyzates (especially wheat-based vegetable products), polyol fatty acid esters, sugar esters, sorbitan esters, polysorbates and amine oxides. If the nonionic surfactants comprise polyglycol ether chains, they may have a conventional homolog distribution, but preferably have a narrow homolog distribution.

Zwitterionic surfactants refer to those surface-active compounds which bear at least one quaternary ammonium group and at least one —COO$^{(-)}$ or —SO$_3^{(-)}$ group in the molecule. Particularly suitable zwitterionic surfactants are the betaines, such as the N-alkyl-N,N-dimethylammonium glycinates, for example cocoalkyl dimethylammonium glycinate, N-acylaminopropyl-N,N-dimethylammonium glycinates, for example cocoacylamino-propyldimethylammonium glycinate, and 2-alkyl-3-carboxymethyl-3-hydroxyethylimidazoline having in each case 8 to 18 carbon atoms in the alkyl or acyl group, and also cocoacylaminoethyl hydroxyethylcarboxymethyl glycinate. A preferred zwitterionic surfactant is the fatty acid amide derivative known under the INCI name Cocamidopropyl Betaine.

Likewise suitable, especially as cosurfactants, are ampholytic surfactants. Ampholytic surfactants are understood to mean those surface-active compounds which, apart from a $C_8$-$C_{18}$-alkyl or acyl group in the molecule, comprise at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropyl-glycines, N-alkyltaurines, N-alkylsarcosines, 2-alkyl-aminopropionic acids and alkylaminoacetic acids having in each case about 8 to 18 carbon atoms in the alkyl group. Particularly preferred ampholytic surfactants are N-cocoalkylaminopropionate, cocoacylaminoethyl-aminopropionate and $C_{12-18}$-acylsarcosine.

Typical examples of amphoteric or zwitterionic surfactants are alkylbetaines, alkylamidobetaines, aminopropionates, aminoglycinates, imidazolinium betaines and sulfobetaines. The specified surfactants are exclusively known compounds. With regard to the structure and preparation of these substances, reference may be made to relevant review works in this field. Typical examples of particularly suitable mild, i.e. particularly skin-friendly, surfactants are fatty alcohol polyglycol ether sulfates, monoglyceride sulfates, dialkyl sulfosuccinates, fatty acid isethionates, fatty acid sarcosinates, fatty acid taurides, fatty acid glutamates, α-olefinsulfonates, ether carboxylic acids, alkyl oligoglucosides and/or mixtures thereof with alkyl oligoglucoside carboxylates, fatty acid glucamides, alkylamidobetaines, amphoacetals and/or protein fatty acid condensates, the latter preferably based on wheat proteins or salts thereof.

Anionic surfactants are characterized by a water-solubilizing, anionic group, for example a carboxylate, sulfate, sulfonate or phosphate group and a lipophilic radical. Skin-compatible anionic surfactants are known to the person skilled in the art in a large number from relevant handbooks and are commercially available. These are especially alkyl sulfates in the form of their alkali metal, ammonium or alkanolammonium salts, alkyl ether sulfates, alkyl ether carboxylates, acyl isethionates, acyl sarcosinates, acyltaurines with linear alkyl or acyl groups having 12 to 18 carbon atoms, and also dialkyl sulfosuccinates and acyl glutamates in the form of their alkali metal or ammonium salts.

Typical examples of anionic surfactants are soaps, alkylbenzenesulfonates, alkanesulfonates, olefin-sulfonates, alkyl ether sulfonates, glycerol ether sulfonates, α-methyl ester sulfonates, sulfo fatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, dialkyl sulfosuccinates, mono- and dialkyl sulfosuccinamates, sulfotriglycerides, amide soaps, ethercarboxylic acids and salts thereof, fatty acid isethionates, fatty acid sarcosinates, fatty acid taurides, N-acylamino acids, for example acyl lactylates, acyl tartrates, acyl glutamates and acyl aspartates, alkyl oligoglucoside sulfates, protein fatty acid condensates (especially vegetable products based on wheat) and alkyl (ether) phosphates. If the anionic surfactants comprise polyglycol ether chains, these may have a conventional homolog distribution, but preferably have a narrow homolog distribution. A suitable anionic surfactant is, for example, Glyceryl Stearate Citrate.

Cationic surfactants which can be used are especially quaternary ammonium compounds. Preference is given to ammonium halides, especially chlorides and bromides, such as alkyltrimethylammonium chlorides, dialkyldimethylammonium chlorides and trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. In addition, the very readily biodegradable quaternary ester compounds, for example the dialkylammonium methosulfates and methylhydroxyalkyldialkyloxyalkylammonium methosulfates sold under the trade name Stepantex® and the corresponding products of the Dehyquart® series, can be used as cationic surfactants. The term "ester quats" is generally understood to mean quaternized fatty acid triethanolamine ester salts. They can impart an exceptional soft feel to the preparations according to the invention. These are known substances which are prepared by the relevant methods of organic chemistry. Further cationic surfactants which can be used in accordance with the invention are the quaternized protein hydrolyzates.

In one embodiment of the invention, the inventive cosmetic and/or pharmaceutical formulation further comprises at least one wax component.

The inventive formulations comprise the wax component (s) typically in an amount of 0 to 40% by weight, especially of 0 to 20% by weight, preferably 0.1 to 15% by weight and especially 0.1 to 10% by weight, based on the total weight of the formulation.

The term "wax" is typically understood to mean all natural or synthetic substances and substance mixtures having the following properties: they are of solid to brittle and hard consistency, coarse to finely crystalline, transparent to cloudy and melt above 30° C. without decomposition. They are low in viscosity even a little above the melting point and do not string, and exhibit a strongly temperature-dependent consistency and solubility. According to the invention, it is possible to use a wax component or a mixture of wax components which melt at 30° C. or higher.

The waxes used in accordance with the invention may also be fats and fat-like substances with waxy consistency, provided they have the required melting point. These include, inter alia, fats (triglycerides), mono- and diglycerides, natural and synthetic waxes, fatty and wax alcohols, fatty acids, esters of fatty alcohols and fatty acids and also fatty acid amides or any desired mixtures of these substances.

Fats are understood to mean triacylglycerols, i.e. the triple esters of fatty acids with glycerol. They preferably comprise saturated, unbranched and unsubstituted fatty acid radicals. They may also be mixed esters, i.e. triple esters of glycerol with different fatty acids. According to the invention, it is possible to use hydrogenated fats and oils, which are obtained by partial hydrogenation and are particularly suitable as consistency regulators. Vegetable hydrogenated fats and oils are preferred, e.g. hydrogenated castor oil, peanut oil, soybean oil, rapeseed oil, colza oil, cottonseed oil, soybean oil, sunflower oil, palm oil, palm kernel oil, linseed oil, almond oil, corn oil, olive oil, sesame oil, cocoa butter and coconut fat.

Suitable examples include the triple esters of glycerol with C12-C60-fatty acids and especially C12-C36-fatty acids. These include hydrogenated castor oil, a triple ester of glycerol and a hydroxystearic acid, which is commercially available, for example, under the Cutina HR name. Glyceryl tristearate, glyceryl tribehenate (e.g. Syncrowax HRC), glyceryl tripalmitate or the triglyceride mixtures known under the Syncrowax HGLC name are likewise suitable, with the proviso that the melting point of the wax component or of the mixture is 30° C. or higher.

According to the invention, usable wax components are especially mono- and diglycerides and mixtures of these partial glycerides. Glyceride mixtures which can be used in accordance with the invention include the Novata AB and Novata B (mixture of C12-C18-mono-, di- and triglycerides) and Cutina MD or Cutina GMS (glyceryl stearate) products sold by Cognis Deutschland GmbH & Co. KG.

Fatty alcohols which can be used in accordance with the invention as the wax component include the C12-C50-fatty alcohols. The fatty alcohols can be obtained from natural fats, oils and waxes, for example myristyl alcohol, 1-pentadecanol, cetyl alcohol, 1-heptadecanol, stearyl alcohol, 1-nonadecanol, arachidyl alcohol, 1-heneicosanol, behenyl alcohol, brassidyl alcohol, lignoceryl alcohol, ceryl alcohol or myricyl alcohol. Preference is given in accordance with the invention to saturated unbranched fatty alcohols. However, it is also possible in accordance with the invention to use unsaturated, branched or unbranched fatty alcohols as the wax component, provided they have the required melting point. It is also possible in accordance with the invention to use fatty alcohol cuts, as produced in the reduction of naturally occurring fats and oils, for example bovine tallow, peanut oil, colza oil, cottonseed oil, soybean oil, sunflower oil, palm kernel oil, linseed oil, castor oil, corn oil, rapeseed oil, sesame oil, cocoa butter and coconut fat. However, it is also possible to use synthetic alcohols, e.g. the linear, even-numbered fatty alcohols from the Ziegler synthesis (alfols) or the partially branched alcohols from the oxo process (dobanols). Particular preference is given in accordance with the invention to C14-C22-fatty alcohols, which are sold, for example, by Cognis Deutschland GmbH under the Lanette 18 (C18-alcohol), Lanette 16 (C16-alcohol), Lanette 14 (C14-alcohol), Lanette O (C16/C18-alcohol) and Lanette 22 (C18/C22-alcohol) names. Fatty alcohols impart a drier skinfeel to the formulations than triglycerides and are therefore preferred over the latter.

The wax components used may also be C14-C40-fatty acids or mixtures thereof. These include, for example, myristic acid, pentadecanoic acid, palmitic acid, margaric acid, stearic acid, nonadecanoic acid, arachic acid, behenic acid, lignoceric acid, cerotic acid, melissic acid, erucic acid and elaeostearic acid, and also substituted fatty acids, for example 12-hydroxystearic acid, and the amides or monoethanolamides of the fatty acids, this list being illustrative and nonlimiting in character.

It is possible in accordance with the invention to use, for example, natural vegetable waxes, such as candelilla wax, carnauba wax, japan wax, esparto grass wax, cork wax, guaruma wax, rice germ wax, sugarcane wax, ouricury wax, montan wax, sunflower wax, fruit waxes such as orange waxes, lemon waxes, grapefruit wax, bayberry wax, and animal waxes, for example beeswax, shellac wax, spermaceti, wool wax and uropygial grease. In the context of the invention, it may be advantageous to use hydrogenated or hardened waxes. The natural waxes which can be used in accordance with the invention also include mineral waxes, for example ceresin and ozokerite or the petrochemical waxes, for example petrolatum, paraffin waxes and microwaxes. Usable wax components also include chemically modified waxes, especially the hard waxes, for example montan ester waxes, sasol waxes and hydrogenated jojoba waxes. Synthetic waxes which can be used in accordance with the invention include, for example, wax-like polyalkylene waxes and polyethylene glycol waxes. Vegetable waxes are preferred in accordance with the invention.

The wax component can likewise be selected from the group of the wax esters of saturated and/or unsaturated, branched and/or unbranched alkanecarboxylic acids and saturated and/or unsaturated, branched and/or unbranched alcohols, from the group of esters of aromatic carboxylic acids, dicarboxylic acids, tricarboxylic acids and hydroxycarboxylic acids (e.g. 12-hydroxystearic acid) and saturated and/or unsaturated, branched and/or unbranched alcohols, and also from the group of lactides of long-chain hydroxycarboxylic acids. Examples of such esters are the C16-C40-alkyl stearates, C20-C40-alkyl stearates (e.g. Kesterwachs K82H), C20-C40-dialkyl esters of dimeric acids, C18-C38-alkylhydroxystearoyl stearates or C20-C40-alkyl erucates. It is also possible to use C30-C50-alkylbeeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetyl ester, cetearyl behenate and behenyl behenate. Fatty acid partial glycerides, i.e. technical-grade mono- and/or diesters of glycerol with fatty acids having 12 to 18 carbon atoms, for example glycerol mono/dilaurate, -palmitate, -myristate or -stearate, are also useful for this purpose.

Suitable waxes are additionally pearlescent waxes. Useful pearlescent waxes, especially for use in surface-active formulations, are, for example: alkylene glycol esters, especially ethylene glycol distearate; fatty acid alkanolamides, especially coconut fatty acid diethanolamide; partial glycerides, especially stearic acid monoglyceride; esters of polybasic, optionally hydroxy-substituted carboxylic acids with fatty alcohols having 6 to 22 carbon atoms, especially long-chain esters of tartaric acid; fatty substances, for example fatty alcohols, fatty ketones, fatty aldehydes, fatty ethers and fatty carbonates, which have a total of at least 24 carbon atoms, especially laurone and distearyl ethers; fatty acids such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Polymers

In one embodiment of the invention, the inventive cosmetic and/or pharmaceutical formulation further comprises at least one polymer.

The inventive formulations comprise the polymer(s) typically in an amount of 0 to 20% by weight, preferably 0.1 to 15% by weight and especially 0.1 to 10% by weight, based on the total weight of the formulation.

Suitable cationic polymers are, for example, cationic cellulose derivatives, for example a quaternized hydroxyethylcellulose, which is available under the Polymer JR 400® name from Amerchol, cationic starch, copolymers of diallylammonium salts and acrylamides, quaternized vinylpyrrolidone/vinylimidazole polymers, for example Luviquat® (BASF), condensation products of polyglycols and amines, quaternized collagen polypeptides, for example lauryldimonium hydroxypropyl hydrolyzed collagen (Lamequat®L/Grunau), quaternized wheat polypeptides, polyethyleneimine, cationic silicone polymers, for example amidomethicones, copolymers of adipic acid and dimethylaminohydroxypropyldiethylenetriamine (Cartaretine®/Sandoz), copolymers of acrylic acid with dimethyldiallylammonium chloride (Merquat® 550/Chemviron), polyaminopolyamides, cationic chitin derivatives, for example quaternized chitosan, optionally in microcrystalline distribution, condensation products of dihaloalkylene, for example dibromobutane with bisdialkylamines, for example bisdimethylamino-1,3-propane, cationic guar gum, for example Jaguar® CBS, Jaguar® C-17, Jaguar® C-16 from Celanese, and quaternized ammonium salt polymers, for example Mirapol® A-15, Mirapol® AD-1, Mirapol® AZ-1 from Miranol.

Useful anionic, zwitterionic, amphoteric and nonionic polymers are, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyltrimethylammonium chloride/acrylate copolymers, octylacrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinylcaprolactam terpolymers and optionally derivatized cellulose ethers and silicones.

Likewise suitable polymers are polysaccharides, in particular xanthan gum, guar guar, agar agar, alginates and tyloses and also, for example, Aerosil grades (hydrophilic silicas), carboxymethylcellulose and hydroxyethylcellulose and hydroxypropylcellulose, poly-vinyl alcohol, polyvinylpyrrolidone and bentonites, for example Bentone® Gel VS-5PC (Rheox).

Likewise suitable are quaternary polymers, for example with the INCI name Polyquaternium-37, which conform to the following general formula:

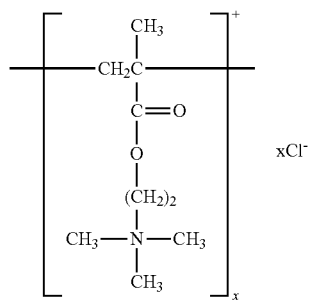

Alternatively, it is also possible to use other dialkylaminoalkyl (meth)acrylates and their ammonium salts obtainable by alkylation or protonation, or dialkylaminoalkyl (meth)acrylamides and their ammonium salts obtainable by alkylation or protonation.

Particular preference is given to polymers comprising MAPTAC, APTAC, MADAME, ADAME, DMAEMA and TMAEMAC. Moreover, it is also possible to use copolymers with anionic, further cationic or uncharged monomers in accordance with the invention, in particular those which, as well as the specified alkylaminoalkyl (meth)acrylate or alkylaminoalkyl(meth)acrylamide monomers, additionally comprise (meth)acrylic acid and/or 2-acrylamido-2-methylpropanesulfonic acid and/or acrylamide and/or vinylpyrrolidone and/or alkyl (meth)-acrylates.

By way of example, mention may be made of those polymers with the INCI name Polyquaternium-11, Polyquaternium-13, Polyquaternium-14, Polyquaternium-15, Polyquaternium-28, Polyquaternium-32, Poly-quaternium-43, Polyquaternium-47.

Oily Substances

In one embodiment of the invention, the inventive cosmetic and/or pharmaceutical formulation further comprises at least one oily substance.

The oily substances are typically present in a total amount of 0.1-90%, especially 0.1-80%, especially 0.5 to 70%, preferably 1 to 60%, especially 1 to 50%, especially 1 to 40%, preferably 5-25% and especially 5-15% by weight. The further oily substances are typically present in an amount of 0.1 to 40% by weight, based on the total weight of the formulation.

Suitable further oily substances are, for example, Guerbet alcohols based on fatty alcohols having 6 to 18, preferably 8 to 10, carbon atoms, and also further additional esters such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Additionally suitable are esters of $C_{18}$-$C_{38}$-alkylhydroxycarboxylic acids with linear or branched $C_6$-$C_{22}$-fatty alcohols, especially Dioctyl Malate, esters of linear and/or branched fatty acids with polyhydric alcohols (for example propylene glycol, dimerdiol or trimertriol), triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, especially benzoic acid, esters of $C_2$-$C_{12}$-dicarboxylic acids with polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, for example Dicaprylyl Carbonate (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, for example dicaprylyl ether (Cetiol® OE), and ring-opening products of epoxidized fatty acid esters with polyols and hydrocarbons or mixtures thereof. Additionally suitable are esters of 2-propylheptanol with n-octanoic acid, as commercially available, for example, under the Cetiol®SenSoft trade name (Cognis GmbH). Additionally suitable are hydrocarbons, for example n-undecane and n-tridecane. Additionally suitable are alkanes, for example the mixtures with the INCI name Coconut/Palm/Palm Kernel Oil Alkanes (trade name Vegelight 1214 from Biosynthesis).

Useful further oily substances are, for example, silicone oils. They may be present as cyclic and/or linear silicone oils. Silicone oils are high molecular weight synthetic polymeric compounds in which silicon atoms are joined via oxygen atoms in a chain-like and/or grid-like manner and the remaining valences of silicon are satisfied by hydrocarbon radicals (usually methyl, more rarely ethyl, propyl, phenyl groups etc.). Systematically, the silicone oils are referred to as polyorganosiloxanes. The methyl-substituted polyorganosiloxanes, which are the most important compounds of this group in terms of volume and are characterized by the following structural formula

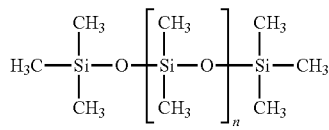

are also referred to as polydimethylsiloxane or dimethicone (INCI). Dimethicones come in various chain lengths and with various molecular weights.

Advantageous polyorganosiloxanes in the context of the present invention are, for example, dimethylpolysiloxane [poly(dimethylsiloxane)], which are available, for example, under the Abil 10 to 10 000 trade names from Evonik Goldschmidt. Also advantageous are phenylmethylpolysiloxane (INCI: Phenyl Dimethicone, Phenyl Trimethicone), cyclic silicones (octamethyl-cyclotetrasiloxane or decamethylcyclopentasiloxane), which are also referred to in accordance with INCI as Cyclomethicone, amino-modified silicones (INCI: Amodimethicone) and silicone waxes, e.g. polysiloxanepolyalkylene copolymers (INCI: Stearyl Dimethicone and Cetyl Dimethicone) and dialkoxydimethylpolysiloxanes (Stearoxy Dimethicone and Behenoxy Stearyl Dimethicone), which are available as various Abil wax grades from Evonik Goldschmidt. However, other silicone oils can also be used advantageously in the context of the present invention, for example cetyldimethicone, hexamethylcyclotrisiloxane, polydimethylsiloxane, poly-(methylphenylsiloxane). Silicones which are particularly preferred in accordance with the invention are dimethicone and cyclomethicone.

The inventive formulations may further comprise biogenic active ingredients, insect repellents, tyrosinase inhibitors, preservatives, perfume oils, superfatting agents, stabilizers and/or hydrotropes.

The invention provides cosmetic and/or pharmaceutical formulations comprising, in a cosmetically and/or pharmaceutically suitable carrier, 0.1 to 50% by weight, preferably 0.5 to 10% by weight, based on the formulation, of a mixture of alkyl sulfosuccinate monoesters of the general formula (I) and/or (II)

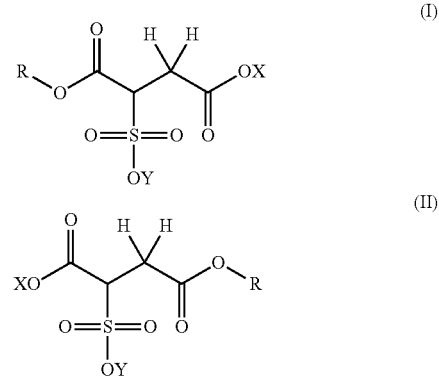

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises 30 to 70% by weight of C16-alkyl sulfosuccinate monoester and 30 to 70% by weight of C18-alkyl sulfosuccinate monoester, where the percentages by weight are based on the total amount of the alkyl sulfosuccinate monoesters of the formulae (I) and (II), and at least one compound selected from the group consisting of biogenic active ingredients, insect repellents, tyrosinase inhibitors, preservatives, perfume oils, stabilizers and/or hydrotropes.

The invention further provides cosmetic and/or pharmaceutical formulations comprising, in a cosmetically and/or pharmaceutically suitable carrier, 0.1 to 50% by weight, preferably 0.5 to 10% by weight, based on the formulation, of a mixture of alkyl sulfosuccinate monoesters of the general formula (I) and/or (II)

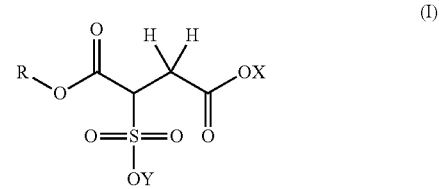

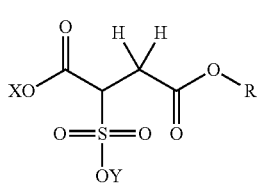
(II)

in which R is a linear or branched, saturated or unsaturated alkyl radical having 6 to 22 carbon atoms, X and Y are each independently a hydrogen atom or a cation which is capable of forming a water-soluble salt and is selected from the group consisting of alkali metal, alkaline earth metal, ammonium and organic ammonium, characterized in that the mixture comprises
- 30 to 70% by weight of C16-alkyl sulfosuccinate monoester and
- 30 to 70% by weight of C18-alkyl sulfosuccinate monoester, where the percentages by weight are based on the total amount of the C16- and C18-alkyl sulfosuccinate monoesters present in the mixture of the formulae (I) and (II),
and where the mixture comprises at least 50% by weight of C16- and C18-alkyl sulfosuccinate monoesters based on the sum of the alkyl sulfosuccinate monoesters of the formulae (I) and (II);
and at least one compound selected from the group consisting of biogenic active ingredients, insect repellents, tyrosinase inhibitors, preservatives, perfume oils, stabilizers and/or hydrotropes.

In a preferred embodiment of the invention, this mixture comprises at least 60% by weight, preferably at least 70% by weight, especially at least 80% by weight, of C16- and C18-alkyl sulfosuccinate monoesters based on the sum of the alkyl sulfosuccinate monoesters of the formulae (I) and (II).

Biogenic active ingredients are understood to mean, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example Aloe Vera, prunus extract, bambara nut extract and vitamin complexes.

Useful insect repellents include, for example, N,N-dimethyl-m-toluamide, 1,2-pentanediol or ethyl 3-(N-n-butyl-N-acetylamino)propionate, which is sold under the Insect Repellent® 3535 name by Merck KGaA, and butylacetylaminopropionates.

Useful tyrosine inhibitors which prevent the formation of melanine and find use in depigmenting agents include, for example, arbutin, ferulic acid, kojic acid, cumaric acid and ascorbic acid (vitamin C).

Suitable preservatives are, for example, phenoxyethanol, formaldehyde solution, parabens, pentanediol or sorbic acid, and the silver complexes known under the Surfacine® name. Additionally suitable as preservatives are the 1,2-alkanediols having 5 to 8 carbon atoms, which are described in WO 07/048,757.

Suitable preservatives are especially the substances approved according to Annex VI of the Commission Directive (in the version: Commission Directive 2007/22/EC of 17 Apr. 2007 amending Council Directive 76/768/EEC, concerning cosmetic products, for the purposes of adapting Annexes IV and VI thereto to technical progress), to which reference is made here explicitly.

Perfume oils include mixtures of natural and synthetic odorants. Natural odorants are extracts from flowers, stems and leaves, fruit, fruit shells, roots, wood, herbs and grasses, needles and branches, resins and balsams. Additionally useful are animal raw materials, for example civet and castoreum, and synthetic odorant compounds of the ester, ether, aldehyde, ketone, alcohol and hydrocarbon type.

The stabilizers used may be metal salts of fatty acids, for example stearates or ricinoleates of magnesium, aluminum and/or zinc.

To improve the flow behavior, it is also possible to use hydrotropes, for example ethanol, isopropyl alcohol or polyols. Polyols which are useful here possess preferably 2 to 15 carbon atoms and at least two hydroxyl groups. The polyols may comprise further functional groups, especially amino groups, or be modified with nitrogen.

EXAMPLES

1. Preparation Example

Stage 1: 382.5 g (1.5 mol) of a C16/18 fatty alcohol mixture (INCI: Cetearyl Alcohol, trade name Lanette® O, obtainable from Cognis GmbH), 149.3 g (1.52 mol) of maleic anhydride and 1.9 of sodium carbonate were weighed into a 2 liter glass flask and heated to 80° C. while stirring for 3 hours.

Stage 2: A 4 liter glass flask was initially charged with 198.5 g (1.53 mol) of sodium sulfite in 1336.0 g of water, and heated to 80° C. while stirring. To this were added 518 g of stage 1 while stirring, and the mixture was stirred at 80° C. for 2 hours. The white solid product had the following composition:

Sulfosuccinate: 29.3% by weight (of which 48% by weight was C16 sulfosuccinate monoester and 52% by weight C18 sulfosuccinate monester), Sodium sulfate: 0.78%; dry residue: 34.8%; C16/18 alcohol: 1.2% (=3.4% based on dry residue). This corresponds to a proportion of fatty alcohol of 4.1% by weight based on the sulfosuccinates.

Stage 3: The spray drying was carried out in the Mobile Minor 2000 spray tower, from Niro, with 2-substance nozzle and rotating plunger pump under the following conditions:

Spray pressure: 0.5 bar

Drying gas rate: 100 m³/h

Drying gas temperature: inlet: 170° C.

Drying gas temperature: outlet: 103° C.

Spray rate: 900 g/h

The product from stage 1 was diluted with 40% water before drying in order to lower the viscosity and to make the solution pumpable. The drying was effected in countercurrent, with the aqueous solution being conducted from the bottom upward and the drying gas from the top downward. The product was spray-dryable without any problem to a water content of 1.5%. No caking was observed on the walls. The powder thus obtained had the following composition:

Sulfosuccinates: 72% by weight (of which 48% by weight were C16 sulfosuccinate monoesters and 52% by weight C18 sulfosuccinate monoesters), sodium sulfate: 2.6%, water: 1.6%, C16/18 alcohol: 3.4%.

This corresponds to a proportion of fatty alcohol of 4.7% by weight based on the sulfosuccinates.

2. Emulsifying Properties

The inventive alkyl sulfosuccinate mixture (in powder form) prepared in preparation example 1 was used to formulate the emulsion which follows. The comparative example used was a commercially available emulsifier: Amphisol®K, INCI Potassium Cetyl Phosphate, obtainable from DSM Nutritional Products. As evident from the table below, a stable emulsion is obtained only with the inventive alkyl sulfosuccinate mixture. All figures in percent by weight.

| Formulation | Inventive example | Comparative example |
| --- | --- | --- |
| Phase I: | | |
| Alkyl sulfosuccinate mixture according to example 1 | 1.0 | — |
| Amphisol ® K (Potassium Cetyl Phosphate) | — | 1.0 |
| Lanette ®O (Cetearyl alcohol) | 5.0 | 5.0 |
| Cetiol ®LC (Coco caprylate/caprate) | 16.0 | 16.0 |
| Phase II | | |
| Water | 72.9 | 72.9 |
| Glycerol | 3.0 | 3.0 |
| Sodium chloride | 1.0 | 1.0 |
| Phase III: Phenonip ® XB (mixture of phenoxyethanol and methylparaben and propylparaben and ethylparaben) | 1.0 | 1.0 |
| Phase IV: Euxyl ® K100 (mixture of benzyl alcohol and methylchloroisothiazolinone and methylisothiazolinone) | 0.1 | 0.1 |
| Appearance after preparation | white emulsion | separated emulsion, water at the bottom |
| Viscosity on day 1, Brookfield RVF, TE spindle, 4 rpm, with Helipath | 125000 mPa*s | — |
| pH | 5.8 | — |

The examples were prepared as follows: phase I was heated to 85° C. and stirred homogeneously, phase II was heated to 85° C. and added to phase I while stirring. The mixture was cooled while stirring. Phase III was added at 45° C., phase IV at 35° C. On attainment of 30° C., the stirring was ended.

The formulations which follow comprise the alkyl sulfosuccinate mixture according to preparation example 1; the INCI name of this compound is Disodium Cetearyl Sulfosuccinate; it is obtainable under the Eumulgin®Prisma trade name from Cognis GmbH, Dusseldorf. All figures are percentages by weight based on the overall composition.

TABLE 1

O/W bodycare emulsions

| | 1 | 2 | 3 | 4 | 5 | 6 | 7 | 8 | 9 | 10 | 11 |
| --- | --- | --- | --- | --- | --- | --- | --- | --- | --- | --- | --- |
| Constituents: Trade name | C | C | C | L | C | L | L | C | L | C | C |
| Eumulgin ® VL 75 | | | | | | | | 2.0 | | 1.5 | |
| Dehymuls ® PGPH | | 0.6 | | | | | | | | | |
| Generol ® R | | | 0.5 | | | | | | | | |
| Eumulgin ® B2 | | 2.0 | | | | | | | | 2.0 | |
| Tween ® 60 | | | | 0.2 | | | | | | | |
| Cutina ® E 24 | | | | 0.2 | | | | | | | |
| Hostaphat ® KL 340 N | | | | | | | | | | 0.5 | |
| Lanette ® E | | | | | | | | 0.6 | | | |
| Amphisol ® K | | | 0.2 | | | | | | | | |
| Sodium Stearate | | | | | 0.5 | | | | | | |
| Emulgade ® PL 68/50 | 3.0 | | | | | 2.0 | | | | | 1.2 |
| Eumulgin ® SG | 0.2 | | | | 0.2 | 0.3 | | | | | |
| Eumulgin ® Prisma | 0.1 | 0.2 | 0.1 | 0.1 | 0.1 | 0.5 | 0.2 | 0.1 | 0.1 | 0.2 | 0.5 |
| Imwitor 372 P | | 2.0 | 2.0 | | | 3.0 | | | | 3.0 | 3.0 |
| Tego ® Care CG | 0.7 | | | | | | | | | | |
| Tego ® Care 450 | | | | | 3 | | 1.0 | | | 1.0 | |
| Cutina ® PES | 2.5 | 2 | 3 | | | 2 | | 1.7 | 2.5 | | 1.2 |
| Cutina ® MD | | 1 | | 3 | 5 | | 2 | | | 3 | |
| Lanette ® 14 | | | | 1 | | | 4 | | | | 4 |
| Lanette ® O | 4.5 | | 4 | | 1 | | | | | | 2 |
| Novata ® AB | | 1 | | | | | | | | | 1 |
| Emery ® 1780 | | | | | 0.5 | 0.5 | | | | | |
| Lanolin, water-free, USP | | | | | | | 1.1 | | | | |
| Cosmedia ® DC | | 1.5 | 2 | | | 1.5 | 2 | | | 1.5 | 1.5 |
| Cetiol ® SB 45 | | | 1.5 | | | | 2 | | | | |
| Cegesoft ® C 17 | | | | | | | | | | | 2 |
| Myritol ® PC | | | | 5 | | | | | | | |
| Myritol ® 331 | 2 | 5 | 1 | | | 6 | | 6 | | | |
| Finsolv ® TN | | | 2 | | | 2 | 4 | | | | |
| Cetiol ® Sensoft | 4 | 3 | | 5 | 4 | 4 | | 6 | 8 | | 5 |
| Cetiol ® CC | 2.0 | 3 | | | | 2.0 | 4 | | | 3.0 | 5 |
| Cetiol ® OE | | | 2.0 | | | | | | 4 | | |
| Dow Corning DC ® 245 | | | | 2 | 1 | 1 | | | | | |
| Dow Corning DC ® 2502 | | | | | 2 | 1 | | | | 3 | |
| Prisorine ® 3758 | | | 4 | | | | 1 | | | | |
| Silicone Oil Wacker AK ® 350 | 0.5 | 0.5 | 0.5 | | 1 | | | | | | |

TABLE 1-continued

O/W bodycare emulsions

C—Cream, L—Emulsion

| Constituents: Trade name | 1 | 2 | 3 | 4 | 5 | 6 | 7 | 8 | 9 | 10 | 11 |
|---|---|---|---|---|---|---|---|---|---|---|---|
|  | C | C | C | L | C | L | L | C | L | C | C |
| Cetiol ® 868 |  |  |  |  | 2 |  | 4 |  |  |  |  |
| Cetiol ® J 600 |  | 2 |  | 3 |  | 3 | 2 |  |  | 5 |  |
| Ceraphyl ® 45 |  |  |  |  |  |  | 3 |  |  |  |  |
| Mineral oil |  |  |  | 9 |  |  |  |  |  |  |  |
| Cetiol ® SN |  |  | 5 |  |  |  |  |  |  |  |  |
| Cetiol ® B |  |  |  |  |  |  |  | 4 |  | 2 |  |
| Eutanol ® G |  | 2 |  | 3 |  |  |  |  |  |  |  |
| Cetiol ® PGL |  |  |  |  |  |  |  |  | 5 | 5 |  |
| Dry Flo ® Plus | 5 |  |  |  |  | 1 |  |  |  |  |  |
| SFE 839 | 5 |  |  |  |  |  |  |  |  |  | 2 |
| Almond Oil |  |  |  |  |  |  | 1 |  |  |  |  |
| Insect Repellent ® 3535 |  | 2 | 4 |  |  | 2 |  |  |  | 3 |  |
| N,N-Diethyl-m-toluamide |  | 2 |  |  |  |  |  |  |  | 3 |  |
| Photonyl ® LS | 2 | 2 |  |  |  | 2 |  |  |  |  |  |
| Panthenol |  |  |  |  |  |  | 1 |  |  |  |  |
| Bisabolol |  |  |  |  |  |  | 0.2 |  |  |  |  |
| Tocopherol/Tocopheryl Acetate |  |  |  |  |  |  | 1 |  |  |  |  |
| Veegum ® Ultra |  |  |  |  |  |  |  | 1 |  |  |  |
| Keltrol ® T |  |  |  | 0.4 |  |  |  | 0.5 |  |  |  |
| Cosmedia ® SP |  | 0.2 |  |  | 0.2 | 0.2 |  |  | 0.2 | 0.3 |  |
| Pemulen ® TR 2 |  |  |  |  |  |  |  | 0.3 |  |  |  |
| Carbopol ® Ultrez 10 |  |  |  |  |  | 0.2 |  |  |  |  |  |
| Rheocare ® C Plus | 0.3 | 0.1 | 0.3 |  | 0.2 |  |  |  |  | 0.2 |  |
| Ultragel ™ 300 |  |  |  | 0.3 |  |  |  |  |  |  |  |
| Ethanol |  |  |  |  |  |  |  |  |  | 10 |  |
| Butylene glycol |  |  |  |  | 4 | 3 |  | 2 | 5 | 2 |  |
| Glycerin |  | 2 | 5 | 5 |  | 3 | 3 | 2 |  | 4 | 3 |
| Water, Preservatives, NaOH | ad 100, q.s., pH 6.5-7.5 | | | | | | | | | | |

TABLE 2

W/O bodycare emulsions

L = Emulsion, C = Cream

| Ingredients: Trade names | 1 | 2 | 3 | 4 | 5 | 6 | 7 | 8 | 9 | 10 | 11 |
|---|---|---|---|---|---|---|---|---|---|---|---|
|  | C | L | C | L | C | L | L | L | C | C | C |
| Dehymuls ® PGPH | 1 | 2 | 1 | 2 | 3 | 1 | 1 | 2 |  |  | 1 |
| Monomuls ® 90-O18 | 2 |  |  |  |  |  |  |  | 2 |  | 2 |
| Lameform ® TGI | 4 | 1 |  |  | 3 |  |  | 1 | 4 | 3 |  |
| Abil ® EM 90 |  |  |  |  |  |  | 4 |  | 1 |  |  |
| Isolan GPS |  |  | 2 |  | 2 |  |  |  |  | 1 |  |
| Isolan ® PDI |  |  |  |  |  | 4 |  |  |  |  | 1 |
| Glucate ® DO |  |  |  | 3 |  |  |  |  |  |  |  |
| Arlacel ® 83 |  |  |  | 4 |  |  |  |  |  |  |  |
| Dehymuls ® LE |  | 1 | 1 | 2 |  |  |  |  |  | 1 | 1 |
| Dehymuls ® HRE 7 |  |  |  |  |  |  |  | 4 |  | 1 |  |
| Zinc Stearate | 2 | 1 |  | 1 | 1 |  |  | 1 | 1 | 1 |  |
| Microcrystalline Wax |  |  | 5 |  |  |  | 2 |  |  |  | 5 |
| Beeswax | 4 |  |  | 1 |  |  |  | 1 | 4 | 7 |  |
| Imwitor 372 P |  |  |  |  | 1 |  |  |  |  |  |  |
| Tego Care ® CG |  |  |  |  | 1 |  |  |  |  |  | 0.5 |
| Eumulgin ® Prisma | 0.1 | 0.05 | 0.1 | 0.15 | 0.05 | 0.05 | 0.1 | 0.1 | 0.15 | 0.05 | 0.2 |
| Prisorine ® 3505 |  |  | 1 | 1 |  | 1 | 1 |  |  |  | 1 |
| SFE ® 839 |  |  |  |  |  |  | 3 |  |  |  |  |
| Emery ® 1780 | 1 |  |  |  |  |  |  |  |  |  | 1 |
| Anhydrous Lanolin USP |  |  | 5 |  |  |  |  |  |  | 4 |  |
| Cetiol ® Sensoft | 3 | 4 |  |  | 6 |  | 2 | 6 | 3 | 8 |  |
| Cegesoft ® C 17 |  |  | 3 |  |  |  |  |  |  | 1 |  |
| Myritol ® PC |  |  |  |  |  | 2 |  | 4 |  |  |  |
| Myritol ® 331 | 6 |  |  |  | 2 | 6 | 2 |  |  |  | 8 |
| Finsolv ® TN |  |  |  | 5 |  | 4 | 5 |  |  |  |  |
| Cetiol ® A |  | 6 |  |  |  | 4 |  |  |  |  |  |
| Cetiol ® CC |  | 8 |  | 6 | 6 | 2 | 2 |  |  | 4 | 6 |
| Cetiol ® SN |  | 5 |  |  |  |  |  | 3 |  |  |  |
| Cetiol ® OE | 3 |  | 2 |  | 4 |  | 2 |  | 4 | 2 |  |
| Dow Corning DC ® 244 |  |  |  | 6 | 1 |  | 2 |  |  |  |  |
| Dow Corning DC ® 2502 |  |  | 1 |  | 2 |  |  |  |  |  |  |

TABLE 2-continued

W/O bodycare emulsions

L = Emulsion, C = Cream

| Ingredients: Trade names | 1 (C) | 2 (L) | 3 (C) | 4 (L) | 5 (C) | 6 (L) | 7 (L) | 8 (L) | 9 (C) | 10 (C) | 11 (C) |
|---|---|---|---|---|---|---|---|---|---|---|---|
| Prisorine ® 3758 | | | | | 3 | | | | | | |
| Silicon Oil Wacker AK ® 350 | | | | 4 | | | | 3 | | | |
| Cetiol ® 868 | | | | | | | | | | 2 | 7 |
| Cetiol ® J 600 | | | 4 | | | 2 | | | | | |
| Ceraphyl ® 45 | | | | 2 | | | | 2 | | 6 | |
| Mineral oil | | | | | 4 | | | | | | |
| Cetiol ® B | | | 2 | 4 | | | | | | 3 | |
| Eutanol ® G 16 | | 1 | | | | | | | | 3 | |
| Eutanol ® G | | | 3 | | | | | 8 | | | |
| Cetiol ® PGL | | | | | | 4 | 5 | | 9 | | |
| Almond Oil | | | | | 1 | | 5 | | | | |
| Insect Repellent ® 3535 | 2 | | | | | | | | | | |
| Unirep ® U-18 | | | | 3 | | | | 5 | | | |
| Photonyl ® LS | 2 | 2 | | | | | | | | | |
| Panthenol | | | | | | 1.0 | | | | | |
| Bisabolol | | | | | | 0.2 | | | | | |
| Copherol ® 1250 C | | | | | | 1 | | | | | |
| MgSO₄ × 7 H₂O | | | | | | 1 | | | | | |
| Bentone ® 38 | | | | | 1 | | | | | | |
| Propylene Carbonate | | | | | 0.5 | | | | | | |
| Ethanol | | | | | | | | | | 8 | |
| Butylene Glycol | | | 2 | 6 | | | 2 | 5 | | | 2 |
| Glycerin | 5 | 3 | 3 | | 5 | 3 | 2 | | 10 | 4 | |
| Water, Preservative | ad 100, q.s. | | | | | | | | | | |

TABLE 3

O/W suncare emulsions

| Ingredients: (Trade names) | 1 | 2 | 3 | 4 | 5 | 6 | 7 | 8 | 9 | 10 | 11 |
|---|---|---|---|---|---|---|---|---|---|---|---|
| C—Cream, L - Emulsion | L | C | S | L | C | L | L | C | L | C | L |
| Dehymuls ® PGPH | | | | | | | 1.5 | | 1 | | |
| Eumulgin ® VL 75 | | | | | | | | 2 | | | 2 |
| Eumulgin ® B2 | | | 0.5 | | | | | | | | |
| Tween ® 60 | | | 0.2 | | | | | | | | |
| Myrj ® 51 | | | 0.5 | | | | | | | | |
| Cutina ® E 24 | | | 0.1 | | | | | | | | |
| Hostaphat ® KL 340 N | | | | | | | | | 1.6 | | |
| Lanette ® E | | | | | | | | | | | 0.1 |
| Amphisol ® K | | | | | | | | | | 1 | |
| Sodium Stearate | | | | | | | 1 | | | | |
| Emulgade ® PL 68/50 | | 2 | 1 | | | 2 | 2 | | | 2 | |
| Imwitor 372 P | | 2 | | | | 2 | 1 | | 2 | | |
| Eumulgin ® SG | | | 0.5 | | | | 0.1 | | 0.2 | | |
| Eumulgin ® Prisma | 0.5 | 0.2 | 0.2 | 0.2 | 0.75 | 0.2 | 0.2 | 0.1 | 0.2 | 0.4 | 0.3 |
| Tego ® Care 450 | | | | | | | 2 | | | 1 | 2.5 |
| Cutina ® PES | | 2 | | 2.5 | 1 | 2.5 | | 2.5 | | 1.7 | 1.5 |
| Cutina ® MD | | 2 | | 1 | 2 | | | 2 | | 6 | |
| Lanette ® 14 | | 1 | | | 1 | | | 2 | | | 2 |
| Lanette ® O | | 1 | 6 | | | 5 | 2 | | 2 | | |
| Cosmedia ® DC | | 1 | 1.5 | | 1 | 1 | | 2 | 2 | | 2 |
| Antaron ® V 216 | | | | 2 | | | 1.5 | | | 1 | 1 |
| Emery 1780 | | | | | | 0.5 | 0.5 | | | | |
| Lanolin, water-free USP | | | | | | | | 5 | | | |
| Myritol ® PC | | | | | 5 | | | | | | |
| Myritol ® 331 | | | 8 | | | 6 | | 10 | | 2 | |
| Finsolv ® TN | | 3 | | 1 | 5 | | | | 1 | 2 | |
| Cetiol ® Sensoft | | | 2 | 3 | | 3 | 4 | 3 | 2 | 5 | 5 |
| Cetiol ® CC | | 5 | 2.5 | 2 | | 2 | | 1 | | 3 | |
| Cetiol ® OE | | | | 3 | | | | | 2 | 3 | |
| Dow Corning DC ® 244 | | 4 | | 1 | | | | | 2 | | 2 |
| Dow Corning DC ® 2502 | | | 1 | | | 2 | | | | | |
| Squatol ® S | | | | | | | | 4 | | | |
| Silicone Oil Wacker AK ® 350 | | | 2 | | | | | | | | |
| Cetiol ® 868 | | | | | | 2 | | 4 | | | 2 |
| Cetiol ® J 600 | | | | | | 3 | 2 | | | 5 | |
| Mineral Oil | | | | 4 | | | | | | | |
| Cetiol ® B | | | | 1 | | | | | | 2 | |

TABLE 3-continued

O/W suncare emulsions

| Ingredients: (Trade names) | 1 | 2 | 3 | 4 | 5 | 6 | 7 | 8 | 9 | 10 | 11 |
|---|---|---|---|---|---|---|---|---|---|---|---|
| Eutanol ® G | | | | 2 | | | | | 4 | | |
| Eutanol ® G 16 | 4 | | | | | 4 | | | | | |
| Cetiol ® PGL | | | 5 | | | | | | | | |
| Almond Oil | | | | 2 | | | 1 | 1 | | | |
| Photonyl ® LS | | | | | 2 | | | | | 2 | |
| Panthenol | | | | | | | 1 | | | | |
| Bisabolol | | | | | | | | 0.2 | | | |
| Tocopherol/Tocopheryl Acetate Photonyl ® LS | | | | | | | | 1 | | | |
| Neo Heliopan ® AP (Na-salt) | | 1 | | | | | | | 1 | | |
| Neo Heliopan ® Hydro (Na-salt) | | 1 | 2.2 | | | | | | 1 | | |
| Neo Heliopan ® 303 | 3 | 5 | 4 | 4 | | 2 | | | | | |
| Neo Heliopan ® BB | | | | | 1 | | | | | | 2 |
| Neo Heliopan ® MBC | | | | 3 | | 2 | 2 | 2 | | | 1 |
| Neo Heliopan ® HMS | | 2 | | | | | | | 5 | | |
| Neo Heliopan ® OS | | 2 | | | | | | | 5 | | |
| Neo Heliopan ® E 1000 | | | | 3 | | | | | | | 6 |
| Neo Heliopan ® AV | | | 7.5 | 3 | | 4 | 4 | 5 | | | |
| Uvinul ® A Plus | | 2 | | 2 | 1 | | | | 2 | | 1 |
| Uvinul ® T 150 | | 2 | | | 2.5 | | | 1 | | 2 | 2.5 |
| Tinosorb ® M | | | 3 | | 2 | | 2 | 2 | | | 2 |
| Tinosorb ® S | | | 1 | | 1 | | | 1.5 | 1 | | 1 |
| Uvasorb ® HEB | | 1 | | | 1 | | | | | | |
| Parsol ® 1789 | 3 | | 1 | | 1 | 1 | 2 | | 2 | 2 | 1 |
| Mexoryl SX (Na-salt) | 1 | | | | | 2 | 1 | | | 2 | |
| Mexoryl XL | 2 | | | | | 2 | 2 | | | 3 | |
| Zincoxide NDM | | | 5 | | | 5 | | 3 | | 5 | 4 |
| Eusolex ® T 2000 | 5 | | | | 5 | 5 | 3 | 3 | | | 4 |
| Veegum ® Ultra | 1.5 | | 0.75 | | | | | 1 | 1 | | |
| Keltrol ® T | 0.5 | | 0.25 | | | | | 0.5 | 0.5 | | |
| Cosmedia ® SP | | 0.2 | | | 0.2 | | 0.2 | 0.2 | | 0.2 | 0.2 |
| Ultragel ™ 300 | | | | 0.4 | | 0.2 | | | 0.1 | | |
| Rheocare ® C Plus | 0.1 | 0.3 | | | 0.3 | | 0.1 | | | 0.3 | 0.2 |
| Ethanol | | | | | | | | | | 10 | |
| Butylene glycol | | 2 | | 4 | 3 | | 2 | 5 | 2 | | 2 |
| Glycerin | 5 | 5 | 5 | | 3 | 3 | 2 | | 4 | | 3 |
| Preservatives, NaOH, Water | | | | | q.s. ad 100 | | | | | | |

TABLE 4

Decorative cosmetics - O/W foundations

| Ingredients (Trade names) | 1 | 2 | 3 | 4 | 5 | 6 | 7 | 8 |
|---|---|---|---|---|---|---|---|---|
| Cutina ® GMS-SE | 5.5 | | | | | | | |
| Emulgade ® PL 68/50 | | 5.0 | | | | 2.0 | | |
| Eumulgin ® VL 75 | | | 3.0 | | | | 5.0 | |
| Tego Care ® 450 | | | | | | 2.0 | 2.0 | |
| Crodesta ® F-50 | | | | | 6.0 | | | |
| Amphisol ® K | | | 2.0 | | | | | |
| Lanette ® E | | 0.25 | | | | | | |
| Eumulgin ® SG | | | | | 0.5 | | 0.2 | |
| Eumulgin ® Prisma | 0.1 | 0.3 | 0.1 | 0.5 | 0.5 | 1.0 | 1.0 | 0.75 |
| Imwitor 372 P | | 2 | | 2 | | | 1 | |
| Cutina ® FS 45 | 1.5 | | | | | | 1 | |
| Eumulgin ® B 2 | | | 2.0 | | | | | |
| Cutina ® PES | 2.0 | 1.0 | 2.0 | | 2.0 | 1.0 | 2.5 | 2.0 |
| Lanette ® O | | | 2.0 | 4.0 | | | | 1.0 |
| Cutina ® MD | | 0.5 | 3.0 | 3.0 | | | | 3.0 |
| Cetiol ® LC | 4.0 | | | | 3.0 | | | |
| Cosmedia ® DC | 0.5 | | | 1.0 | | | | 1.0 |
| Cetiol ® Sensoft | 4.0 | 5.0 | | 2.0 | | | 5 | 4.0 |
| Tegosoft ® DEC | | | | 2.0 | | 2.0 | | 2.0 |
| Cetiol ® CC | 2.0 | | 2.0 | 2.0 | | | | 2.0 |
| Dow Corning ® 1503 Fluid | | 5.0 | 8.0 | | 5.0 | | | |
| Dow Corning ® 245 | | 2.0 | | 2.0 | 7.0 | | 5 | |
| Eutanol ® G 16 | 4.0 | | | | | 3.0 | | |
| Myritol ® 331 | | 5.0 | | | 2.0 | 2.0 | 5.0 | |
| Uvinul ® T 150 | | | | 0.5 | | | | 0.5 |
| Uvasorb ® HEB | 2.0 | | | | | 1.0 | 1.0 | |
| Tinosorb ® M | | | 2.0 | | | | | 2.0 |
| Tinosorb ® S | | | | | 3.0 | | | 2.0 |
| Neo Heliopan ® AV | | | | | 2.0 | | 2.0 | |
| Heo Heliopan ® AP | | | | | 1.0 | | 1.0 | |
| Uvinul ® A Plus | | | | 1 | | | 2.0 | 2.0 |
| Microna ® Matte White | 5.0 | 5.0 | | | 5.0 | 5.0 | 5.0 | |
| Microna ® Matte Black | 0.3 | 0.3 | 0.1 | 0.3 | 0.3 | 0.3 | 0.4 | 0.3 |
| Microna ® Matte Yellow | 3.0 | 3.0 | | | 3.0 | 3.0 | 3.0 | 2.0 |
| Microna ® Matte Red | 0.6 | 0.6 | 1.0 | 0.6 | 0.6 | 0.6 | 1.0 | 0.6 |
| Ronasphere ® LDP | 1.0 | 1.0 | | | 1.0 | 1.0 | 1.0 | |
| Pigment White 6 | | | 6.0 | | | 6.0 | | |
| Dry Flow PC | | | | | | | 2.0 | 2.0 |
| Glycerin | 5.0 | 5.0 | 3.0 | 5.0 | 5.0 | 5.0 | 3.0 | |
| Cosmedia ® SP | | | 0.3 | | 0.2 | | | |
| Ultragel ™ 300 | | | | 0.4 | | | | 0.2 |
| Rheocare ® C Plus | 0.3 | | 0.1 | 0.4 | | 0.3 | | |
| Water, deionized, Preservative | | | | | ad 100 | | | |

TABLE 5

| Ingredients: INCI (Trade names) | 1 | 2 | 3 | 4 | 5 | 6 | 7 |
|---|---|---|---|---|---|---|---|
| Glyceryl Stearate, Ceteareth-20, Ceteareth-12, Cetearyl Alcohol, Cetyl Palmitate (Emulgade ® SE) | 6 | | | 4.5 | | 6 | |
| Ceteareth-20 (Eumulgin ® B2) | | | | 1 | | | |
| Glyceryl Stearate Citrate (Imwitor 372 P) | | 4.0 | | | | | |
| Polyglyceryl-3 Diisostearate (Lameform ® TGI) | | | 3 | | | | |
| Cocoglycerides (Novata ® AB) | | | | | | | 4 |
| Stearyl alcohol (Lanette ® 18) | | | | | 10 | | |
| Hydrogenated Castor Oil (Cutina ® HR) | | | | | 3.7 | | 6.5 |
| Polyglyceryl-2 Dipolyhydroxystearate (Dehymuls ® PGPH) | | | 1 | | | | |
| Sodium Stearoyl Glutamate (Eumulgin ® SG) | | 0.2 | | | | | |
| Disodium Cetearyl Sulfosuccinate (Eumulgin ® Prisma) | 0.3 | 0.1 | 0.05 | 0.05 | 0.2 | 0.2 | 0.1 |
| Sodium Cetearyl Sulfate (Lanette ® E) | | | | | | 0.3 | |
| Pentaerythrityl Distearate (Cutina ® PES) | 5 | 1 | 2 | 1 | 4.7 | 5 | 4 |
| Behenyl Alcohol (Lanette ® 22) | 2 | 1 | | | | 4 | |
| 2-Hexyldecyl-hexansaureester | 4 | 4 | 5 | 3 | 4 | 3 | 5 |
| Propylheptyl Caprylate (Cetiol ® Sensoft) | | 2 | | | 20 | | 10 |
| Dicaprylyl Carbonate (Cetiol ® CC) | | | 2 | | | | |
| Dicaprylyl Ether (Cetiol ® OE) | 2 | | | 2 | 5 | 3 | 4 |
| Cocoglycerides (Myritol ® 331) | | | | | | | |
| Diethylhexylcyclohexane (Cetiol ® S) | | | | 5 | 14.7 | | 25 |
| Cyclopentasiloxane | 3 | | 5 | | 14 | 3 | 14 |
| Cyclopentasiloxane and Dimethicone/Vinyldimethicone Crosspolymer SFE 839 (GE Bayer) | | | 3 | | | | |
| Dimethicone AK 350 | 1 | 2 | | | | | |
| Hydrogenated Dimer Dilinoleyl/Dimethylcarbonate Copolymer (Cosmedia ® DC) | 0.5 | | 1 | 1.5 | 1 | 2 | 1 |
| Triethyl Citrate (Hydagen ® C.A.T) | | | | 2 | | | |
| Tocopheryl Acetate | | | | | 1 | | |
| Aluminium Zirconium Tetrachlorohydrex GLY (Reza136) | 30 | | 40 | | 22.9 | 30 | 25 |
| Aluminum Chlorohydrate (Locron ® L) | | 20 | | 10 | | | |
| Chitosan (Hydagen ® DCMF) | 0.05 | | | | | | |
| Glycolic Acid | 0.02 | | | | | | |
| Glycerin | | | | 5 | 5 | | |
| Propylene Carbonate | | | | | | | 0.5 |
| Quaternium-18 Hectorite | | | | | | | 1 |
| Polyquaternium-37 (Ultragel ® 300) | | | 5 | | | | |
| Talcum | | | | | | 5 | 5 |
| MgSO$_4$ × 7H$_2$O | | | | 1 | | | |
| Water, Perfume, Preservatives | q.s. | q.s. | q.s. | q.s. | q.s. | q.s. | q.s. |

1/2—Antiperspirant/deodorant cream, 3—Antiperspirant cream (W/O), 4—Antiperspirant/deodorant spray, 5—Antiperspirant stick with vitamin E, 6—Antiperspirant cream, 7—Antiperspirant "Soft Solid" cream

| Phase | Component Trade name | INCI | % by wt. |
|---|---|---|---|
| | EMULGADE ® CM | Cetearyl Isononanoate (and) Ceteareth-20 (and) Cetearyl Alcohol (and) Glyceryl Stearate (and) Glycerin (and) Ceteareth | 5.0 |
| | EUMULGIN ® VL 75 | Lauryl Glucoside (and) Polyglyceryl-2 Dipolyhydroxystearate (and) Glycerin | 2.0 |
| | Eumulgin ® Prisma | Disodium Cetearyl Sulfosuccinate | 0.5 |
| | CETIOL ® OE | Dicaprylyl Ether | 4.0 |
| | CETIOL ® J 600 | Oleyl Erucate | 1.0 |
| | ISOPROPYLMYRISTATE | Isopropyl Myristate | 7.0 |
| II. | Water, deionized | | ad 100 |
| III. | Cosmedia ® SP | Sodium Polyacrylate | 0.4 |
| IV. | HISPAGEL ® 200 | Glycerin (and) Glyceryl Polyacrylate | 20.0 |
| V. | Preservatives, perfume | | q.s. |

Moisturizing body milk

The preparation was effected by mixing phase I and water at room temperature while stirring. Then phase III was added and the mixture was stirred until a homogeneous, swollen mixture was present. Then phase IV was added, followed by phase V, then the pH was adjusted to 5.5.

| Phase | Component Trade name | INCI | % by wt. |
|---|---|---|---|
| | O/W soft cream | | |
| I. | EMULGADE ® SE-PF | Glyceryl Stearate (and) Ceteareth-20 (and) Ceteareth-12 (and) Stearyl Alcohol (and) Ceteareth-20 (and) Distearyl Ether | 6.0 |
| | Eumulgin ® Prisma | Disodium Cetearyl Sulfosuccinate | 0.2 |
| | LANETTE ® O | Cetearyl Alcohol | 1.0 |
| | CUTINA ® MD | Glyceryl Stearate | 2.0 |
| | CETIOL ® MM | Myristyl Myristate | 2.0 |
| | Jojoba Oil | Simmondsia Chinensis (jojoba) Seed Oil | 2.0 |
| | Cetiol ® Sensoft | Propylheptyl Caprylate | 5.0 |
| | COPHEROL ® 1250 | Tocopheryl Acetate | 0.5 |
| | | Dimethicone | 0.5 |
| | | Cyclomethicone | 3.0 |
| II. | Water | Aqua | ad 100 |
| | | Propylene Glycol | 3.0 |
| III. | HISPAGEL ® 200 | Glycerin (and) Glyceryl Polyacrylate | 15.0 |
| IV. | Preservative | | q.s. | pH 5.5-6.5

This cream was prepared by heating phase 1 to 80° C., and likewise heating phase II to 80° C. and adding it to phase I while stirring. This mixture was cooled by stirring and homogenized at approx. 55° C. with a suitable dispersing unit (e.g. Ultra Turrax). Thereafter, phase III was added while stirring continuously, phase IV was added and the pH was adjusted.

| O/W sunscreen emulsions | | | | | | | | | | | |
|---|---|---|---|---|---|---|---|---|---|---|---|
| Component | 1 | 2 | 3 | 4 | 5 | 6 | 7 | 8 | 9 | 10 | 11 |
| L = Emulsion, C = Cream | L | C | S | L | C | L | L | C | L | C | L |
| Eumulgin ® Prisma | 0.5 | 0.5 | 0.1 | 0.6 | 0.2 | 0.1 | 0.1 | 0.5 | 1.0 | 0.2 | 0.9 |
| Amphisol ® K | | 1 | | | 1 | | | | | | |
| Sodium stearate | | | | | | 1 | | | | | |
| Emulgade ® PL 68/50 | | | 1 | | 5 | | | | 4 | | |
| Tego ® Care 450 | | | | | | | | 3 | | | |
| Cutina ® MD | 2 | | | 6 | | 4 | | | 6 | | |
| Lanette ® 14 | 1 | | | 1 | | | 2 | | | | 4 |
| Lanette ® O | 1 | 6 | | | 5 | 2 | | 2 | | | |
| Antaron V 216 | | | 1 | | 2 | 2 | | | 1 | | |
| Lanolin, anhydrous USP | | | | | | 5 | | | | | |
| Cetiol ® Sensoft | 5 | | | 5 | | | 5 | | | | |
| Myritol ® 331 | | 8 | | | 6 | | 5 | | 2 | | |
| Finsolv ® TN | | 1 | | | | 1 | 8 | | | | |
| Cetiol ® CC | | | 2 | 5 | | 4 | 4 | 2 | | 2 | |
| Cetiol ® OE | | | 3 | | | | | 2 | | 3 | |
| Dow Corning DC ® 244 | 4 | 1 | | 5 | | 2 | | | | | 2 |
| Dow Corning DC ® 2502 | | | 1 | | 2 | | | | | | |

| O/W sunscreen emulsions | | | | | | | | | | | |
|---|---|---|---|---|---|---|---|---|---|---|---|
| Component | 1 | 2 | 3 | 4 | 5 | 6 | 7 | 8 | 9 | 10 | 11 |
| Wacker AK ® 350 silicone oil | | 2 | | | | | | | | | |
| Cetiol ® 868 | | | | | 2 | | 8 | | | | 7 |
| Cetiol ® J 600 | | | 3 | 2 | | | | | 5 | | |
| Mineral oil | | | | | 9 | | | | | | |
| Cetiol ® B | | 1 | | | | | | | | 2 | |
| Eutanol ® G | | | | | | | | | | | |
| Eutanol ® G 16 | | | | | | | | | | | |
| Cetiol ® PGL | 5 | | | | | | 1 | | | 5 | |
| Almond oil | | 2 | | | | | 1 | | | 2 | |
| Photonyl ® LS | | | 2 | | 1 | | | | | | |
| Panthenol | | | | | | | | | | | |
| Bisabolol | | | | | | 0.2 | | | | | |
| Tocopherol/Tocopheryl acetate | | | | | | 1 | | | | | |
| Photonyl ® LS | | | | | 1 | | | | | | |
| Neo Heliopan ® Hydro (Na salt) | 2 | | 2.2 | 3 | 3 | | | | | | 2 |
| Neo Heliopan AP (Na salt) | 2 | | | 1.5 | 2 | 2 | | 1 | | | 1 |
| Neo Heliopan ® 303 | 3 | 5 | 9 | 4 | | | | | | | |
| Neo Heliopan ® BB | | | | 1 | | | | | | | 2 |
| Neo Heliopan ® MBC | 2 | | 3 | | 2 | 2 | 2 | | | | 1 |
| Neo Heliopan ® OS | | | | | | | | | | 10 | 7 |
| Neo Heliopan ® E 1000 | | 7.5 | | 6 | | | | | | | 6 |
| Neo Heliopan ® AV | | | 7.5 | | 7.5 | 4 | 5 | | | | |
| Uvinul ® T 150 | 2 | | | 2.5 | | 1 | | | | | |
| Parsol ® 1789 | | 1 | 1 | | | 2 | | 2 | 2 | | |
| Zinc oxide NDM | 10 | | 5 | | | 10 | | 3 | | 5 | 4 |
| Eusolex ® T 2000 | | | | | 5 | | 3 | 3 | | | 4 |
| Veegum ® Ultra | | | 0.7 | | | | 1 | 1 | | | |
| Keltrol ® T | | | 0.2 | | | | 0.5 | 0.5 | | | |
| Carbopol ® 980 | | 0.5 | | 0.2 | 0.2 | 0.2 | | 0.5 | 0.1 | 0.3 | 0.2 |
| Ethanol | | | | | | | | | | 10 | |
| Butylene glycol | | 2 | | 4 | 3 | | 2 | 5 | 2 | | 2 |
| Glycerin | 5 | 5 | 5 | | 3 | 3 | 2 | | 4 | | 3 |
| Preservative, NaOH | | | | | | q.s. | | | | | |
| Water | | | | | | Ad 100 | | | | | |

| O/W sunscreen emulsions | | | | | | | | | | | |
|---|---|---|---|---|---|---|---|---|---|---|---|
| Component | 12 | 13 | 14 | 15 | 16 | 17 | 18 | 19 | 20 | 21 | 22 |
| L = Emulsion, C = Cream | L | L | L | C | L | C | S | C | C | L | L |
| Eumulgin ® VL 75 | 4 | | | | | | | | | | |
| Eumulgin ® B2 | | | | | | | | | | | 1 |
| Tween ® 60 | | | | | | | | | | | 1 |

| O/W sunscreen emulsions | | | | | | | | | | | |
|---|---|---|---|---|---|---|---|---|---|---|---|
| Component | 12 | 13 | 14 | 15 | 16 | 17 | 18 | 19 | 20 | 21 | 22 |
| Cutina ® E 24 | | | 2 | | | | | | | | |
| Eumulgin ® Prisma | 0.3 | 0.5 | 0.6 | 0.1 | 0.4 | 0.2 | 0.2 | 0.1 | 0.4 | 0.6 | 0.4 |
| Emulgade ® PL 68/50 | | 2 | | | 4.5 | 1 | 5 | | | | |
| Tego ® Care 450 | 1 | | | | | 2 | | 4 | | | |
| Cutina ® MD | 1 | | 8 | 6 | 1 | | | | 4 | 1 | |
| Lanette ® 14 | | 2 | | | | | 2 | | 1 | | |
| Lanette ® O | | | 2 | | | | | 1 | 1 | | |
| Antaron V 220 | 1 | | 2 | | | 0.5 | | | 2 | | 0.5 |
| Myritol ® PC | | | | | | | | | 5 | | |
| Myritol ® 331 | 12 | | 12 | | | 8 | 8 | | 10 | 4 | |
| Finsolv ® TN | | | | 5 | | | 3 | | | | |
| Cetiol ® Sensoft | 6 | | | | | 5 | | 3 | | | 4 |
| Cetiol ® CC | | | 6 | | 5 | | | | | | |
| Cetiol ® OE | | | | 2 | | | | | | | 2 |
| Dow Corning DC ® 244 | | 2 | | 1 | | | | | | | |
| Dow Corning DC ® 2502 | | 1 | | 1 | | | | | | | |
| Ceraphyl ® 45 | | | | | | | | | | 2 | 2 |
| Wacker AK ® 350 silicone oil | | | | 1 | | | | | | | |
| Cetiol ® 868 | | 2 | | | | | | | | | |
| Cetiol ® J 600 | | 2 | | | | | | | | | |
| Cetiol ® B | 4 | | 4 | | | 4 | | | | | |
| Eutanol ® G | | 3 | | 5 | | 3 | | | | | |
| Eutanol ® G 16 S | 10 | | | | | | | | | | |
| Cetiol ® PGL | | | 5 | | | | | 2 | | | |
| Photonyl ® LS | | | | | | | | | 2 | | |
| Panthenol | | | | | 1 | | | | | | |
| Bisabolol | | | | | 0.2 | | | | | | |
| Tocopherol/ Tocopheryl acetate | | | | | 1 | | | | | | |
| Neo Heliopan ® Hydro (Na salt) | | | | | | | | | 3 | | |
| Neo Heliopan ® AP (Na salt) | | 2 | | 2 | | 2 | | | | | 1 |
| Eusolex ® OCR | 6 | | 9 | | 5 | 7 | 9 | | 4 | | 7 |
| Neo Heliopan ® BB | | | | | | | | 1 | 1 | | 1 |
| Neo Heliopan ® MBC | | 2 | | 1 | | | | 3 | 1 | | 3 |
| Neo Heliopan ® OS | 2 | | | | | | | 7 | | | |
| Neo Heliopan ® E1000 | | 4 | | | | 5 | | | | | |
| Neo Heliopan ® AV | | 4 | 7.5 | 5 | | | 5 | 4 | 7.5 | | |
| Uvinul ® T 150 | 1 | | | | | | | 1.3 | 1 | | 1 |
| Parsol ® 1789 | 1 | | | | | | | 2 | | | 1 |
| Z-Cote ® HP 1 | 7 | 2 | 5 | | 7 | 5 | | | 6 | 2 | |
| Eusolex ® T 2000 | 5 | 2 | | 10 | | 10 | | | 2 | | |
| Veegum ® Ultra | 1.5 | | 1.5 | | | 1.5 | 1.2 | | 1 | | |
| Keltrol ® T | 0.5 | | 0.5 | | | 0.5 | 0.4 | | 0.5 | | |
| Pemulen ® TR 2 | | 0.3 | | 0.3 | | | 0.1 | 0.2 | | | 0.3 |
| Ethanol | | 5 | | 8 | | | | | | | |
| Butylene glycol | 1 | | 3 | | 3 | | | | | 8 | 1 |
| Glycerin | 2 | 4 | 3 | 3 | | 3 | 3 | 3 | 5 | | 3 |

Water ad 100, Preservative q.s., NaOH q.s.

| O/W care emulsions | | | | | | | | | | | |
|---|---|---|---|---|---|---|---|---|---|---|---|
| Component | 67 | 68 | 69 | 70 | 71 | 72 | 73 | 74 | 75 | 76 | 77 |
| L = Emulsion, C = Cream | C | C | C | L | C | L | L | C | L | C | C |
| Dehymuls ® PGPH | | 2 | | | | | | | | | |
| Generol ® R | | | 1 | | | | | | | | |
| Hostaphat ® KL 340 N | | | | | | | | | 2 | | |
| Eumulgin ® Prisma | 0.4 | 0.6 | 0.5 | 0.5 | 0.4 | 0.4 | 1 | 0.3 | 0.1 | 0.1 | 0.1 |
| Emulgade ® PL 68/50 | | 2.5 | | | | | | | 4 | | |
| Tego ® Care CG | | | | | | | | | | | 2 |
| Tego ® Care 450 | | | | | | | | | 5 | | |
| Cutina ® MD | | 1 | 6 | 5 | | 4 | | | 6 | | |
| Lanette ® 14 | | | 1 | | | | 2 | | | | 4 |
| Lanette ® O | 4.5 | | 4 | | 1 | 2 | | | | | 2 |
| Novata ® AB | | 1 | | | | | | | | | 1 |
| Lanolin, anhydrous, USP | | | | | | | | 5 | | | |
| Cetiol ® SB 45 | | | 1.6 | | | 2 | | | | | |
| Myritol ® PC | | | | | 5 | | | | | | |
| Myritol ® 331 | 2 | 5 | | | | 6 | | 12 | | | |
| Finsolv ® TN | | | | | | 2 | | 8 | | | |
| Cetiol ® CC | 4 | | | | 4 | | | | | | 5 |
| Cetiol ® Sensoft | | 6 | | 5 | | 4 | 4 | | | | |
| Cetiol ® OE | | | 7 | | | | | | 3 | | |
| Dow Corning DC ® 245 | | | 2 | | 1 | | | | | | |
| Dow Corning DC ® 2502 | | | | 2 | 1 | | | | | | |
| Prisorine ® 3758 | | | | | 1 | | | | | | |
| Wacker AK ® 350 silicone oil | 0.5 | 0.5 | 0.5 | | | 1 | 4 | | | | |
| Cetiol ® 868 | | | | 2 | | 4 | | | | | |
| Cetiol ® J 600 | 2 | | 3 | 3 | 2 | | | | 5 | | |
| Ceraphyl ® 45 | | | | | | | 3 | | | | |
| Cetiol ® SN | | | | 5 | | | | | | | |
| Cetiol ® B | | | | | | | | | 2 | | |
| Eutanol ® G | | 2 | | 5 | | | | | | | |
| Cetiol ® PGL | | | | 7 | | | | | 5 | 5 | |
| Dry Flo ® Plus | 5 | | | | | 1 | | | | | |
| SFE 839 | 5 | | | | | | | | | | 2 |
| Almond oil | | | | | | 1 | | | | | |
| Insect Repellent ® 3535 | | 2 | 4 | | 2 | | | | 3 | | |
| N,N-Diethyl-m-toluamide | | | 2 | | | | | | 3 | | |
| Photonyl ® LS | 2 | 2 | | | | 2 | | | | | |
| Panthenol | | | | | 1 | | | | | | |
| Bisabolol | | | | | 0.2 | | | | | | |
| Tocopherol/ Tocopheryl acetate | | | | | 1 | | | | | | |
| Veegum ® Ultra | | | | | | | | | 1 | | |
| Keltrol ® T | | | 0.4 | | | | | | 0.5 | | |
| Pemulen ® TR 2 | 0.3 | | | | | | | 0.3 | | | |
| Carbopol ® Ultrez 10 | | | 0.3 | 0.2 | | 0.2 | | | | 0.1 | 0.3 |
| Cosmedia SP | | 0.3 | | | 0.2 | | | | | | 0.2 |
| Aluminum Chlorohydrate | | 7 | | | | | | | | | |
| Ethanol | | | | | | | | | | 10 | |
| Butylene glycol | | | 4 | 3 | | 2 | 5 | 2 | | | |
| Glycerin | 2 | 5 | 5 | | 3 | 3 | 2 | | 4 | | 3 |
| Water, preservative, NaOH | ad 100, q.s., pH 6.5-7.5 | | | | | | | | | | |

| O/W care emulsions | | | | | | | | | | | |
|---|---|---|---|---|---|---|---|---|---|---|---|
| Component | 78 | 79 | 80 | 81 | 82 | 83 | 84 | 85 | 86 | 87 | 88 |
| L = Emulsion, C = Cream | C | C | L | C | L | C | L | L | L | L | C |
| Eumulgin ® VL 75 | | 3 | | | 1 | | | | | | 2 |
| Generol ® R | | | | | 2 | | | | | | |
| Eumulgin ® B2 | | | | | | | | 1 | | | |
| Tween ® 60 | | | | | | | | 1 | | | |
| Cutina ® E 24 | | | 2 | | | | | | | | |
| Eumulgin ® Prisma | 0.5 | 0.2 | 0.3 | 0.1 | 1 | 0.5 | 0.2 | 1 | | 0.7 | 0.5 | 1 |
| Lanette ® E | | | | | | | | | | | 0.1 |
| Amphisol ® K | | 1 | | | | | 0.1 | | | | |
| Sodium stearate | | | | | | | | | | | |
| Emulgade PL 68/50 | | 6 | | | | 5 | | | | | 4 |
| Tego ® Care 450 | | | | | | | 4 | | | | |
| Cutina ® MD | 3 | | 3 | 8 | 6 | 8 | | | 4 | | |
| Lanette ® 14 | | 2 | | | | 2 | | 1 | | | |
| Lanette ® O | 2 | | 2 | | 3 | 1 | | 1 | 1 | 6 | |
| Lanolin, anhydrous, USP | | | | | 4 | | | | | | |
| Cetiol ® SB 45 | | | | | 2 | | | | | | |
| Cetiol ® Sensoft | 6 | | 2 | | | | | 3 | 5 | 3 | |
| Cegesoft ® C 17 | 4 | | | | | | | | | | |
| Myritol ® PC | | | | 5 | | 5 | | | | | |
| Myritol ® 331 | 5 | | 5 | | 7 | | 5 | | | | |
| Finsolv ® TN | | 5 | | 5 | | 3 | | | | | 1 |
| Cetiol ® CC | | | 2 | | | | | | | | 2 |
| Cetiol ® OE | | | | 2 | | 2 | 5 | | | | |
| Dow Corning DC ® 245 | | 2 | | 1 | | | | 8 | | | 2 |
| Dow Corning DC ® 2502 | | 1 | | 1 | | | | | | 3 | |
| Prisorine ® 3758 | 3 | | | | | | | | 2 | | |
| Wacker AK ® 350 silicone oil | | | | 1 | | | | | | 1 | |
| Cetiol ® 868 | | 2 | | | | | | | | | |
| Cetiol ® J 600 | | 2 | | | | | | | | | |
| Ceraphyl ® 45 | | | | | | 3 | | | | | |
| Cetiol ® SN | | | | | | | | | | | |
| Cetiol ® B | | | 5 | | 5 | | 4 | | | 3 | |
| Eutanol ® G | | 3 | 5 | 5 | | | | | | | |
| Cetiol ® PGL | | | | | | | 5 | 2 | | | |
| Dry Flo ® Plus | | 1 | | | | | | | | 1 | |
| SFE 839 | 1 | 1 | | | | | | | | | |
| Almond oil | | | | | 2 | | | | | | |
| Photonyl ® LS | | | | | 2 | | | | | | |
| Panthenol | | | | | 1 | | | | | | |
| Bisabolol | | | | | 0.2 | | | | | | |
| Tocopherol/ Tocopheryl acetate | | | | | 1 | | | | | | |
| veegum ® Ultra | | | | | | 1 | | | | | |
| Keltrol ® T | | | | | | | 0.5 | | | | |
| Carbopol ® ETD 2001 | | 0.3 | | 0.3 | | 0.5 | 0.2 | 0.2 | | | |
| Pemulen ® TR 2 | | | 0.3 | | 0.3 | | | | | | 0.5 |

| O/W care emulsions | | | | | | | | | | | |
|---|---|---|---|---|---|---|---|---|---|---|---|
| Component | 78 | 79 | 80 | 81 | 82 | 83 | 84 | 85 | 86 | 87 | 88 |
| Ethanol | | 5 | | 8 | | | | | | | 10 |
| Butylene glycol | 5 | | 2 | 3 | 3 | | | | | 8 | |
| Glycerin | 2 | 4 | 3 | 3 | | 7 | 5 | 3 | 5 | | |

Water ad 100, Preservative q.s., NaOH (pH 6.5-7.5)

| Spray formulations | | | |
|---|---|---|---|
| Component | 97 | 98 | 99 |
| | Sunscreen spray | | |
| | S | S | S |
| Eumulgin ® Prisma | 1 | 1 | 1 |
| Eumulgin ® VL 75 | | | 2 |
| Emulgade ® PL 68/50 | 2.5 | 1 | |
| Antaron V 220 | | 1 | 1 |
| Cetiol ® Sensoft | 4 | 4 | 5 |
| Myritol ® 331 | 3 | 3 | 3 |
| Finsolv ® TN | | | 8 |
| Cetiol ® CC | 2 | 2 | 4 |
| Cetiol ® OE | 2 | | |
| Photonyl ® LS | | 2 | 2 |
| Panthenol | | 1 | 1 |
| Bisabolol | | 0.2 | 0.2 |
| Tocopherol/tocopheryl acetate | | 1 | 1 |
| Neo Heliopan ® Hydro (Na salt) | | 3 | |
| Neo Heliopan AP (Na salt) | | | 1 |
| Eusolex ® OCR | | | 3 |
| Neo Heliopan ® BB | | 1 | |
| Neo Heliopan ® MBC | | 1 | 1 |
| Neo Heliopan ® AV | | 7.5 | 2 |
| Uvinul ® T 150 | | 1 | |
| Parsol ® 1789 | | 1 | |
| Z-Cote ® HP 1 | | 2 | 2 |
| Eusolex ® T 2000 | | 2 | 2 |
| Veegum ® Ultra | | | 1.5 |
| Laponite ® XLG (synthetic layered silicate) | | 1.5 | |
| Keltrol ® T | | | 0.5 |
| Pemulen ® TR 2 | 0.2 | | |
| Insect Repellent ® 3535 | 1 | | |
| N,N-Diethyl-m-toluamide | 1 | | |
| Ethanol | | 5 | |
| Butylene glycol | | 2 | 1 |
| Glycerin | 2 | | 3 |
| Water/Preservative/NaOH | | ad 100 | |

| Formulations 1 to 13 | | | | | | | | | | | | | |
|---|---|---|---|---|---|---|---|---|---|---|---|---|---|
| INCI components (Trade name) | 1 | 2 | 3 | 4 | 5 | 6 | 7 | 8 | 9 | 10 | 11 | 12 | 13 |
| Glyceryl Stearate, Ceteareth-20, Ceteareth-12, Cetearyl Alcohol, Cetyl Palmitate (Emulgade ® SE) | | | | | | | | | | | | 10.7 | 5.1 |
| Ceteareth-20 (Eumulgin ® B2) | | | | | | | | | | | | 5.8 | 3.4 |
| Cetearyl Glucoside, Cetearyl Alcohol (Emulgade ® PL 68/50) | 1 | | 1 | 1 | | 2 | 2 | | | 2 | | 2 | |
| Polyglyceryl-2 Dipolyhydroxystearate, Lauryl Glucoside, Glycerin (Eumulgin ® VL 75) | | 1 | | 1 | | | | 3 | | 2.5 | | | |

-continued

| Formulations 1 to 13 | | | | | | | | | | | | | |
|---|---|---|---|---|---|---|---|---|---|---|---|---|---|
| INCI components (Trade name) | 1 | 2 | 3 | 4 | 5 | 6 | 7 | 8 | 9 | 10 | 11 | 12 | 13 |
| Disodium Cetearyl Sulfosuccinate (Eumulgin ® Prisma) | 1 | 1 | 1 | 0.5 | 1 | 1 | 0.5 | 1 | 1 | 1 | 1 | 1 | 0.5 |
| Dicaprylyl Carbonate (Cetiol ® CC) | 5 | 5 | | | | | | 4 | | 5 | 3 | 4 | |
| Cocoglycerides (Myritol ® 331) | 3 | 4 | | 4 | 4 | | | | 5 | | | 3 | 3 |
| Dicaprylyl Ether (Cetiol ® OE) | | | | | 5 | | 3 | | 2 | | | | |
| Dibutyl Adipate (Cetiol ® B) | | | | 4 | | | | 4 | | 4 | | | |
| Hydrogenated Dimer Dilinoleyl/Dimethylcarbonate Copolymer (Cosmedia ® DC) | 1 | 1 | 1 | 1 | 1 | 1.5 | 1.5 | 2 | 3 | 2 | 1.5 | 2 | 2 |
| Propylheptyl Caprylate (Cetiol ® Sensoft) | | | 5 | | 5 | | | | | | | 5 | |
| Tocopherol | 1 | 1 | 1 | 1 | 1 | 1 | 1 | 1 | 1 | 1 | 1 | 1 | 1 |
| Zinc oxide, nanoized, coated | 5 | 5 | 5 | 5 | 5 | | 2 | | 5 | 3 | | | |
| Titanium dioxide, nanoized, coated | | | | 5 | 5 | | 2 | 3 | 5 | 2 | | | |
| Ethylhexyl Methoxycinnamate | 7.5 | 7.5 | 7.5 | | | 3 | 1 | 3 | 5 | | 5 | 5 | |
| Octocrylene | 9 | 9 | 9 | | | 2 | 1 | | | | 2 | | 1.5 |
| Butyl Methoxydibenzoylmethane | | | | | | 2 | 2 | | | 1 | 2 | 2 | |
| 4-Methylbenzylidene Camphor | | | | | | | 2 | | | | | | 2 |
| Ethylhexyl triazone | | | | | | 1 | 1 | 2 | | | 1 | | |
| Diethylhexyl Butamido Triazone | | | | | | 1 | 1 | 2 | | | 1 | 2 | |
| Phenylbenzimidazole Sulfonic Acid as Na salt, 15% aqueous solution | | | | | | | | | | | | | 13.3 |
| Glycerin | 3 | 3 | 3 | 3 | 3 | 3 | 3 | 3 | 3 | 3 | 3 | 5 | 5 |
| Magnesium aluminium silicate (and) cellulose Gum | 0.75 | 0.75 | | 0.5 | 0.5 | | 0.5 | | | 0.35 | | | |
| Xanthan Gum | 0.25 | 0.25 | | 0.5 | 0.5 | | 0.5 | | | 0.35 | | | |
| Sodium Polyacrylate (Cosmedia ® SP) | | | 0.1 | | | 0.1 | 0.2 | | | | 0.1 | | |
| Acrylates/C10-30 Alkyl Acrylate Crosspolymer | | | | | | | | | 0.2 | 0.1 | | | |
| Water, Perfume, Preservatives | q.s. | q.s. | q.s. | q.s. | q.s. | q.s. | q.s. | q.s. | q.s. | q.s. | q.s. | q.s. | q.s. |

| Formulations 14 to 26 | | | | | | | | | | | | | |
|---|---|---|---|---|---|---|---|---|---|---|---|---|---|
| INCI components (Trade name) | 14 | 15 | 16 | 17 | 18 | 19 | 20 | 21 | 22 | 23 | 24 | 25 | 26 |
| Glyceryl Stearate, Ceteareth-20, Ceteareth-12, Cetearyl Alcohol, Cetyl Palmitate (Emulgade ® SE) | 3.7 | 3.7 | | | | | | | | | | 4.9 | 4.1 |
| Ceteareth-12 (Eumulgin ® B1) | 1.3 | 1.3 | | | | | | | | | | | |
| Ceteareth-20 (Eumulgin ® B2) | | | | | | | | | | | | 1.1 | 0.9 |
| Cetearyl Glucoside, Cetearyl Alcohol (Emulgade ® PL 68/50) | | | 5 | 1 | 1 | 1 | 1 | 3 | | | | | |
| Polyglyceryl-2 Dipolyhydroxystearate, Lauryl Glucoside, Glycerin (Eumulgin ® VL 75) | | | | | | | | | 3 | 5 | 5 | | |
| Disodium Cetearyl Sulfosuccinate (Eumulgin ® Prisma) | 0.1 | 0.1 | 0.1 | 0.25 | 0.25 | 0.25 | 0.25 | 0.25 | 0.2 | 0.2 | 0.3 | 0.3 | 0.3 |
| Potassium Cetyl Phosphate | | | 0.5 | | | | | | | | | | |
| Dicaprylyl Carbonate (Cetiol ® CC) | 5 | | 5 | | | | | | 2.5 | 4 | 4 | 5 | 5 |
| Coco-Caprylate/Caprate (Cetiol ® LC) | | | | 1 | 1 | 1 | 1 | 1 | | | | | |
| Caprylic/Capric Triglyceride (Myritol ® 312) | | | | 1 | 1 | 1 | 1 | 1 | | | | | |
| Cocoglycerides (Myritol ® 331) | | | | | | | | | | 4 | 4 | | |

-continued

| Formulations 14 to 26 | | | | | | | | | | | | | |
| --- | --- | --- | --- | --- | --- | --- | --- | --- | --- | --- | --- | --- | --- |
| INCI components (Trade name) | 14 | 15 | 16 | 17 | 18 | 19 | 20 | 21 | 22 | 23 | 24 | 25 | 26 |
| Cetearyl Isononanoate (Cetiol ® SN) | 3 | 3 | 3.5 | | | | | | | | | | |
| Octyldodecanol (Eutanol ® G) | | | | | | | | | 3.5 | 2 | 2 | | |
| Propylheptyl Caprylate (Cetiol ® Sensoft) | | | | 1 | 1 | 1 | 1 | 1 | | | | | |
| Olus (Cegesoft ® PS6) | | 1.5 | 1.5 | | | | | | | | | | |
| Passiflora Incarnata (Cegesoft ® PFO) | 1.5 | | | | | | | | | | | | |
| Dimethicone | | | | 0.5 | 0.5 | 0.5 | 0.5 | 0.5 | | | | | |
| Dimer Distearyltricarbonate (Cosmedia ® DC) | 1 | | 1.5 | | | | | 1.5 | | 2.5 | 2.5 | | 0.5 |
| Triethyl Citrate (Hydagen ® C.A.T) | | | | | | | | | | | | 1.5 | |
| Tocopherol | | | | | | | | | 0.5 | 0.5 | 0.5 | | |
| Tocopheryl Acetate | 0.5 | 0.5 | | | | | | | | | | | |
| Ethanol | | | | | | | | | | | 5 | | |
| Aluminum Chlorohydrate (Locron L) | | | | | | | | | | | | | 40 |
| Chitosan (Hydagen ® DCMF) | | | | | | | | | | | 0.1 | | |
| Glycolic Acid | | | | | | | | | | | 0.04 | | |
| Glycerin | 2 | 2 | 2 | 3 | 3 | 3 | 3 | 3 | 2 | 2 | 2 | 3 | 2 |
| Potassium hydroxide, 20% aqueous solution | | | | | | 0.3 | 0.2 | 0.1 | 0.4 | 0.3 | 0.5 | | |
| Glycerin, Glyceryl Polyacrylate (Hispagel ® 50) | | | | | | | | | | 10 | | | |
| Carbomer | | | | | | | 0.1 | | 0.2 | | 0.2 | | |
| Sodium Polyacrylate (Cosmedia ® SP) | | | | 0.15 | | | | | | | | | |
| Acrylates/C10-30 Alkyl Acrylate Crosspolymer | | | | | | 0.15 | | 0.05 | | | | | |
| Water, Perfume, Preservatives | q.s. | q.s. | q.s. | q.s. | q.s. | q.s. | q.s. | q.s. | q.s. | q.s. | q.s. | q.s. | q.s. |

| Formulations 27 to 33 (formulations for antiperspirant/deodorant) | | | | | | | |
| --- | --- | --- | --- | --- | --- | --- | --- |
| INCI components (Trade name) | 27 | 28 | 29 | 30 | 31 | 32 | 33 |
| Glyceryl Stearate, Ceteareth-20, Ceteareth-12, Cetearyl Alcohol, Cetyl Palmitate (Emulgade ® SE) | 6 | | 4.5 | | | 6 | |
| Ceteareth-20 (Eumulgin ® B2) | | | | 1 | | | |
| Cetearyl Isononanoate, Glyceryl Stearate, Ceteareth-20, Ceteareth-12, Cetearyl Alcohol, Cetyl Palmitate (Emulgade ® CM) | | | | | 20 | | |
| Polyglyceryl-3 Diisostearate Lameform TGI | | 3 | | | | | |
| Cocoglycerides (Novata ® AB) | | | | | | | 4 |
| Stearyl alcohol (Lanette 18) | | | | 14.7 | | | |
| Hydrogenated Castor Oil (Cutina ® HR) | | | | 3.7 | | | 6.5 |
| Polyglyceryl-2 Dipolyhydroxystearate (Dehymuls ® PGPH) | | 1 | | | | | |
| Disodium Cetearyl Sulfosuccinate (Eumulgin ® Prisma) | 0.3 | 0.05 | 0.2 | 0.4 | 0.1 | 0.3 | 0.2 |
| Behenyl Alchol (Lanette ® 22) | 2 | | | | | 4 | |
| Dicaprylyl Carbonate (Cetiol ® CC) | | 3 | | | | | |
| Dicaprylylether (Cetiol ® OE) | 2 | | | 4 | | 3 | 9 |
| Propylheptyl Caprylate (Cetiol ® Sensoft) | | 5 | | 14 | | | 10 |
| Cyclopentasiloxane | 3 | | | 30 | | 2 | 4 |
| Cyclopentasiloxane and Dimethicone/ Vinyldimethicone Crosspolymer SFE 839 (GE Bayer) | | 3 | | | | | |
| Dimethicone | 1 | | | | | | |
| Dimer Distearyltricarbonate (Cosmedia ® DC) | 1 | 1 | 1 | 1 | 1 | 1 | 1 |
| Triethyl Citrate (Hydagen ® C.A.T) | | | 2 | | | | |
| PEG-40 Hydrogenated Castor Oil | | | | | 1 | | |
| Tocopheryl Acetate | | | | 1 | | | |
| Aluminium Zirconium Tetrachlorohydrex GLY (Rezal 36) | 30 | 40 | | 22.9 | | 30 | 25 |
| Aluminum Chlorohydrate (Locron L) | | | 10 | | | | |
| Chitosan (Hydagen ® DCMF) | | 0.05 | | | | | |
| Glycolic Acid | | 0.02 | | | | | |
| Glycerin | | | 5 | 5 | | | |

| Formulations 27 to 33 (formulations for antiperspirant/deodorant) | | | | | | | |
|---|---|---|---|---|---|---|---|
| INCI components (Trade name) | 27 | 28 | 29 | 30 | 31 | 32 | 33 |
| Propylene Carbonate (Fluka) | | | | | | | 0.5 |
| Quaternium-18 Hectorite (Bentone 18) | | | | | | | 1 |
| Talc (Merck) | | | | | | 5 | 5 |
| MgSO4 × 7H2O | | | 1 | | | | |
| Water Phase II | 46.7 | | 35 | | | | |
| Water, Perfume, Preservatives | q.s. | q.s. | q.s. | q.s. | q.s. | q.s. | q.s. |

27—Antiperspirant/deodorant cream/28—Antiperspirant cream (W/O)/29—Antiperspirant/deodorant spray; 30—Antiperspirant stick with vitamin E/31—Deodorant wipe formulation/32—Antiperspirant cream; 33—Antiperspirant "Soft Solid" cream

| O/W sunscreen emulsions | | | | | | | | | | | |
|---|---|---|---|---|---|---|---|---|---|---|---|
| Component | 12 | 13 | 14 | 15 | 16 | 17 | 18 | 19 | 20 | 21 | 22 |
| L = Emulsion, C = Cream, S = Spray | L | C | L | C | L | C | S | C | C | L | L |
| Eumulgin ® VL 75 | 2 | | | 3 | | 4 | | | 1 | | |
| Dehymuls ® PGPH | | 1 | | | | | 0.5 | | | | |
| Disodium Cetearyl Sulfosuccinate (Eumulgin ® Prisma) | 0.5 | 0.6 | 0.5 | 0.7 | 0.5 | 0.5 | 0.1 | 0.2 | 0.1 | 0.5 | 0.5 |
| Eumulgin ® SG | | | | | | | 0.1 | | | | |
| Emulgade ® PL 68/50 | | 2 | 1 | | | 3 | | | | | |
| Tego ® Care 450 | | 2 | | | | | | 2 | | | |
| Cutina ® MD | | | | 2 | 1 | 3 | | | | | 1 |
| Lanette ® 14 | | 1 | | | | | | | | | |
| Lanette ® O | | | 2 | | | | 2 | 1 | 1 | | |
| Cutina ® PES | 1 | 1 | 2 | | | | | 1 | | | |
| Allianz ® OPT | 1 | | | 1 | 1 | | 2 | | | | 2 |
| Cosmedia ® DC | | 1.5 | 2 | | 1.5 | 2 | | 1.5 | 1.5 | | |
| Lanolin, anhydrous, USP | | | | | 1 | 1 | | | | | |
| Propylheptyl Caprylate (Cetiol ® Sensoft) | 6 | 2 | 4 | 7 | 3 | 7 | 6 | 6 | 4 | 4 | 5 |
| Myritol ® PC | | | | | | | 5 | | | | |
| Myritol ® 331 | 6 | | 4 | | | 5 | 8 | | 10 | 8 | |
| Finsolv ® TN | | | | 5 | | | | 3 | 3 | | |
| Cetiol ® CC | 6 | | 6 | | 5 | 5 | | | | | |
| Cetiol ® OE | | | | 2 | | | | | | | 2 |
| Dow Corning DC ® 244 | | 2 | | 1 | | | | | | | |
| Dow Corning DC ® 2502 | | 1 | | 1 | | 3 | | | | | |
| Ceraphyl ® 45 | | | | | | | | | | 2 | 2 |
| Wacker AK ® 350 silicone oil | | | | | | | 1 | | | | |
| Cetiol ® 868 | | 2 | | | | | | | | | |
| Cetiol ® J 600 | | 2 | | | | | | | | | |
| Cetiol ® B | 4 | | 4 | | | | | 4 | | | |
| Eutanol ® G | | 3 | | | | 3 | | | | | |
| Eutanol ® G 16 S | 3 | | | | | | | | | | |
| Cetiol ® PGL | | | | | | | | | 2 | | |
| Photonyl ® LS | | | | | | | | | | 2 | |
| Panthenol | | | | | | 1 | | | | | |
| Bisabolol | | | | | | 0.2 | | | | | |
| Tocopherol/tocopheryl acetate | | | | | | 1 | | | | | |
| Neo Heliopan ® Hydro (Na salt) | | | | | | | | | | 3 | |
| Eusolex ® OCR | 6 | | 9 | | 5 | 7 | 9 | | 4 | | 7 |
| Neo Heliopan ® AP (Na salt) | | | | | 0.5 | | 1 | | | | |
| Neo Heliopan ® BB | | | | | | | | 1 | 1 | | 1 |
| Neo Heliopan ® MBC | | | 2 | | 1 | | | 3 | 1 | | 3 |
| Neo Heliopan ® OS | 2 | | | | | | | | 7 | | |
| Neo Heliopan ® E1000 | | | 4 | | | | | 5 | | | |
| Neo Heliopan ® AV | | 4 | 7.5 | 5 | | | | 5 | 4 | 7.5 | |
| Uvinul ® A PLUS | | | | | 1 | | 2 | | | | |
| Uvinul ® T 150 | 1 | 1 | | | | | | | 1.3 | 1 | 1 |
| Tinosorb ® M | | 2 | | | 2 | 2 | | | | | |
| Tinosorb ® S | | 1 | | | 2 | 2 | | | | | |
| Parsol ® 1789 | 1 | | | | | | | | 2 | | 1 |
| Z-Cote ® HP 1 | 7 | 2 | 5 | | | 7 | 5 | | 6 | 2 | |
| Eusolex ® T 2000 | 5 | 2 | | 10 | | | 10 | | | 2 | |
| Veegum ® Ultra | 1.5 | | 1.5 | | | 1.5 | 1.2 | | 1 | | |
| Keltrol ® T | 0.5 | | 0.5 | | | 0.5 | 0.4 | | 0.5 | | |
| Cosmedia ® SP | | | 0.2 | 0.3 | | | 0.1 | | | 0.2 | |
| Pemulen ® TR 2 | | 0.3 | | 0.3 | | | | 0.2 | | | 0.3 |
| Ethanol | | 5 | | 8 | | | | | | | |
| Butylene glycol | 1 | | | 3 | 3 | | | | | 8 | 1 |
| Glycerin | 2 | 4 | 3 | 3 | | 3 | 3 | 3 | 5 | | 3 |

Water ad 100/Preservative q.s./NaOH q.s.

| O/W care emulsions | | | | | | | | | | | |
|---|---|---|---|---|---|---|---|---|---|---|---|
| Component | 34 | 35 | 36 | 37 | 38 | 39 | 40 | 41 | 42 | 43 | 44 |
| L = Emulsion, C = Cream | C | C | L | C | L | C | L | L | L | L | C |
| Eumulgin ® VL 75 | | 5 | | 4 | | | | | | | 2 |
| Generol ® R | | | | | 2 | | | | | | |
| Eumulgin ® Prisma | 0.5 | 0.5 | 0.1 | 0.5 | 1 | 0.4 | 0.5 | 0.2 | 0.1 | 1 | 1 |
| Emulgade ® PL 68/50 | | 2 | | 2 | | | | 3 | 4 | | |
| Tego ® Care 450 | | | 1 | | | | | | | 1 | |

| O/W care emulsions | 1 | 2 | 3 | 4 | 5 | 6 | 7 | 8 | 9 | 10 | 11 |
|---|---|---|---|---|---|---|---|---|---|---|---|
| Cutina ® MD | 2 | 1 | 1 | 1 |  | 5 |  |  |  | 2 |  |
| Lanette ® 14 |  |  |  |  | 1 |  |  | 2 |  | 1 |  |
| Lanette ® O | 2 |  |  | 2 | 1 | 3 | 1 |  | 1 | 1 | 3 |
| Cutina ® PES | 1 | 2 |  | 3 | 1 |  |  |  |  |  | 3 |
| Novata ® AB |  |  |  |  |  |  |  |  | 1 | 1 |  |
| Lanolin, anhydrous, USP |  |  |  |  |  | 4 |  |  |  |  |  |
| Cosmedia ® DC |  |  | 2 |  |  | 1.5 |  |  | 1 | 1 |  |
| Cetiol ® SB 45 |  |  |  |  |  |  | 2 |  |  |  |  |
| Cegesoft ® C 17 | 2 |  |  |  |  |  |  |  |  |  |  |
| Cetiol ® Sensoft | 5 | 5 | 4 | 4 | 3 | 4 | 5 | 4 | 5 | 10 | 2 |
| Myritol ® PC | 6 |  |  |  |  | 5 |  |  |  |  |  |
| Myritol ® 331 | 2 |  | 5 |  |  |  | 2 |  |  |  | 3 |
| Finsolv ® TN |  |  |  | 3 | 5 |  |  | 3 | 3 |  | 1 |
| Cetiol ® CC |  |  |  | 3 |  |  | 4 | 3 |  |  |  |
| Cetiol ® OE |  |  |  |  | 2 |  | 2 |  | 5 |  |  |
| Dow Corning DC ® 245 |  | 2 |  |  | 1 | 4 |  |  |  | 8 | 2 |
| Dow Corning DC ® 2502 |  | 1 |  |  | 1 |  |  |  |  |  | 3 |
| Prisorine ® 3758 | 3 |  |  |  |  |  |  |  |  |  | 2 |
| Wacker AK ® 350 silicone oil |  |  |  |  | 1 |  |  |  |  |  | 1 |
| Cetiol ® 868 |  | 2 |  |  |  |  |  |  |  |  |  |
| Cetiol ® J 600 |  | 2 |  | 2 |  |  |  |  |  |  |  |
| Ceraphyl ® 45 |  |  |  |  |  |  | 3 |  |  |  |  |
| Cetiol ® SN |  |  | 5 |  |  |  |  |  |  |  |  |
| Cetiol ® B |  |  | 5 |  |  | 5 |  | 4 |  |  | 3 |
| Eutanol ® G |  | 3 | 5 |  | 5 |  |  |  |  |  |  |
| Cetiol ® PGL |  |  |  |  |  |  |  |  | 5 | 2 |  |
| Dry Flo ® Plus |  | 1 |  |  |  |  |  |  |  |  | 1 |
| SFE 839 | 1 | 1 |  |  |  |  |  |  |  |  |  |
| Almond oil |  |  |  |  |  | 2 |  |  |  |  |  |
| Photonyl ® LS |  |  |  |  |  | 2 |  |  |  |  |  |
| Panthenol |  |  |  |  |  | 1 |  |  |  |  |  |
| Bisabolol |  |  |  |  |  | 0.2 |  |  |  |  |  |
| Tocopherol/Tocopheryl acetate |  |  |  |  |  | 1 |  |  |  |  |  |
| Veegum ® Ultra |  |  |  |  |  |  |  |  | 1 |  |  |
| Keltrol ® T |  |  |  |  |  |  |  |  | 0.5 |  |  |
| Cosmedia ® SP | 0.5 |  |  |  |  | 0.5 | 0.5 | 0.2 |  |  | 0.5 |
| Carbopol ® ETD 2001 |  | 0.3 |  | 0.3 |  |  |  |  |  |  |  |
| Pemulen ® TR 2 |  |  | 0.3 |  | 0.3 |  |  |  |  |  |  |
| Ethanol |  | 5 |  | 8 |  |  |  |  |  |  | 10 |
| Butylene glycol | 5 |  | 2 | 3 | 3 |  |  |  |  | 8 |  |
| Glycerin | 2 | 4 | 3 | 3 |  | 7 | 5 | 3 | 5 |  |  |
| Water, Preservative, NaOH | ad 100, q.s. (pH 6.5-7.5) | | | | | | | | | | |

| Component | 1 | 2 | 3 | 4 | 5 | 6 | 7 |
|---|---|---|---|---|---|---|---|
| Ethanol |  | 4.00 |  | 3.00 |  | 4.50 |  |
| Dem. water (add to) | 100 | 100 | 100 | 100 | 100 | 100 | 100 |
| Phenonip | 1.00 | 1.00 | 1.00 | 1.00 | 1.00 | 1.00 | 1.00 |
| Glycerin 99% | 3.00 | 3.00 | 3.00 | 3.00 | 3.00 | 3.00 | 3.00 |
| Ultragel ® 300 (Polyquaternium-37) | 0.8 | 1.00 | 1.50 | 0.90 | 2.00 | 1.50 | 0.75 |
| Eumulgin ® VL 75 (Lauryl Glucoside (and) Polyglyceryl-2-dipolyhydroxystearate (and) glycerin) | 1.80 | — | 0.80 | — | — | — | — |
| Emulgade ® PL 68/50 (Cetearyl Glucoside (and) Cetearyl Alcohol) | — | — | — | — | — | 3.00 | — |
| Eumulgin ® Prisma (Disodium Cetearyl Sulfosuccinate) | 0.10 | 0.12 | 0.30 | 0.10 | 0.30 | 0.10 | 0.08 |
| Cutina ® PES (Pentaerythrityl Distearate) | 2.50 | 3.50 | 1.70 | 4.00 | 2.00 | 4.00 | 5.00 |
| Cetiol ® J600 (Oleyl Erucate) | 2.00 | — | 5.00 | — | — | 1.00 | 3.00 |
| Cetiol ® CC (Dicaprylyl Carbonate) | 3.50 | — | 4.00 | 4.00 | 2.50 | 3.00 | 4.00 |
| Cetiol ® PGL (Hexyldecanol (and) Hexyldecyl Laurate) | — | 2.00 | — | 4.00 | 5.00 | 5.00 | 1.00 |
| Tegosoft ® DEC (Diethylhexyl Carbonate) | — | — | — | 2.50 | — | — | 3.00 |
| DC ® 345 (Cyclopentasiloxane) | 4.00 | — | — | — | 2.00 | — | — |
| Cetiol ® B (Dibutyl Adipate) | 5.00 | 3.5 | 5.00 |  |  | 2.00 |  |
| Myritol ® 331 (Cocoglycerides) | 3.00 | — | — | — | — | 4.00 | 4.50 |
| Cetiol ® Sensoft (Propylheptyl Caprylate) | 3.00 | 3.00 | 5.00 | 2.00 | 7.00 | 5.00 | 3.00 |

| O/W care emulsions | | | | | | | |
|---|---|---|---|---|---|---|---|
| DHA (Dihydroxyacetone) | 2.00 | 1.00 | 2.50 | 1.00 | 2.00 | 2.00 | 3.50 |
| Uvinul ® T 150 (Ethylhexyl Triazone) | — | — | 1.00 | — | — | — | — |
| Tinosorb ® M (Methylene Bis-Benzotriazoyl Tetramethylbutylphenol) | — | 1.00 | 1.00 | — | — | — | — |
| Tinosorb ® S (Bis-Ethylhexyloxyphenol Methoxyphenyl Triazine) | — | 2.00 | — | — | 0.50 | — | — |
| Uvasorb ® HEB (Diethylhexyl Butamino Triazone) | — | — | — | — | 1.00 | — | — |
| Neo Heliopan ® AV (Ethylhexyl Methoxycinnamate) | — | 5.00 | 5.00 | — | 3.00 | — | — |
| Parsol ® 1789 (Butyl Methoxydibenzoylmethane) | — | 3.00 | 3.00 | — | 2.00 | — | — |
| Neo Heliopan ® 303 (Octocrylene) | — | 3.50 | 2.00 | — | — | — | — |

| Sunscreen spray | | | |
|---|---|---|---|
| Phase | Ingredient | INCI | % by wt. |
| I | Deionized water | Aqua | qs 100 |
| | Butylene Glycol | Butylene Glycol | 3.00 |
| II | Veegum Ultra | Magnesium Aluminum Silicate | 0.50 |
| | Keltrol T | Xanthan Gum | 0.30 |
| III | Eumulgin ® VL 75 | Lauryl Glucoside (and) Polyglyceryl-2-Dipolyhydroxystearate (and) Glycerin | 6.00 |
| | Eumulgin ® Prisma | Disodium Cetearyl Sulfosuccinate | 0.2 |
| | Cetiol ® CC | Dicaprylyl Carbonate | 3.50 |
| | Cetiol ® Sensoft | Propylheptyl Caprylate | 3.50 |
| | Cetiol ® AB | C12-15 Alkyl Benzoate | 7.00 |
| | Cetiol ® Sun | Titanium Dioxide Dispersion | 10.00 |
| | Preservative | | q.s. |
| | Perfume | | q.s. |

Viscosity: Brookfield, RVT, 20° C., Sp 4, 5 rpm 3500 mPas pH = 6.5

| Sun lotion | | | |
|---|---|---|---|
| | Ingredient | INCI | % by wt. |
| I | Myritol ® 331 | Cocoglycerides | 2.00 |
| | Cetiol ® SB 45 | Shea Butter | 1.00 |
| | Cosmedia Gel CC | Dicaprylyl Carbonate (and) Stearalkonium Hectorite | 2.00 |
| | Uvasorb ® HEB | Dioctyl Butamido Triazone | 3.00 |
| | Cetiol ® Sensoft | Propylheptyl Caprylate | 3.50 |
| | Neo Heliopan ® AV | Ethylhexyl Methoxycinnamate | 4.00 |
| | Neo Heliopan ® E1000 | Isoamyl p-Methoxycinnamate | 4.00 |
| | Neo Heliopan ® 303 | Octocrylene | 3.00 |
| | Copherol ® 1250 C | Tocopheryl Acetate | 0.25 |
| | Cosmedia ® DC | Hydrogenated Dimer Dilinoleyl/Dimethylcarbonate Copolymer | 2.00 |
| II | Cetiol ® Sun | Titanium Dioxide Dispersion | 6.00 |
| | Eumulgin ® Prisma | Disodium Cetearyl Sulfosuccinate | 0.15 |
| | Satiaxane CX 91 | Xanthan gum | 0.30 |
| | Eumulgin ® VL75 | Lauryl Glucoside (and) Polyglyceryl-2-Dipolyhydroxystearate (and) Glycerin | 3.0 |
| III | Deionized water | Water | 58.22 |
| | 2 NaEDTA | Disodium EDTA | 0.10 |
| | Liponic EG-1 | Glycereth-26 | 3.00 |
| IV | Tinosorb M | Methylene bis-benzotriazolyltetramethylbutylphenol | 3.00 |
| | Water | Water | 3.00 |
| | Preservative | | q.s. |
| | Perfume | | q.s. |

Viscosity: Brook. RVT, 20° C., spindle 5, 10 rpm 2560 mPas pH = 6.70

Sun lotion

| | Ingredient | INCI | % by wt. |
|---|---|---|---|
| I | Cetiol ® B | Bibutyl Adipate | 2.00 |
| | Cosmedia ® DC | Hydrogenated Dimer Dilinoleyl/Dimethylcarbonate Copolymer | 1.00 |
| | Cetiol ® Sensoft | Propylheptyl Caprylate | 2.00 |
| II | Neo Heliopan ® OS | Ethylhexyl Salicylate | 3.00 |
| | Tinosorb ® S | Bis-ethylhexyloxyphenol Methoxyphenyl Triazine | 2.50 |
| | Neo Heliopan ® AV | Ethylhexyl Methoxycinnamate | 6.00 |
| | Neo Heliopan ® 303 | Octocrylene | 8.00 |
| | Neo Heliopan ® 357 | Butyl Methoxydibenzoylmethane | 2.50 |
| III | Cosmedia ® Gel CC | Dicaprylyl Carbonate (and) Steralkonium Hectorite (and) Propylene Carbonate | 2.00 |
| IV | Eumulgin ® Prisma | Disodium Cetearyl Sulfosuccinate | 0.50 |
| | Eumulgin ® VL 75 | Lauryl Glucoside (and) Polyglyceryl-2-Dipolyhydroxystearate (and) Glycerin | 3.00 |
| V | Cetiol ® Sun | Titanium Dioxide Dispersion | 10.00 |
| VI | Deionized Water | Aqua | qs 100 |
| | 2 NaEDTA | Disodium EDTA | 0.10 |
| | Preservative | | q.s. |
| | Liponic EG-1 | Glycereth-26 | 3.00 |
| | Keltrol ® T | Xanthan gum | 0.60 |
| | Veegum Ultra | Magnesium Aluminum Silicate | 2.00 |
| VII | Dry Flo Plus | Aluminum Starch Octenylsuccinate | 2.00 |
| VIII | Tinosorb ® M | Methylene Bis-Benzotriazolyl Tetramethylbutylphenol | 5.00 |
| IX | Perfume | | q.s. |

Viscosity: Brookfield Helipath 20° C., TB, 10 rpm 16200 mPas pH = 6.7

Anti-aging sunscreen

| | Ingredient | INCI | % by wt. |
|---|---|---|---|
| I | Myritol ® 331 | Cocoglycerides | 2.00 |
| | Cetiol ® B | Bibutyl Adipate | 3.00 |
| | Cetiol ® Sensoft | Propylheptyl Caprylate | 2.00 |
| | Uvinul A plus | Diethylamino Hydroxybenzoyl Hexyl Benzoate | 5.00 |
| | Uvinul T 150 | Ethylhexyl Triazone | 2.50 |
| | Cosmedia ® Gel CC | Dicaprylyl Carbonate (and) Stearalkonium Hectorite | 2.00 |
| | Cosmedia ® DC | Hydrogenated Dimer Dilinoleyl/Dimethylcarbonate Copolymer | 2.00 |
| II | Cetiol ® Sun | Titanium Dioxide Dispersion | 10.00 |
| | Satiaxane CX 91 | Xanthan gum | 0.40 |
| | Eumulgin ® Prisma | Disodium Cetearyl Sulfosuccinate | 0.0 |
| III | Deionized Water | Aqua | 49.60 |
| | 2NaEDTA | Disodium EDTA | 0.10 |
| | Glycerin | Glycerin | 3.00 |
| | Preservative | | q.s. |
| IV | Photonyl ® LS | Arginine (and) Disodium Adenosine Triphosphate (and) Mannitol (and) Pyridoxine HCl (and) RNA (and) Histidine HCl (and) Phenylalanine (and) Tyrosine | 2.00 |
| | Water | | 12.00 |
| V | Copherol ® 1250 C | Tocopheryl Acetate | 0.50 |
| | Perfume | | q.s. |

Viscosity: Brook. RVT, 20° C., spindle 5, 10 rpm 3560 mPas pH = 6.50

Anti-wrinkle cream

| | Ingredient | INCI | % by wt. |
|---|---|---|---|
| I | Eumulgin ® BA 25 | Beheneth-25 | 3.30 |
| | Lameform ® TGI | Polyglyceryl-3 Diisostearate | 0.70 |
| | Eumulgin ® Prisma | Disodium Cetearyl Sulfosuccinate | 0.1 |
| | Cetiol ® Sensoft | Propylheptyl Caprylate | 2.00 |
| | Cutina ® PES | Pentaerythrityl Distearate | 2.00 |
| | Cetiol ® CC | Dicaprylyl Carbonate | 1.30 |
| | Cetiol ® AB | C12-C15 Alkyl Benzoate | 5.00 |
| | Cetiol ® LC | Coco-Caprylate/Caprate | 3.00 |

-continued

Anti-wrinkle cream

| | Ingredient | INCI | % by wt. |
|---|---|---|---|
| | Cetiol ® Sun | Titanium Dioxide Dispersion | 6.00 |
| | Phenonip | Phenoxyethanol (and) parabens | 0.80 |
| II | Deionized Water | Aqua | 61.85 |
| | 4NaEDTA | Tetrasodium EDTA | 0.05 |
| | Glycerin | Glycerin | 3.00 |
| | Butylene Glycol | Butylene Glycol | 2.00 |

Anti-wrinkle cream

| | Ingredient | INCI | % by wt. |
|---|---|---|---|
| III | Veegum Ultra | Magnesium Aluminum Silicate | 3.00 |
| | Keltrol T | Xanthan Gum | 0.30 |
| IV | | Perfume Waterfresh | 0.50 |
| | Coviox ® T70 C | Tocopherol | 0.10 |
| V | Deionized Water | Aqua | 1.00 |
| | Plantactiv ® Aesculus | Escin | 0.10 |

Viscosity: Brookfield, RVT, 20° C., spindle 5, 5 rpm 11500 mPas pH = 6.2-6.7

Sunscreen lotion

| | Ingredient | INCI | % by wt. |
|---|---|---|---|
| I | Myritol ® 331 | Cocoglycerides | 2.00 |
| | Cetiol ® CC | Dicaprylyl Carbonate | 1.00 |
| | Cetiol ® Sensoft | Prophylheptyl Caprylate | 3.00 |
| | Cetiol ® B | Bibutyl Adipate | 2.00 |
| | Neo Heliopan ® MBC | 4-Methylbenzilidene Camphor | 3.50 |
| | Neo Heliopan ® AV | Ethylhexyl Methoxycinnamate | 6.00 |
| | Neo Heliopan ® E1000 | Isoamyl p-Methoxycinnamate | 6.00 |
| | Neo Heliopan ® 357 | Butyl Methoxydibenzoylmethane | 1.00 |
| | Cosmedia ® DC | Hydrogenated Dimer Dilinoleyl/Dimethylcarbonate Copolymer | 1.00 |
| II | Cetiol ® Sun | Titanium Dioxide Dispersion | 14.00 |
| | Satiaxane CX 91 | Xanthan gum | 0.10 |
| | Cosmedia ® SP | Sodium Polyacrylate | 0.40 |
| | Eumulgin ® Prisma | Disodium Cetearyl Sulfosuccinate | 0.75 |
| III | Deionized Water | Aqua | qs 100.00 |
| | Neo Heliopan ® Hydro | Phenylbenzimidazole Sulfonic acid | 2.00 |
| | Trometamine | Trometamine | 1.60 |
| | Phenonip | | qs |

Viscosity: Brookfield, RVT, 20° C., spindle 5, 10 rpm 2240 mPas pH = 7.35

Sun cream

| | Ingredient | INCI | % by wt. |
|---|---|---|---|
| I | Myritol ® 331 | Cocoglycerides | 2.00 |
| | Cetiol ® CC | Dicaprylyl Carbonate | 1.00 |
| | Cetiol ® Sensoft | Propylheptyl Caprylate | 1.00 |
| | Cetiol ® B | Bibutyl Adipate | 2.00 |
| | Neo Heliopan ® MBC | 4-Methylbenzilidene Camphor | 3.50 |
| | Neo Heliopan ® AV | Ethylhexyl Methoxycinnamate | 6.00 |
| | Neo Heliopan ® E1000 | Isoamyl p-Methoxycinnamate | 6.00 |
| | Neo Heliopan ® 357 | Butyl Methoxydibenzoylmethane | 1.00 |
| | Cosmedia ® DC | Hydrogenated Dimer Dilinoleyl/Dimethylcarbonate Copolymer | 2.00 |
| | Emulgade ® PL 6850 | Cetearyl Glucoside (and) Cetearyl Alcohol | 4.50 |
| | Eumulgin ® Prisma | Disodium Cetearyl Sulfosuccinate | 1.0 |
| II | Cetiol ® Sun | Titanium Dioxide Dispersion | 14.00 |
| III | Deionized Water | Aqua | qs 100.00 |
| | Neo Heliopan ® Hydro | Phenylbenzimidazole Sulfonic acid | 2.00 |
| | NaOH 50% | Sodium Hydroxide | 0.6 |
| | | Preservative | q.s. |
| | | Perfume | q.s. |

Viscosity: Brookfield, Helipath 20° C., TE, 4 rpm, 195000 mPas pH = 7.5

Sunscreen spray (% by wt.)

| | Ingredient | INCI | A | B |
|---|---|---|---|---|
| I | Eumulgin ® VL 75 | Lauryl Glucoside (and) Polyglyceryl-2 Dipolyhydroxystearate (and) Glycerin | 6.0 | 6.0 |
| | Generol ® R | Brassica Campestris (Rapeseed) | 1.0 | 1.0 |
| | Cegesoft ® SH | Sterols Shorea Stenoptera | 1.0 | 1.0 |
| | Cosmedia ® Gel CC | Dicaprylyl Carbonate (and) Stearalkonium Hectorite (and) Propylene Carbonate | 2.0 | |
| | Eumulgin ® Prisma | Disodium Cetearyl Sulfosuccinate | 0.5 | 0.5 |
| | Eusolex 2292 | Ethylhexylmethoxycinnamate | 7.5 | 7.5 |
| | Tinosorb ® S | Bis-ethylhexyloxyphenol | 2.0 | 2.0 |

| | Sunscreen spray (% by wt.) | | | |
|---|---|---|---|---|
| | Ingredient | INCI | A | B |
| | | methoxyphenyltriazine | | |
| | Cetiol ® CC | Dicaprylyl carbonate | 1.5 | |
| | Cetiol ® Sensoft | Propylheptyl Caprylate | 1.5 | 1.5 |
| | Cetiol ® AB | C12-15 Alkyl Benzoate | 4.0 | 4.0 |
| | Cosmedia ® DC | Hydrogenated Dimer Dilinoleyl/ Dimethylcarbonate Copolymer | 1.00 | 1.00 |
| II | Water | | 61.45 | 63.45 |
| | EDTA 4Na (Prolabo) | Tetrasodium EDTA | 0.05 | 0.05 |
| | Elestab 50J | Chlorphenesin & Methylparaben | 0.60 | |
| III | Cosmedia ® SP | Sodium Polyacrylate | 0.40 | 0.40 |
| IV | Tinsorb ® M | Methylenebis benzotriazolyl tetramethylbutylphenol | 10.0 | 10.0 |

Viscosity: Brookfield. RVT, 23° C., spindle 2.5 rpm, pH: 6 3500 mPas 700 mPas

| | Spray | | | |
|---|---|---|---|---|
| | Ingredient | INCI | A | B |
| I | Eumulgin ® Prisma | Disodium Cetearyl Sulfosuccinate | 0.6 | 0.6 |
| | Generol ® | *Brassica Campestris* (Rapeseed) Sterols | 1.0 | 1.0 |
| | Cegesoft ® SH | *Shorea Stenoptera* | 1.0 | 1.0 |
| | Cosmedia ® Gel CC | Dicaprylyl Carbonate (and) Stearalkonium Hectorite (and) Propylene Carbonate | 3.0 | — |
| | Cetiol ® Sensoft | Propylheptyl Caprylate | 2.0 | 2.0 |
| | Eusolex 2292 | Ethylhexylmethoxycinnamate | 7.5 | 7.5 |
| | Tinosorb S | Bis-ethylhexyloxyphenol methoxyphenyltriazine | 2.13 | 4.74 |
| | Cetiol ® CC | Dicaprylyl Carbonate | 2.0 | 2.0 |
| | Cetiol ® AB | C12-15 Alkyl Benzoate | 4.0 | 4.0 |
| II | Water | | 62.32 | 62.71 |
| | EDTA 4Na | Tetrasodium EDTA | 0.05 | 0.05 |
| | Elestab 50J | Chlorphenesin & Methylparaben | 0.60 | 0.60 |
| III | Cosmedia ® SP | Sodium Polyacrylate | 0.40 | 0.40 |
| IV | Tinosorb M | Methylenebis benzotriazolyl tetramethylbutylphenol | 10.00 | 10.00 |

Viscosity: Brook. RVT, 23° C., spindle 2.5 rpm, pH: 6
A: 4020 mPas B: 730 mPas

| | Spray (figures in % by wt.) | | | |
|---|---|---|---|---|
| | Ingredient | INCI | A | B |
| I | Eumulgin ® VL 75 | Lauryl Glucoside (and) Polyglyceryl-2 Dipolyhydroxystearate (and) Glycerin | 6.0 | 6.0 |
| | Eumulgin ® Prisma | Disodium Cetearyl Sulfosuccinate | 0.2 | 0.2 |
| | Generol ® R | *Brassica Campestris* (Rapeseed) Sterols | 1.0 | 1.0 |
| | Cegesoft ® SH | *Shorea Stenoptera* | 1.0 | 1.0 |
| | Cosmedia ® Gel CC | Dicaprylyl Carbonate (and) Stearalkonium Hectorite (and) Propylene Carbonate | 2.0 | |
| | Eusolex 2292 | Ethylhexylmethoxycinnamate | 7.5 | 7.5 |
| | Tinosorb S | Bis-ethylhexyloxyphenol methoxyphenyltriazine | 2.0 | 2.0 |
| | Cetiol ® CC | Dicaprylyl carbonate | 1.5 | 1.5 |
| | Cetiol ® Sensoft | Propylheptyl Caprylate | 1.5 | 1.5 |
| | Cetiol ® AB | C12-15 Alkyl Benzoate | 4.0 | 4.0 |
| | Cosmedia ® DC | Hydrogenated Dimer Dilinoleyl/Dimethylcarbonate Copolymer | 1.0 | 1.00 |
| II | Water | | 61.45 | 63.45 |
| | EDTA 4Na | Tetrasodium EDTA | 0.05 | 0.05 |
| | Elestab 50J | Chlorphenesin & Methylparaben | 0.60 | 0.60 |
| III | Cosmedia ® SP | Sodium Polyacrylate | 0.40 | 0.40 |
| IV | Tinosorb M | Methylenebis benzotriazolyl tetramethylbutylphenol | 10.0 | 10.0 |

Viscosity: Brook. RVT, 23° C., spindle 2.5 rpm, pH: 6
[mPas] A: 3500, B: 700

Matt finish fluid foundation

| | Ingredient | INCI | % by wt. |
|---|---|---|---|
| I | Lameform ® TGI | Polyglyceryl-3 Diisostearate | 1.50 |
| | Eumulgin ® BA25 | Beheneth-25 | 3.50 |
| | Eumulgin ® Prisma | Disodium Cetearyl Sulfosuccinate | 0.05 |
| | Cetiol ® CC | Dicaprylyl Carbonate | 4.00 |
| | Myritol ® 331 | Cocoglycerides | 2.00 |
| | Cetiol ® Sensoft | Propylheptyl Caprylate | 2.00 |
| | Fitoderm ® | Squalane | 3.00 |
| | Cutina ® PES | Pentaerythrityl Distearate | 1.00 |
| | Cegesoft ® SH | *Shorea Stenoptera* | 1.00 |
| | Phenonip | Phenoxyethanol (and) Parabens | 0.80 |
| | KF 96, 100cs | Dimethicone | 3.00 |
| | Cetiol ® OE | Dicaprylyl Ether | 3.00 |
| II | Sun Croma C47-051 | Titanium Dioxide | 6.00 |
| | SunPuro Yellow Iron Oxide C33-9001 | Iron Oxide CI 77492 | 1.30 |
| | SunPuro Red Iron Oxide C33-8001 | Iron Oxide CI 77491 | 0.60 |
| | SunPuro Black Iron Oxide C33-7001 | Iron Oxide CI 77499 | 0.20 |
| III | Deionized water | Aqua | 52.50 |
| | Glycerine | Glycerin | 3.00 |
| | Butylene Glycol | Butylene Glycol | 2.00 |
| IV | Veegum Ultra | Magnesium Aluminium Silicate | 1.00 |
| | Keltrol T | Xanthan Gum | 0.40 |
| V | Cosmedia ® Gel CC | Dicaprylyl Carbonate (and) Stearalkonium Hectorite (and) Propylene Carbonate | 3.00 |
| VI | Cosmedia ® PMMA V12 | Polymethylmethacrylate | 2.00 |
| VII | Mirasil CDPDM | Cyclomethicone (and) Diphenyldimethicone | 3.00 |
| VIII | Perfume Caresse | | 0.20 |

Viscosity: Brook. RVT, spindle 3, speed 5, 8400 mPas pH: 6.7

Ultraprotective spray

| | Ingredient | INCI | % by wt. |
|---|---|---|---|
| I | Eumulgin ® VL 75 | Lauryl Glucoside (and) Polyglyceryl-2 Dipolyhydroxystearate (and) Glycerin | 7.00 |
| | Eumulgin ® Prisma | Disodium Cetearyl Sulfosuccinate | 0.5 |
| | Generol ® R | *Brassica Campestris* (Rapeseed) Sterols | 1.00 |
| | Cosmedia ® DC | Hydrogenated Dimer Dilinoleyl/ Dimethylcarbonate Copolymer | 1.00 |
| | Eusolex 2292 | Ethylhexylmethoxycinnamate | 7.50 |
| | Tinosorb S | Bis-ethylhexyloxyphenol methoxyphenyltriazine | 2.00 |
| | Cetiol ® CC | Dicaprylyl carbonate | 2.00 |
| | Cetiol ® AB | C12-15 Alkyl Benzoate | 4.00 |
| | Cetiol ® Sensoft | Propylheptyl Caprylate | 2.00 |
| | Cegesoft ® VP | Olus & Hydrogenated Vegetable Oil & Candelilla Cera | 2.50 |
| | Myritol ® 331 | Cocoglycerides | 2.00 |
| | Cosmedia ® Gel CC | Sodium polyacrylate Carbonate (and) Stearalkonium Hectorite (and) Propylene Carbonate | 4.00 |
| II | Water | qsp 100 | 55.15 |
| | EDTA 4Na | Tetrasodium EDTA 0.05 | 0.05 |
| | Elestab 50J | Chlorphenesin & Methylparaben | 0.60 |
| III | Keltrol T | Xanthan Gum | 0.20 |
| IV | Tinosorb M | Methylenebis benzotriazolyl tetramethylbutylphenol | 10.00 |

Viscosity: Brook. RVT, 23° C., spindle 2.5 rpm, 2500 mPas pH: 6.4

Soft moisture gel cream

| | Ingredient | INCI | % by wt. |
|---|---|---|---|
| I | Deionized Water | Aqua | 65.35 |
| | Eumulgin ® Prisma | Disodium Cetearyl Sulfosuccinate | 0.2 |
| | Glycerine | Glycerin | 3.00 |
| | Phenonip | Phenoxyethanol (and) Parabens | 0.60 |
| II | Cosmedia ® SP | Sodium Polyacrylate | 1.20 |

Soft moisture gel cream

| | Ingredient | INCI | % by wt. |
|---|---|---|---|
| III | Cegesoft ® PFO | *Passiflora Incarnata* | 2.00 |
| | Eusolex ® 2292 | Ethylhexyl Methoxycinnamate | 2.00 |
| | KF 96, 100cs | Dimethicone 2.00 | 2.00 |
| IV | Cetiol ® CC | Dicaprylyl Carbonate | 2.50 |
| | Eutanol ® G | Octyldodecanol | 4.0 |
| | Cetiol ® Sensoft | Propylheptyl Caprylate | 2.50 |
| | Eusolex ® 4360 | Benzophenone-3 | 0.10 |
| | Cegesoft ® SBE | *Butyrospermum Parkii* | 1.50 |
| V | Cosmedia ® Gel CC | Dicaprylyl Carbonate (and) Stearalkonium Hectorite (and) Propylene Carbonate | 5.00 |
| VI | Deionized Water | Aqua | 5.00 |
| | Osmhydran ® LS 8453 | Mannitol (and) Arginine (and) Serine (and) Sucrose (and) PCA (and) Citrulline (and) Glycogen (and) Histidine HCl (and) Alanine (and) Threonine (and) Glutamic Acid (and) Lysine HCl | 2.00 |
| VII | Vegeseryl ® LP LS 9058 | Hydrolyzed Soy Protein | 1.00 |
| VIII | Coviox ® T70C | Tocopherol | 0.10 |
| | Perfume Raphaelle | | 0.15 |

Viscosity: Brook. RVT, Helipath TE, speed 4, 101 000 mPas pH: 5.5

Silky cleansing mask

| | Ingredient | INCI | % by wt. |
|---|---|---|---|
| I | Emulgade ® SE-PF | Glyceryl Stearate (and) Ceteareth-20 (and) Ceteareth-12 (and) Cetearyl Alcohol (and) Cetyl Palmitate | 8.00 |
| | Eumulgin ® Prisma | Disodium Cetearyl Sulfosuccinate | 1 |
| | Lanette ® O | Cetearyl Alcohol | 2.00 |
| | Cegesoft ® PS6 | Olus | 5.00 |
| | Cetiol ® CC | Dicaprylyl Carbonate | 2.00 |
| | Cutina ® PES | Pentaerythrityl Distearate | 3.00 |
| | Cetiol ® Sensoft | Propylheptyl Caprylate | 2.00 |
| II | Cosmedia ® Gel CC | Dicaprylyl Carbonate (and) Stearalkonium Hectorite (and) Propylene Carbonate | 5.00 |
| III | Deionized Water | Aqua | 45.00 |
| | Glycerine | Glycerin | 10.00 |
| | EDTA, 4Na | Tetrasodium EDTA | 0.10 |
| | Elestab ® 50J | Chlorphenesin (and) Methylparaben | 0.40 |
| IV | Dry Flo AF | Corn Starch Modified 0 | 1.00 |
| | Propylene Glycol | Propylene Glycol | 3.00 |
| V | Kaolin | Kaolin | 10.00 |
| VI | Perfume Concombre | | 0.20 |
| | Coviox ® T70C | Tocopherol | 0.10 |
| VII | Purisoft ® LS 9602 | Glycerin (and) *Moringa Pterygosperma* | 2.00 |
| VIII | Green Covasol W7035 (a.s. 0.1%) | CI 42090 (and) CI 19140 | 3.20 |

Viscosity: Brook. RVT, Helipath TE, speed 4, 254 000 mPas pH: 6.3

Luxurious body butter

| | Ingredient | INCI | % by wt. |
|---|---|---|---|
| I | Deionized water | Aqua | 61.50 |
| | Glycerine | Glycerin | 5.00 |
| | Butylene Glycol | Butylene Glycol | 2.00 |
| | EDTA, 4 Na | Tetrasodium EDTA | 0.10 |
| | Phenonip | Phenoxyethanol (and) Parabens | 0.80 |
| II | Cosmedia ® SP | Sodium Polyacrylate | 1.50 |
| III | Eumulgin ® BA 25 | Beheneth-25 | 3.00 |
| | Lanette ® O | Cetearyl Alcohol | 4.00 |
| | Eumulgin ® Prisma | Disodium Cetearyl Sulfosuccinate | 0.6 |
| | Cetiol ® SN | Cetearyl Isononanoate | 3.00 |
| | Cetiol ® SB45 | *Butyrospermum Parkii* | 5.00 |
| | Cetiol ® CC | Dicaprylyl Carbonate | 0.50 |

Luxurious body butter

| | Ingredient | INCI | % by wt. |
|---|---|---|---|
| | Cetiol ® Sensoft | Propylheptyl Caprylate | 0.50 |
| | KF 96, 100cs | Dimethicone | 1.00 |
| | Generol ® R | *Brassica Campestris* (Rapeseed) Sterols | 0.50 |
| IV | Cosmedia ® Gel CC | Dicaprylyl Carbonate (and) Stearalkonium Hectorite (and) Propylene Carbonate | 5.00 |
| V | Cosmedia ® PMMAV12 | Polymethylmethacrylate | 2.00 |
| | Deionized water | Aqua | 4.00 |
| VI | Coviox ® T70C | Tocopherol | 0.10 |
| | Perfume Pètale 139012E | | 0.50 |

Viscosity: Brook. RVT, Helipath TE, speed 4, 800 000 mPas pH: 7

Makeup foundation

| Component INCI name (trade name, manufacturer) | % by wt. |
|---|---|
| Water | 78.2 |
| Glycerin | 1.89 |
| Triethanolamine 99% | 0.75 |
| Methylparaben (Nipagin M. Nipa) | 0.19 |
| Xanthan gum (Keltrol SP, CP Kelco) | 0.28 |
| Titanium dioxide (Softex Titanium dioxide, C47-7756, Sun Chemical) | 8.75 |
| Brown iron oxide (SunChroma Brown iron oxide, C33-315 Sun Chroma, Sun Chemical) | 1.08 |
| Red iron oxide (SunChroma red iron oxide, C33-124 Sun Chroma, Sun Chemical) | 0.17 |
| Phenyl trimethicone (DC 556 Cosmetic Fluid, Dow Corning) | 3.41 |
| Cetiol ® Sensoft (Propylheptyl Caprylate) | 1 |
| Stearic acid, 94% | 1.33 |
| Eumulgin ® Prisma (Disodium Cetearyl Sulfosuccinate) | 0.5 |
| Cetyl stearyl alcohol (Lanette O, Cognis) | 2.84 |
| Propylparaben (Nipasol, M. Nipa) | 0.1 |

O/W liquid foundation

| | Ingredient | INCI name | % by wt. |
|---|---|---|---|
| I | Deionized water | Aqua | 50.50 |
| | Butylene Glycol | Butylene Glycol | 2.00 |
| | Glycerine | Glycerin | 3.00 |
| II | Veegum Ultra | Magnesium Aluminium Silicate | 1.00 |
| | Keltrol T | Xanthan Gum | 0.40 |
| III | Lameform ® TGI | Polyglyceryl-3 Diisostearate | 1.50 |
| | Eumulgin ® B2 | Ceteareth-20 | 3.50 |
| | Eumulgin ® Prisma | Disodium Cetearyl Sulfosuccinate | 0.5 |
| | Cutina ® PES | Pentaerythrityl Distearate | 1.00 |
| | Cegesoft ® SH | *Shorea Stenoptera* | 1.00 |
| | Cetiol ® CC | Dicaprylyl Carbonate | 4.00 |
| | Cetiol ® Sensoft | Propylheptyl Caprylate | 2.00 |
| | Myritol ® 331 | Cocoglycerides | 4.00 |
| | Fitoderm ® | Squalane | 3.00 |
| | Cetiol ® Sensoft | Propylheptyl Caprylate | 5.00 |
| | Phenonip | Phenoxyethanol (and) Parabens | 0.80 |
| IV | Sun Croma C47-051 | Titanium Dioxide | 6.00 |
| | SunPuro Yellow Iron Oxide C33-9001 | Iron Oxide CI 77492 | 1.30 |
| | SunPuro Red Iron Oxide C33-8001 | Iron Oxide CI 77491 | 0.60 |
| | SunPuro Black Iron Oxide C33-7001 | Iron Oxide CI 77499 | 0.20 |
| V | Cosmedia ® Gel CC | Dicaprylyl Carbonate (and) Stearalkonium Hectorite (and) Propylene Carbonate | 3.00 |
| VI | Micropearl M100 | Polymethylmethacrylate | 2.00 |
| VII | Mirasil CDPDM | Cyclomethicone (and) Diphenyldimethicone | 3.00 |
| VIII | Perfume Caresse | | 0.20 |

Viscosity (mPa · s): Brk. RVT spindle 5, speed 10 5 500, pH 7.3

TABLE 1

Examples of tinted day cream of the O/W type

| Ingredient | 1 | 2 | 3 | 4 | 5 | 6 | 7 | 8 |
|---|---|---|---|---|---|---|---|---|
| Eumulgin ® PRISMA | 0.5 | 1.0 | 2.0 | 0.5 | 0.5 | 2.0 | 2.0 | 1.0 |
| Cutina ® GMS-SE | 5.5 | | | | | | | 3.0 |
| Emulgade ® PL 68/50 | | 5.0 | | | 2.0 | | | |
| Eumulgin ® VL 75 | | | 3.0 | | | 5.0 | | |
| Tego Care ® 450 | | | | | | | 2.0 | 2.0 |
| Crodesta ® F-50 | | | | 6.0 | | | | |
| Amphisol ® K | | | | 2.0 | | | | |
| Lanette ® E | | 0.25 | | | 1.0 | 1.0 | | |
| Cutina ® FS 45 | 1.5 | | | | | | | |
| Eumulgin ® B 2 | | | 2.0 | | | | | 2.0 |
| Cutina ® PES | 2.0 | 1.0 | 2.0 | 4.0 | 2.0 | 2.0 | 2.5 | 2.0 |
| Lanette ® O | | | 2.0 | | | | | 1.0 |
| Cutina ® MD | | | 0.5 | 3.0 | 3.0 | | | |
| Cetiol ® LC | 4.0 | 5.0 | | | | | | |
| Cosmedia ® DC | 0.5 | | 1.0 | | | | | 1.0 |
| Cetiol ® CC | 4.0 | | 4.0 | | 7.0 | 5.0 | 10.0 | |
| Tegosoft ® DEC | | 5.0 | 2.0 | 4.0 | 2.0 | 2.0 | | 6.0 |
| Dow Corning ® 245 | | 2.0 | | 2.0 | | | | 2.0 |
| Eutanol ® G 16 | 4.0 | | | | 3.0 | 3.0 | | |
| Myritol ® 331 | | 5.0 | | | 2.0 | 2.0 | 5.0 | |
| Uvinul ® T 150 | | | | 0.5 | | | | 0.5 |
| Uvasorb ® HEB | 2.0 | | | | | | 1.0 | 1.0 |
| Tinosorb ® M | | | 2.0 | | | | | 2.0 |
| Tinosorb ® S | | | | 3.0 | | | | 2.0 |
| Neo Heliopan ® AV | | | | | 2.0 | | 2.0 | |
| Heo Heliopan ® AP | | | | | 1.0 | | 1.0 | |
| Uvinul ® A plus | | | | 1 | | | 2.0 | 2.0 |
| Microna ® Matte White | 5.0 | 5.0 | | 5.0 | 5.0 | 5.0 | | 5.0 |
| Microna ® Matte Black | 0.3 | 0.3 | 0.1 | 0.3 | 0.3 | 0.3 | 0.4 | 0.3 |
| Microna ® Matte Yellow | 3.0 | 3.0 | | 3.0 | 3.0 | 3.0 | 2.0 | 3.0 |
| Microna ® Matte Red | 0.6 | 0.6 | 1.0 | 0.6 | 0.6 | 0.6 | 1.0 | 0.6 |
| Ronasphere ® LDP | 1.0 | 1.0 | | 1.0 | 1.0 | 1.0 | | 1.0 |
| Pigment White 6 | | | 6.0 | | | | 6.0 | |
| Dry Flow PC | | | | | | | 2.0 | 2.0 |
| Glycerin | 5.0 | 5.0 | 3.0 | 5.0 | 5.0 | 5.0 | 3.0 | |
| Cosmedia ® SP | | | 0.3 | | 0.2 | | | |

Water, deionized: ad 100, Preservative

TABLE 2

Examples of tinted day cream of the W/O type

| Ingredient | 1 | 2 | 3 | 4 | 5 | 6 | 7 | 8 |
|---|---|---|---|---|---|---|---|---|
| Eumulgin ® SG | 0.1 | 0.2 | 0.15 | 0.3 | 0.1 | 0.05 | 0.1 | 0.01 |
| Dehymuls ® PGPH | 5.5 | | 4.0 | | | | | 3.0 |
| Lameform ® TGI | | 5.0 | | | | 2.0 | | |
| Abil ® EM 90 | | | | 3.0 | | | 5.0 | |
| Isolan ® GI 34 | | | | | | 2.0 | 2.0 | |
| Isolan ® PDI | | | | | 6.0 | | | |
| Admul ® WOL 1403 | | | | 2.0 | | | | |
| Dehymuls ® HRE 7 | | 1.0 | | | 1.0 | 1.0 | | |
| Monomuls ® 90-O18 | 1.5 | | | | | | | 2.0 |
| Cutina ® PES | 2.0 | 1.0 | | 4.0 | | 1.0 | 2.5 | 2.0 |
| Cera Bellina | | | 2.0 | | | | | 2.0 |
| Beeswax | | | 2.0 | | | 2.0 | | 1.0 |
| Microcrystalline Wax | | 1.5 | 3.0 | 3.0 | | | | |
| Cetiol ® LC | 4.0 | 5.0 | | | | | | |
| Cosmedia ® DC | 1.0 | | | | 0.5 | | 1.0 | |
| Cetiol ® CC | 4.0 | | | | 7.0 | 5.0 | | 10.0 |
| Tegosoft ® DEC | | 5.0 | 2.0 | 4.0 | 2.0 | 2.0 | | 6.0 |
| Dow Corning ® 245 | | 2.0 | | 2.0 | | | | 2.0 |
| Eutanol ® G 16 | 4.0 | | | | 3.0 | 3.0 | | |
| Myritol ® 331 | | 5.0 | | | 2.0 | 2.0 | 5.0 | |
| Uvinul ® T 150 | | | | 0.5 | | | | 0.5 |
| Uvasorb ® HEB | | | 2.0 | | | | 1.0 | 1.0 |
| Tinosorb ® M | | | 2.0 | | | | | 2.0 |
| Tinosorb S | | | | 3.0 | | | | 2.0 |
| Neo Heliopan ® AV | | | | 2.0 | | 2.0 | | |
| Heo Heliopan ® AP | | | | 1.0 | | 1.0 | | |
| Uvinul ® A plus | | | 1.0 | | | | 2.0 | 2.0 |
| Microna ® Matte White | 5.0 | 5.0 | | 5.0 | 5.0 | 5.0 | | 5.0 |
| Microna ® Matte Black | 0.3 | 0.3 | 0.1 | 0.3 | 0.3 | 0.3 | 0.4 | 0.3 |
| Microna ® Matte Yellow | 3.0 | 3.0 | 3.5 | 3.0 | 3.0 | 3.0 | 2.0 | 3.0 |
| Microna ® Matte Red | 0.6 | 0.6 | 1.0 | 0.6 | 0.6 | 0.6 | 1.0 | 0.6 |
| Ronasphere ® LDP | 1.0 | 1.0 | | | 1.0 | 1.0 | | 1.0 |
| Pigment White 6 | | | 6.0 | | | | 6.0 | |
| Dry Flow PC | | | | | | | 2.0 | 2.0 |
| Glycerin | 5.0 | 5.0 | 3.0 | | 5.0 | 5.0 | 5.0 | 3.0 |

Water, deionized: ad 100, Preservative

TABLE 3

Examples of lipsticks

| Ingredient | 1 | 2 | 3 | 4 |
|---|---|---|---|---|
| Eumulgin ® SG | 2.0 | 1.0 | 0.5 | 2.0 |
| Cutina ® LM conc | | | 10.0 | 36.0 |
| Candelilla Wax | 9.39 | 5.0 | 10.0 | |
| Carnauba wax | 2.85 | 7.0 | 5.0 | |
| Beeswax | 1.86 | 5.0 | 4.0 | |
| Cutina ® PES | 3.2 | 5.0 | 6.4 | 4.5 |
| Cetiol ® MM | | | 5.0 | |
| Cosmedia ® DC | 5.0 | 4.0 | 2.0 | 6.0 |
| Cetiol ® CC | 7.0 | 6.0 | 3.0 | 5.0 |
| Tegosoft ® DEC | 3.0 | 3.0 | 3.0 | 5.0 |
| Eutanol ® G | 10.97 | 12.0 | 12.0 | |
| Fitoderm ® | | | | 4.0 |
| Monomuls ® 90L 12 | | 3.0 | | |
| Dehymuls ® PGPH | | 4.0 | | |
| Castor Oil | 11.0 | 15.5 | 14.5 | 30.0 |
| Copherol ® F 1300 | 1.0 | 1.0 | 1.0 | 1.0 |
| Cosmetic white C47056 | 5.0 | 2.0 | 5.0 | |
| FDC Yellow 6 Al Lake C705270 | 7.0 | 7.0 | 8.0 | |
| Pigment White 6 | | | | |
| DC Red 7 Ca Lake C 19003 | 6.0 | 4.5 | 1.1 | 2.9 |
| Irodin 100 Silverpearl | | | | 9.6 |
| Hydagen ® CMF | | 10.0 | | |
| Irwinol ® LS 9319 | 1.0 | | 3.0 | |
| Mineral Oil | 12.8 | | | |
| Petrolatum | 6.84 | 3.0 | | |
| Ceresin | 2.75 | | | |
| Microcrystalline Wax | 2.45 | | | |
| Colophane Claire type Y | 1.89 | | | |

TABLE 4

O/W sunscreen emulsions

| Component | 1 | 2 | 3 | 4 | 5 | 6 | 7 | 8 | 9 | 10 | 11 |
|---|---|---|---|---|---|---|---|---|---|---|---|
| C—Cream, L—Lotion | L | C | S | L | C | L | L | C | L | C | L |
| Eumulgin ® PRISMA | 0.5 | 1.0 | 0.2 | 0.1 | 1.0 | 0.5 | 0.5 | 2.0 | 0.5 | 0.1 | 0.5 |
| Eumulgin ® VL 75 | | | | | | | | | | | 2 |
| Eumulgin ® B2 | 0.5 | | | | | | | | | | |
| Tween ® 60 | | | | | 0.2 | | | | | | |
| Myrj ® 51 | | | | | 0.5 | | | | | | |
| Cutina ® E 24 | | | | | 0.1 | | | | | | |
| Hostaphat ® KL 340 N | | | | | | | | | 0.6 | | |
| Lanette ® E | | | | 0.2 | | | | | | | |
| Amphisol ® K | | | | | | | | | | 1 | |
| Sodium stearate | | | | | | | 1 | | | | |
| Emulgade ® PL 68/50 | | | | 1 | | | | | | | |
| Tego ® Care 450 | | | | | | | | | | | 1 |
| Cutina ® PES | 2 | 2.5 | 2.5 | | 2.5 | 2.5 | 2.5 | 2 | 2.5 | 1.7 | 1.5 |
| Cutina ® MD | 2 | | | 2 | | | 2 | | | 6 | |
| Lanette ® 14 | 1 | | | 1 | | | | | 2 | | 2 |
| Lanette ® O | 1 | 6 | | | 5 | 2 | | 2 | | | |
| Cosmedia ® DC | 1 | 1.5 | | 1 | 1 | | 2 | | 2 | | 2 |
| Antaron ® V216 | | | 2 | | | 1.5 | | | 1 | 1 | |
| Emery 1780 | | | | | | 0.5 | 0.5 | | | | |
| Lanolin, anhydrous USP | | | | | | | 5 | | | | |
| Myritol ® PC | | | | | | 5 | | | | | |
| Myritol ® 331 | 5 | | 8 | | | 6 | | 10 | | 2 | |
| Finsolv ® TN | | | 1 | | | | | 1 | 8 | | |
| Cetiol ® CC | | 2 | 5 | | 4 | 4 | 2 | | 2 | | |
| Cetiol ® OE | | | 3 | | | | | 2 | | 3 | |
| Dow Corning DC ® 244 | 4 | | 1 | 5 | | | 2 | | | | 2 |
| Dow Corning DC ® 2502 | | 1 | | 2 | | | | | | | |
| Squatol ® S | | | | | | | | 4 | | | |

TABLE 4-continued

O/W sunscreen emulsions

| Component | 1 | 2 | 3 | 4 | 5 | 6 | 7 | 8 | 9 | 10 | 11 |
|---|---|---|---|---|---|---|---|---|---|---|---|
| Wacker AK ® 350 silicone oil | | 2 | | | | | | | | | |
| Cetiol ® 868 | | | | | 2 | | 4 | | | | 7 |
| Cetiol ® J 600 | | | | | 3 | 2 | | | | 5 | |
| Mineral oil | | | | 9 | | | | | | | |
| Cetiol ® B | | | 1 | | | | | | | 2 | |
| Eutanol ® G | | | | | 2 | | | | 4 | | |
| Eutanol ® G 16 | 4 | | | | | 4 | | | | | |
| Cetiol ® PGL | | 5 | | | | | | | | 5 | |
| Almond oil | | | 2 | | | | 1 | | | | |
| Photonyl ® LS | | | | | 2 | | | | | 2 | |
| Panthenol | | | | | | 1 | | | | | |
| Bisabolol | | | | | | 0.2 | | | | | |
| Tocopherol/Tocopheryl acetate | | | | | | 1 | | | | | |
| Photonyl ® LS | | | | | | | | | | | |
| Neo Heliopan ® AP (Na salt) | | 1 | | | | | | | 1 | | |
| Neo Heliopan ® Hydro (Na salt) | 2 | | 2.2 | | | | | | 1 | | |
| Neo Heliopan ® 303 | 3 | 5 | 9 | 4 | | | | | | | |
| Neo Heliopan ® BB | | | | | 1 | | | | | | 2 |
| Neo Heliopan ® MBC | 2 | | | 3 | | 2 | 2 | 2 | | | 1 |
| Neo Heliopan ® OS | | | | | | | | | | 10 | 7 |
| Neo Heliopan ® E 1000 | | 7.5 | | 6 | | | | | | | 6 |
| Neo Helopan ® AV | | | 7.5 | | | 7.5 | 4 | 5 | | | |
| Uvinul ® A PLUS | | | | 2 | 1 | | | | | | |
| Uvinul ® T 150 | 2 | | | | 2.5 | | 1 | | | | |
| Tinosorb ® M | | | 3 | | | | 2 | | | | 3 |
| Tinosorb ® S | | | 1 | | | | 1.5 | | | | |
| Uvasorb ® HEB | | 1 | 1 | | 1 | | | | | | |
| Parsol ® 1789 | | 1 | 1 | | | | | 2 | | 2 | 2 |
| Zinc oxide NDM | 10 | | 5 | | | 10 | | 3 | | 5 | 4 |
| Eusolex ® T 2000 | | | | | 5 | | 3 | 3 | | | 4 |
| Veegum ® Ultra | 1.5 | | 0.75 | | | | | 1 | 1 | | |
| Keltrol ® T | 0.5 | | 0.25 | | | | | 0.5 | 0.5 | | |
| Cosmedia ® SP | | 0.5 | | | 0.5 | | 0.2 | 0.2 | | 0.2 | 0.2 |
| Carbopol ® 980 | | | | 0.2 | | 0.2 | | | 0.1 | 0.3 | 0.2 |
| Ethanol | | | | | | | | | | 10 | |
| Butylene glycol | | 2 | | 4 | 3 | | 2 | 5 | 2 | | 2 |
| Glycerin | 5 | 5 | 5 | | 3 | 3 | 2 | | 4 | | 3 |
| Preservative, NaOH, Water | | | | | q.s. ad 100 | | | | | | |

TABLE 5

O/W sunscreen emulsions

| Component | 12 | 13 | 14 | 15 | 16 | 17 | 18 | 19 | 20 | 21 | 22 |
|---|---|---|---|---|---|---|---|---|---|---|---|
| C—Cream, L—Lotion | L | C | L | C | L | C | S | C | C | L | L |
| Eumulgin ® PRISMA | 0.4 | 1.0 | 0.3 | 1.5 | 0.6 | 1.2 | 0.3 | 0.6 | 2.0 | 0.4 | 0.4 |
| Eumulgin ® VL 75 | | | | | 1.8 | | | | | | |
| Eumulgin ® B2 | | | | | | | | | | 0.2 | |
| Tween ® 60 | | | | | | | | | | 0.3 | |
| Cutina ® E 24 | | | | 0.5 | | | | | | | |
| Lanette ® E | | | | | | | | 0.1 | | | |
| Amphisol ® K | 0.5 | | | | | | 1 | | | | |
| Sodium stearate | | | | | 1 | | | | | | |
| Emulgade ® PL 68/50 | | 1.5 | | | | | | | | | |
| Tego ® Care 450 | | | | | | | | | 0.3 | | |
| Cutina ® PES | 2 | 1.8 | 2.5 | 1.5 | 1 | 2 | 2.5 | 3 | 2.0 | 1.5 | 1.5 |
| Cutina ® MD | 1 | | | 4 | 1 | 3 | | | | | 1 |
| Lanette ® 14 | | 2 | | | | | | | | 1 | |
| Lanette ® O | | | | 2 | | | | 2 | 1 | 1 | |
| Allianz ® OPT | 1 | | | 1 | 1 | | | 2 | | | 2 |
| Cosmedia ® DC | | 1.5 | 2 | | | 1.5 | 2 | | | 1.5 | 1.5 |
| Emery ® 1780 | | | 1 | 1 | | | | | | | |
| Lanolin, anhydrous, USP | | | | | | 1 | 1 | | | | |
| Myritol ® PC | | | | | | | | | 5 | | |
| Myritol ® 331 | 12 | | 12 | | | 8 | 8 | | | 10 | 8 |
| Finsolv ® TN | | | | | 5 | | | 3 | 3 | | |
| Cetiol ® CC | 6 | | 6 | | | 5 | 5 | | | | |
| Cetiol ® OE | | | | | 2 | | | | | | 2 |
| Dow Corning DC ® 244 | | 2 | | 1 | | | | | | | |
| Dow Corning DC ® 2502 | | 1 | | 1 | | | | 3 | | | |

TABLE 5-continued

| O/W sunscreen emulsions | | | | | | | | | | | |
|---|---|---|---|---|---|---|---|---|---|---|---|
| Component | 12 | 13 | 14 | 15 | 16 | 17 | 18 | 19 | 20 | 21 | 22 |
| Ceraphyl ® 45 | | | | | | | | | | 2 | 2 |
| Wacker AK ® 350 silicone oil | | | | | 1 | | | | | | |
| Cetiol ® 868 | | 2 | | | | | | | | | |
| Cetiol ® J 600 | | 2 | | | | | | | | | |
| Mineral oil | | | | 10 | | | | | | | |
| Cetiol ® B | 4 | | 4 | | | | | 4 | | | |
| Eutanol ® G | | 3 | | | | 3 | | | | | |
| Eutanol ® G 16 S | 10 | | | | | | | | | | |
| Cetiol ® PGL | | | | | | | | | 2 | | |
| Photonyl ® LS | | | | | | | | | | 2 | |
| Panthenol | | | | | | 1 | | | | | |
| Bisabolol | | | | | | 0.2 | | | | | |
| Tocopherol/Tocopheryl acetate | | | | | | 1 | | | | | |
| Neo Heliopan ® Hydro (Na salt) | | | | | | | | | | 3 | |
| Eusolex ® OCR | 6 | | 9 | | 5 | 7 | 9 | | 4 | | 7 |
| Neo Heliopan ® AP (Na salt) | | | | 0.5 | | 1 | | | | | |
| Neo Heliopan ® BB | | | | | | | | 1 | 1 | | 1 |
| Neo Heliopan ® MBC | | 2 | | 1 | | | | 3 | 1 | | 3 |
| Neo Heliopan ® OS | 2 | | | | | | | | 7 | | |
| Neo Heliopan ® E 1000 | | 4 | | | | | | 5 | | | |
| Neo Helopan ® AV | | 4 | 7.5 | 5 | | | | 5 | 4 | 7.5 | |
| Uvinul ® A PLUS | | | | | 1 | | 2 | | | | |
| Uvinul ® T 150 | 1 | | | | | | | | 1.3 | 1 | 1 |
| Tinosorb ® M | | | 6.5 | | | | | | | 4 | |
| Tinosorb ® S | | | 1 | | 2 | | | | | | |
| Uvasorb ® HEB | 1 | | | | | | | | | | 2 |
| Parsol ® 1789 | 1 | | | | | | | | 2 | | 1 |
| Z-Cote ® HP 1 | 7 | 2 | 5 | | | 7 | 5 | | 6 | 2 | |
| Eusolex ® T 2000 | 5 | 2 | | | 10 | | | 10 | | 2 | |
| Veegum ® Ultra | 1.5 | | 1.5 | | | 1.5 | 1.2 | | 1 | | |
| Keltrol ® T | 0.5 | | 0.5 | | | 0.5 | 0.4 | | 0.5 | | |
| Cosmedia ® SP | | | 0.2 | 0.3 | | | 0.1 | | | 0.2 | |
| Pemulen ® TR 2 | | 0.3 | | 0.3 | | | | | 0.2 | | 0.3 |
| Ethanol | | 5 | | 8 | | | | | | | |
| Butylene glycol | 1 | | | 3 | 3 | | | | | 8 | 1 |
| Glycerin | 2 | 4 | 3 | 3 | | 3 | 3 | 3 | 5 | | 3 |
| Water/Preservative/NaOH | | | | | ad 100/q.s./q.s | | | | | | |

TABLE 6

| W/O sunscreen emulsions | | | | | | | | | | | |
|---|---|---|---|---|---|---|---|---|---|---|---|
| Component | 23 | 24 | 25 | 26 | 27 | 28 | 29 | 39 | 31 | 32 | 34 |
| C—Cream, L—Lotion | C | L | C | L | C | L | L | L | L | C | C |
| Eumulgin ® PRISMA | 0.05 | 0.1 | 0.2 | 0.1 | 0.2 | 0.1 | 0.3 | 0.1 | 0.4 | 0.1 | 0.2 |
| Dehymuls ® PGPH | 4 | 2 | 1 | 3 | 3 | 1 | 1 | 2 | 2 | 4 | 1 |
| Monomuls ® 90-O18 | | | 2 | | | | | | | | |
| Lameform ® TGI | 2 | | 4 | | 3 | | | | | 1 | 3 |
| Abil ® EM 90 | | | | | | | 4 | | | | |
| Isolan ® PDI | | | | | | 4 | | 2 | | | |
| Zinc Stearate | 1 | | | 1 | 1 | | | 1 | | 1 | |
| Beeswax | 1 | | 5 | 1 | | | | 5 | | 7 | 5 |
| Tego ® Care CG | | | | | 1 | | | | | | 0.5 |
| Cutina ® PES | 2 | 3 | 2 | 1 | 2 | 1 | 1 | 1 | 5 | 1 | 4 |
| Prisorine ® 3505 | | | 1 | | | 1 | 1 | | | | 1 |
| Cosmedia DC | 3 | 4 | 2 | 1 | 1 | 2 | 2 | 2 | 3 | 1 | 1 |
| Myritol ® 331 | 2 | | | | 3 | 6 | | | | | 8 |
| Finsolv ® TN | | | | 5 | | | 5 | | | | |
| Cetiol ® CC | 10 | 4 | 2 | | 4 | 2 | | | 2 | 3 | 5 |
| Tegosoft DEC | | 4 | | 3 | 2 | | 5 | 5 | | 3 | |
| Cetiol ® OE | | | | | 4 | | 5 | | 4 | 2 | |
| Dow Corning ® DC 244 | | | 3 | | | 2 | | | 4 | 4 | |
| Dow Corning ® DC 2502 | 1 | | 1 | | 2 | 1 | | | | | 1 |
| Wacker AK 350 silicone oil | | 1 | | 4 | | | | 3 | | | |
| Cetiol ® PGL | | 3 | | | 4 | | | 4 | | | |
| Copherol ® F 1300 | | | | | | 1 | | | | | |
| Magnesium sulfate × 7 Water | | | | | | 1 | | | | | |
| Neo Heliopan ® Hydro (Na salt) | 2 | | 2.2 | | 3 | 3 | | | 1 | | 2 |
| Neo Heliopan ® 303 | | 5 | | | | | | | 4 | | 4 |
| Uvasorb ® HEB | 1 | | | 1 | 1 | | | | | | 2 |

TABLE 6-continued

| Component | \multicolumn{11}{c}{W/O sunscreen emulsions} |
|---|---|---|---|---|---|---|---|---|---|---|---|
| | 23 | 24 | 25 | 26 | 27 | 28 | 29 | 39 | 31 | 32 | 34 |
| Neo Heliopan ® MBC | 2 | | | | | 2 | 2 | 2 | | | |
| Uvinul ® A plus | | | | | 2 | | | | 3 | 3 | |
| Neo Heliopan ® AP (Na salt) | | 2 | 2 | | 1 | | | | 1 | | 6 |
| Neo Heliopan ® AV | 3 | | 4 | 6 | 4 | 7.5 | 4 | 5 | | | 1 |
| Uvinul ® T 150 | | 1 | 1 | | 2.5 | | | 1 | | | |
| Parsol ® 1789 | 2 | 1 | | | | | 2 | | 2 | 2 | |
| Zinc oxide NDM | | | | | | 10 | | 3 | | | 4 |
| Tinosorb ® M | | 3 | | 3 | | | | 2 | | 2 | |
| Tinosorb ® S | | 3 | | 3 | | | | 2 | | 2 | |
| Eusolex ® T Aqua | | | 8 | | | | | 5 | | | |
| Eusolex ® T 2000 | | | | | 5 | | | 3 | 3 | | 4 |
| Ethanol | | | | | | | | | | 8 | |
| Glycerin | 5 | 3 | 3 | 3 | 5 | 3 | 2 | 3 | 10 | 4 | 3 |
| Water, Preservative | \multicolumn{11}{c}{ad 100, q.s.} |

TABLE 7

| Component | \multicolumn{12}{c}{Sprayable emulsions} |
|---|---|---|---|---|---|---|---|---|---|---|---|---|
| | 1 | 2 | 3 | 4 | 5 | 6 | 7 | 8 | 9 | 10 | 11 | 12 |
| S—Spray, SC—Sprayable cream | S | S | S | S | SC | S | S | S | S | S | S | S |
| Eumulgin ® PRISMA | 0.5 | 0.5 | 0.2 | 0.3 | 0.2 | 0.2 | 0.2 | 0.3 | 0.3 | 0.3 | 0.3 | 0.55 |
| Eumulgin ® B2 | | | | | | 1 | | | | | | |
| Eumulgin ® HRE 40 | | | | | | | 1 | | | | | |
| Lanette ® E | | | 0.2 | 0.1 | | | | | | | | |
| Amphisol ® K | | | | 1 | | | | | | | | |
| Emulgade ® CM | | | | | | | 20 | | | | | |
| Emulgade ® SE-PF | | | | | | 4.5 | | | | | | |
| Emulgade ® PL 68/50 | | | 1 | | | | | | | | | |
| Dehyquart ® C 4046 | | | | | 6 | | | | | | | |
| Cutina ® MD | | | | | | | | 0.5 | | 0.25 | 0.25 | 0.25 |
| Cutina ® PES | 1 | 1 | 2.5 | 2.5 | 3 | 1 | 2 | | 0.25 | | | |
| Lanette ® O | | | | | | | | | 0.25 | 0.1 | | |
| Cosmedia ® DC | 1 | | | 2 | | 1.5 | 0.5 | | | | | |
| Antaron ® V 216 | | | 2 | | | | | | | | | |
| Lanolin, anhydrous USP | | | 1 | | | | | | | | | |
| Myritol ® 331 | 10 | 10 | 8 | 8 | | | | | | | | |
| Finsolv ® TN | | | 1 | | | | | | | | | |
| Cetiol ® CC | 6 | 6 | 5 | 5 | 4 | | | 1 | 1 | 1 | 4.5 | 10 |
| Cetiol ® OE | | | 3 | | | 5 | | | | | | |
| Cetiol ® SN | | | | 4 | | | | | | | | |
| Dow Corning DC ® 244 | | | 1 | | | | | | | | | |
| Cetiol ® S | | | | | | 5 | | | | | | |
| Cetiol ® B | | | 1 | | | | | | | | | |
| Cetiol ® 868 | | | | | | | | 1 | 1 | 1 | | |
| Cetiol ® SB 45 | | | | | | | | | | | 0.5 | 0.5 |
| Cegesoft ® PS6 | | | | | | | | 1 | 1 | 1 | | |
| Almond oil | | | 2 | | | | | | | | | |
| Panthenol | | | | | | | 1 | | | | | |
| Bisabolol | | | | | | | 0.2 | | | | | |
| Tocopherol/Tocopheryl acetate | | | | | | | 1 | | | | | |
| Neo Heliopan ® 303 | | | 2.2 | 9 | | | | | | | | |
| Neo Heliopan ® BB | | | 9 | | | | | | | | | |
| Neo Heliopan ® AV | 7.5 | 7.5 | | | | | | | | | | |
| Uvinul ® A PLUS | | | 7.5 | 2 | | | | | | | | |
| Tinosorb ® S | | | 3 | | | | | | | | | |
| Uvasorb ® HEB | | | 1 | | | | | | | | | |
| Parsol ® 1789 | 2 | 2 | | | | | | | | | | |
| Zinc oxide NDM | | | 1 | | | | | | | | | |
| Z-Cote HP 1 | | | | 5 | | | | | | | | |
| Eusolex ® T 2000 | | | 5 | | | | | | | | | |
| Veegum ® Ultra | | | | 1.2 | | | | | | | | |
| Keltrol ® T | | | 0.75 | 0.4 | 1 | | | | | | | |
| Cosmedia ® SP | 0.3 | 0.3 | 0.25 | 0.1 | | | | 0.25 | | 0.25 | 0.25 | 0.5 |
| Locron ® L | | | | | 10 | | | | | | | |
| Hydagen ® C.A.T. | | | | | 2 | | | | | | | |
| Ethanol | | | | | | | | | | | | |
| Butylene glycol | | | | | | | | | | | | |

TABLE 7-continued

| | Sprayable emulsions | | | | | | | | | | | |
|---|---|---|---|---|---|---|---|---|---|---|---|---|
| Component | 1 | 2 | 3 | 4 | 5 | 6 | 7 | 8 | 9 | 10 | 11 | 12 |
| Citric acid | | | | | | | | | | | | 0.15 |
| Glycerin | 5 | 5 | 5 | 3 | 2 | 5 | | | | | | |

Preservative q.s., NaOH q.s., Water ad 100

TABLE 8

| | O/W care emulsions | | | | | | | | | | |
|---|---|---|---|---|---|---|---|---|---|---|---|
| Component | 1 | 2 | 3 | 4 | 5 | 6 | 7 | 8 | 9 | 10 | 11 |
| C—Cream, L—Lotion | C | C | C | L | C | L | L | C | L | C | C |
| Eumulgin ® PRISMA | 0.5 | 1.5 | 1.0 | 1.0 | 0.3 | 0.8 | 0.8 | 0.5 | 0.14 | 1.0 | 1.5 |
| Eumulgin ® VL 75 | | | | | | | | | | 1.5 | |
| Dehymuls ® PGPH | | 0.6 | | | | | | | | | |
| Generol ® R | | | 0.5 | | | | | | | | |
| Eumulgin ® B2 | | | 0.1 | | | | | | | | |
| Hostaphat ® KL 340 N | | | | | | | | | 0.5 | | |
| Lanette ® E | | | | | | | | 0.6 | | | |
| Amphisol ® K | | 0.2 | | | | | | | | | |
| Sodium stearate | | | | | 0.5 | | | | | | |
| Emulgade ® PL 68/50 | | | | | | | | | | | 1.2 |
| Tego ® Care CG 90 | 0.7 | | | | | | | | | | |
| Tego ® Care 450 | | | | | 0.4 | | | | | | |
| Cutina ® PES | 2.5 | 2 | 3 | | | 2 | | 2.5 | 1.7 | 2.5 | 1.5 | 1.2 |
| Cutina ® MD | | | 1 | 3 | 5 | | 2 | | | 6 | |
| Lanette ® 14 | | | | 1 | | | | 4 | | | 4 |
| Lanette ® O | 4.5 | | 4 | | 1 | 2 | | | | | 2 |
| Novata ® AB | | 1 | | | | | | | | | 1 |
| Emery ® 1780 | | | | | 0.5 | 0.5 | | | | | |
| Lanolin, anhydrous, USP | | | | | | | 1.1 | | | | |
| Cosmedia ® DC | | 1.5 | 2 | | | 1.5 | 2 | | 1.5 | 1.5 | |
| Cetiol ® SB 45 | | | 1.5 | | | | 2 | | | | |
| Cegesoft ® C 17 | | | | | | | | | | | 2 |
| Myritol ® PC | | | | | 5 | | | | | | |
| Myritol ® 331 | 2 | 5 | 5 | | | 6 | | 12 | | | |
| Finsolv ® TN | | | 2 | | | 2 | | | 8 | | |
| Cetiol ® CC | 4 | 6 | | | | 4 | 4 | | | | 5 |
| Cetiol ® OE | | | | 5 | | | | | 4 | 3 | |
| Dow Corning DC ® 245 | | | 2 | | 5 | 1 | | | | | |
| Dow Corning DC ® 2502 | | | | | 2 | 1 | | | | | 5 |
| Prisorine ® 3758 | | | | | | 1 | | | | | |
| Wacker AK ® 350 silicone oil | 0.5 | 0.5 | 0.5 | | | 1 | 4 | | | | |
| Cetiol ® 868 | | | | | 2 | | 4 | | | | |
| Cetiol ® J 600 | 2 | | 3 | | 3 | 2 | | | | 5 | |
| Ceraphyl ® 45 | | | | | | | 3 | | | | |
| Mineral oil | | | | 9 | | | | | | | |
| Cetiol ® SN | | | | 5 | | | | | | | |
| Cetiol ® B | | | | | | | | 4 | | 2 | |
| Eutanol ® G | | 2 | | 3 | | | | | | | |
| Cetiol ® PGL | | | | | | | | | 5 | 5 | |
| Dry Flo ® Plus | 5 | | | | | | 1 | | | | |
| SFE 839 | 5 | | | | | | | | | | 2 |
| Almond oil | | | | | | | 1 | | | | |
| Insect Repellent ® 3535 | | 2 | 4 | | | 2 | | | | 3 | |
| N,N-Diethyl-m-toluamide | | 2 | | | | | | | | 3 | |
| Photonyl ® LS | 2 | 2 | | | | 2 | | | | | |
| Panthenol | | | | | | | 1 | | | | |
| Bisabolol | | | | | | | 0.2 | | | | |
| Tocopherol/Tocopheryl acetate | | | | | | | 1 | | | | |
| Veegum ® Ultra | | | | | | | | | 1 | | |
| Keltrol ® T | | | | 0.4 | | | | | 0.5 | | |
| Cosmedia ® SP | | 0.3 | | | 0.2 | 0.2 | | | 0.2 | 0.3 | |
| Pemulen ® TR 2 | 0.3 | | | | | | | 0.3 | | | |
| Carbopol ® Ultrez 10 | | | 0.3 | | | 0.2 | | | | | |
| Ethanol | | | | | | | | | | 10 | |
| Butylene glycol | | | | 4 | 3 | | 2 | 5 | 2 | | |
| Glycerin | 2 | 5 | 5 | | 3 | 3 | 2 | | 4 | | 3 |

Water ad 100, Preservative q.s., NaOH q.s., q.s., pH 6.5-7.5

TABLE 9

O/W care emulsions

| Component | 12 | 13 | 14 | 15 | 16 | 17 | 18 | 19 | 20 | 21 | 22 |
|---|---|---|---|---|---|---|---|---|---|---|---|
| C—Cream, L—Lotion | C | C | L | C | L | C | C | L | L | L | C |
| Eumulgin ® PRISMA | 1.5 | 1 | 0.5 | 1 | 0.2 | 0.5 | 1 | 0.6 | 0.6 | 0.3 | 1 |
| Eumulgin ® VL 75 | | | | | | | | | | | 1 |
| Generol ® R | | | | | | 0.3 | | | | | |
| Eumulgin ® B2 | | | | | | | | | 1 | | |
| Tween ® 60 | | | | | | | | | 1 | | |
| Cutina ® E 24 | | | | 0.5 | | | | | | | |
| Amphisol ® K | | 0.5 | | | | | | | | | |
| Sodium stearate | | | | | 1 | | | | | | |
| Emulgade ® PL 68/50 | | | | | | | | 1 | | | |
| Tego ® Care 450 | | | | | | | | | 1 | | |
| Cutina ® PES | | 2 | 1 | 3 | 2.5 | 2 | | 1.2 | 2.5 | 1.5 | 0.8 |
| Cutina ® MD | 3 | 1 | | 4 | | 4 | | | | | |
| Lanette ® 14 | | 2 | | | 1 | | | 2 | | 1 | |
| Lanette ® O | 2 | | | 2 | | 3 | 1 | | 1 | 1 | 6 |
| Novata ® AB | | | | | | | | | 1 | 1 | |
| Emery ® 1780 | | | | | | | | | | | 0.5 |
| Lanolin, anhydrous, USP | | | | | 4 | | | | | | |
| Cosmedia ® DC | | | 1 | | 1.5 | | | | 1 | 1 | |
| Cetiol ® SB 45 | | | | | | | 2 | | | | |
| Cegesoft ® C 17 | 4 | | | | | | | | | | |
| Myritol ® PC | 6 | | | | 5 | | | 5 | | | |
| Myritol ® 331 | 5 | | 5 | | | | 7 | | 10 | | 3 |
| Finsolv ® TN | | 5 | | 4 | 5 | | | 3 | 3 | | 1 |
| Cetiol ® CC | | | 8 | 6 | | | | 4 | 3 | | 2 |
| Cetiol ® OE | | | | | 2 | | 2 | | 5 | | |
| Dow Corning DC ® 245 | | 2 | | | 1 | 8 | | | | 8 | 2 |
| Dow Corning DC ® 2502 | | 1 | | 1 | | | | | | | 3 |
| Prisorine ® 3758 | 3 | | | | | | | | | | 2 |
| Wacker AK ® 350 silicone oil | | | | | 1 | | | | | | 1 |
| Cetiol ® 868 | | 2 | | | | | | | | | |
| Cetiol ® J 600 | | 2 | | 2 | | | | | | | |
| Ceraphyl ® 45 | | | | | | | 3 | | | | |
| Cetiol ® SN | | | 5 | | | | | | | | |
| Cetiol ® B | | | | | 5 | | 4 | | | | 3 |
| Eutanol ® G | | 3 | | 5 | | | | | | | |
| Cetiol ® PGL | | | | | | | | 5 | 2 | | |
| Dry Flo ® Plus | | 1 | | | | | | | | | 1 |
| SFE 839 | 1 | 1 | | | | | | | | | |
| Almond oil | | | | | 2 | | | | | | |
| Photonyl ® LS | | | | | 2 | | | | | | |
| Panthenol | | | | | | 1 | | | | | |
| Bisabolol | | | | | | 0.2 | | | | | |
| Tocopherol/Tocopheryl acetate | | | | | | 1 | | | | | |
| Veegum ® Ultra | | | | | | | | | 1 | | |
| Keltrol ® T | | | | | | | | | 0.5 | | |
| Cosmedia ® SP | 0.1 | | 1 | | 0.2 | 0.2 | 0.2 | 0.2 | | | 0.5 |
| Carbopol ® ETD 2001 | | | 0.3 | | 0.3 | | | | | | |
| Pemulen ® TR 2 | | | | | | 0.3 | | | | | |
| Ethanol | | 5 | | 8 | | | | | | | 10 |
| Butylene glycol | 5 | | | 3 | 3 | | | | | 8 | |
| Glycerin | 2 | 4 | 3 | 3 | | 7 | 5 | 3 | 5 | | |

Water ad 100, Preservative q.s., NaOH (pH 6.5-7.5)

TABLE 10

O/W care emulsions

| Components | 45 | 46 | 47 | 48 | 49 |
|---|---|---|---|---|---|
| C—Cream, L—Lotion, SC = sprayable cream | SC | C | C | L | C |
| Eumulgin ® PRISMA | 0.2 | 0.3 | 0.5 | 0.2 | 0.2 |
| Dehyquart ® C 4046 | 6 | | | 3 | |
| Cutina ® GMS-SE | | | 2 | | 5.5 |
| Cutina ® FS 45 | | | | | 1.5 |
| Eumulgin ® B2 | | 1 | | | |
| Cutina ® PES | 3 | 2 | 2 | 2 | 2 |
| Cutina ® MD | | 1.5 | | | |
| Cosmedia ® DC | | | | 0.5 | |
| Cegesoft ® PS 6 | | | | 4.5 | |
| Cegesoft ® SH | | 7 | 3 | | |
| Myritol ® 331 | | | 5 | 4.5 | |
| Cetiol ® CC | 4 | | 3 | 3 | |
| Cetiol ® OE | | 1 | | | |
| Wacker AK ® 350 | | | | | 0.5 |

TABLE 10-continued

O/W care emulsions

| Components | 45 | 46 | 47 | 48 | 49 |
|---|---|---|---|---|---|
| C—Cream, L—Lotion, SC = sprayable cream | SC | C | C | L | C |
| silicone oil | | | | | |
| Paraffin Liquid | | | | | 6 |
| Isopropyl palmitate | | | | 2 | |
| Cetiol ® 868 | | 7 | 8 | | |
| Cetiol ® SN | 4 | | | | 3 |
| Eutanol ® G | | | | | 3 |
| Almond oil | | 7 | | | |
| Panthenol | 1 | 0.2 | 1 | | |
| Bisabolol | 1 | | | | |
| Tocopherol/Tocopheryl acetate | 0.2 | | | | |
| Keltrol ® T | 1 | | | | |
| Cosmedia ® SP | | 1 | 0.7 | 0.45 | |
| Glycerin | 2 | 5 | 5 | 5 | |
| Water, preservative, NaOH | ad 100, q.s., (pH 6.5-7.5) | | | | |

TABLE 11

| Components (INCI) | 1 | 2 | 3 | 4 | 5 | 6 | 7 |
|---|---|---|---|---|---|---|---|
| Eumulgin ® PRISMA (Disodium Cetearyl Sulfosuccinate) | 0.1 | 0.05 | 0.2 | 0.15 | 0.2 | 0.9 | 1.1 |
| Glyceryl Stearate, Ceteareth-20, Ceteareth-12, Cetearyl Alcohol, Cetyl Palmitate (Emulgade ® SE) | 6 | | 4.5 | | | 6 | |
| Ceteareth-12 (Eumulgin ® B1) | | | | | | | |
| Ceteareth-20 (Eumulgin ® B2) | | | | 1 | | | |
| Aqua, Cetearyl Isononanoate, Glyceryl Stearate, Ceteareth-20, Ceteareth-12, Cetearyl Alcohol, Cetyl Palmitate (Emulgade ® CM) | | | | | 20 | | |
| Polyglyceryl-3 Diisostearate Lameform TGI | | 3 | | | | | |
| Cocoglycerides (Novata ® AB) | | | | | | | 4 |
| Stearyl alcohol (Lanette 18) | | | | 10 | | | |
| Hydrogenated Castor Oil (Cutina ® HR) | | | | 3.7 | | | 6.5 |
| Polyglyceryl-2 Dipolyhydroxystearate (Dehymuls ® PGPH) | | 1 | | | | | |
| Sodium Cetearyl Sulfate (Lanette ® E) | 0.3 | | | | | 0.3 | |
| Pentaerythrityl Distearate (Cutina ® PES) | 1.5 | 2 | 1 | 4.7 | 2 | 5 | 4 |
| Behenyl Alcohol (Lanette ® 22) | 2 | | | | | 4 | |
| Dicaprylyl Carbonate (Cetiol ® CC) | | 7 | | | | | |
| Dicaprylyl Ether (Cetiol ® OE) | 6 | | 5 | 9 | | 6 | 9 |
| Cocoglycerides (Myritol ® 331) | | | | | | | |
| Diethylhexylcyclohexane (Cetiol ® S) | | | 5 | 14.7 | | | 35 |
| Cyclopentasiloxane | 3 | 5 | | 34 | | 3 | 14 |
| Cyclopentasiloxane and Dimethicone/Vinyldimethicone Crosspolymer SFE 839 (GE Bayer) | | 3 | | | | | |
| Dimethicone | 1 | | | | | | |
| Hydrogenated Dimer Dilinoleyl/Dimethylcarbonate Copolymer (Cosmedia ® DC) | 0.5 | 1 | 1.5 | 1 | 0.5 | 2 | 1 |
| Triethyl Citrate (Hydagen ® C.A.T) | | | 2 | | | | |
| PEG-40 Hydrogenated Castor Oil | | | | | 1 | | |
| Tocopheryl Acetate | | | | 1 | | | |
| Aluminium Zirconium Tetrachlorohydrex GLY (Rezal 36) | 30 | 40 | | 22.9 | | 30 | 25 |
| Aluminum Chlorohydrate (Locron L) | | | 10 | | | | |
| Chitosan (Hydagen ® DCMF) | 0.05 | | | | | | |
| Glycolic Acid | 0.02 | | | | | | |
| Glycerin | | 5 | 5 | | | | |
| Propylene Carbonate (Fluka) | | | | | | | 0.5 |
| Quaternium-18 Hectorite (Bentone 18) | | | | | | | 1 |
| Talc (Merck) | | | | | | 5 | 5 |
| MgSO$_4$ × 7H$_2$O | | | 1 | | | | |
| Water | | | | | Ad 100 | | |
| Perfume, Preservatives | q.s. | q.s. | q.s. | q.s. | q.s. | q.s. | q.s. |

1—Antiperspirant/Deodorant cream; 2—Antiperspirant cream (W/O); 3—Antiperspirant/Deodorant spray; 4—Antiperspirant stick with Vitamin E; 5—Deodorant wipe formulation; 6—Antiperspirant cream; 7—Antiperspirant "Soft solid" cream

TABLE 12

O/W care emulsions

| | Components | | | | | | | | | | |
|---|---|---|---|---|---|---|---|---|---|---|---|
| | 1 | 2 | 3 | 4 | 5 | 6 | 7 | 8 | 9 | 10 | 11 |
| | C—Cream, L—Lotion | | | | | | | | | | |
| | C | C | C | L | C | L | L | C | L | C | C |
| Eumulgin ® PRISMA | 0.5 | 1.5 | 1.0 | 1.0 | 0.3 | 0.8 | 0.8 | 0.5 | 0.14 | 1.0 | 1.5 |
| Emulgade ® Sucro | 2.5 | 2 | 3 | 2 | 2 | 2.5 | 2.5 | 1.7 | 2.5 | 1.5 | 1.2 |
| Generol ® R | | | 0.5 | | | | | | | | |
| Eumulgin ® B2 | | | 0.1 | | | | | | | | |
| Hostaphat ® KL 340 N | | | | | | | | | 0.5 | | |
| Lanette ® E | | | | | | | | 0.6 | | | |
| Amphisol ® K | | 0.2 | | | | | | | | | |
| Sodium Stearate | | | | | 0.5 | | | | | | |
| Emulgade ® PL 68/50 | | | | | | | | | | | 1.2 |
| Tego ® Care CG | 0.7 | | | | | | | | | | |
| Tego ® Care 450 | | | | | 0.4 | | | | | | |
| Cutina ® PES | | | | | | | | | 2.5 | | |
| Cutina ® MD | | 1 | | 3 | 5 | | 2 | | | 6 | |
| Lanette ® 14 | | | | 1 | | | | 4 | | | 4 |
| Lanette ® O | 4.5 | | 4 | | 1 | 2 | | | | | 2 |
| Novata ® AB | | 1 | | | | | | | | | 1 |
| Emery ® 1780 | | | | | 0.5 | 0.5 | | | | | |
| Lanolin, anhydrous, USP | | | | | | | 1.1 | | | | |
| Cosmedia ® DC | | 1.5 | 2 | | | 1.5 | 2 | | 1.5 | 1.5 | |
| Cetiol ® SB 45 | | | 1.5 | | | | 2 | | | | |
| Cegesoft ® C 17 | | | | | | | | | | | 2 |
| Myritol ® PC | | | | | 5 | | | | | | |
| Myritol ® 331 | 2 | 5 | 5 | | | 6 | | 12 | | | |
| Finsolv ® TN | | | 2 | | | 2 | | | 8 | | |
| Cetiol ® CC | 4 | 6 | | | | 4 | 4 | | | | 5 |
| Cetiol ® OE | | | | 5 | | | | | 4 | 3 | |
| Dow Corning DC ® 245 | | | 2 | | 5 | 1 | | | | | |
| Dow Corning DC ® 2502 | | | | | 2 | 1 | | | | | 5 |
| Prisorine ® 3758 | | | | | 1 | | | | | | |
| Silicone Oil Wacker AK ® 350 | 0.5 | 0.5 | 0.5 | | | 1 | 4 | | | | |
| Cetiol ® 868 | | | | | 2 | | 4 | | | | |
| Cetiol ® J 600 | 2 | | 3 | | 3 | 2 | | | | 5 | |
| Ceraphyl ® 45 | | | | | | | 3 | | | | |
| Mineral oil | | | | | 9 | | | | | | |
| Cetiol ® SN | | | | | 5 | | | | | | |
| Cetiol ® B | | | | | | | | 4 | | 2 | |
| Eutanol ® G | | 2 | | 3 | | | | | | | |
| Cetiol ® PGL | | | | | | | | | 5 | 5 | |
| Dry Flo ® Plus | 5 | | | | | | 1 | | | | |
| SFE 839 | 5 | | | | | | | | | | 2 |
| Almond Oil | | | | | | | 1 | | | | |
| Insect Repellent ® 3535 | | 2 | 4 | | | 2 | | | | 3 | |
| N,N-Diethyl-m-toluamide | | 2 | | | | | | | | 3 | |
| Photonyl ® LS | 2 | 2 | | | | 2 | | | | | |
| Panthenol | | | | | | | 1 | | | | |
| Bisabolol | | | | | | | 0.2 | | | | |
| Tocopherol/Tocopheryl Acetate | | | | | | | 1 | | | | |
| Veegum ® Ultra | | | | | | | | | 1 | | |
| Keltrol ® T | | | | 0.4 | | | | | 0.5 | | |
| Cosmedia ® SP | | 0.3 | | 0.2 | 0.2 | | | 0.2 | 0.3 | | |
| Pemulen ® TR 2 | 0.3 | | | | | | | 0.3 | | | |
| Carbopol ® Ultrez 10 | | | 0.3 | | 0.2 | | | | | | |
| Ethanol | | | | | | | | | | 10 | |
| Butylene glycol | | | | 4 | 3 | | 2 | 5 | 2 | | |
| Glycerin | 2 | 5 | 5 | | 3 | 3 | 2 | | 4 | | 3 |
| Water, Preservative, NaOH | ad 100, q.s., pH 6.5-7.5 | | | | | | | | | | |

TABLE 13

O/W care emulsions

| Component | 12 | 13 | 14 | 15 | 16 | 17 | 18 | 19 | 20 | 21 | 22 |
|---|---|---|---|---|---|---|---|---|---|---|---|
| | C | C | L | C | L | C | C | L | L | L | C |
| Eumulgin ® SG | 1.5 | 1 | 0.5 | 1 | 0.2 | 0.5 | 1 | 0.6 | 0.6 | 0.3 | 1 |
| Emulgade ® Sucro | 1 | 2 | 1 | 3 | 2.5 | 2 | 1 | 1.2 | 2.5 | 1.5 | 1.0 |
| Generol ® R | | | | | | 0.3 | | | | | |
| Eumulgin ® B2 | | | | | | | | | | 1 | |
| Tween ® 60 | | | | | | | | | | 1 | |
| Cutina ® E 24 | | | | 0.5 | | | | | | | |
| Amphisol ® K | | 0.5 | | | | | | | | | |
| Sodium stearate | | | | | 1 | | | | | | |
| Emulgade ® PL 68/50 | | | | | | | 1 | | | | |
| Tego ® Care 450 | | | | | | | | 1 | | | |
| Cutina ® PES | | | | | | | | | | | 0.8 |
| Cutina ® MD | 3 | 1 | | 4 | | | 4 | | | | |
| Lanette ® 14 | | 2 | | | 1 | | 2 | | 1 | | |
| Lanette ® O | 2 | | | 2 | | 3 | 1 | | 1 | 1 | 6 |
| Novata ® AB | | | | | | | | 1 | 1 | | |
| Emery ® 1780 | | | | | | | | | | | 0.5 |
| Lanolin, anhydrous, USP | | | | | 4 | | | | | | |
| Cosmedia ® DC | | | 1 | | | 1.5 | | 1 | 1 | | |
| Cetiol ® SB 45 | | | | | | 2 | | | | | |
| Cegesoft ® C 17 | 4 | | | | | | | | | | |
| Myritol ® PC | 6 | | | | | 5 | | 5 | | | |
| Myritol ® 331 | 5 | | 5 | | | | 7 | | | 10 | 3 |
| Finsolv ® TN | | 5 | | 4 | 5 | | | 3 | 3 | | 1 |
| Cetiol ® CC | | | 8 | 6 | | | 4 | 3 | | | 2 |
| Cetiol ® OE | | | | | 2 | | 2 | | 5 | | |
| Dow Corning DC ® 245 | | 2 | | | 1 | 8 | | | 8 | | 2 |
| Dow Corning DC ® 2502 | | 1 | | | 1 | | | | | | 3 |
| Prisorine ® 3758 | 3 | | | | | | | | | | 2 |
| Wacker AK ® 350 silicone oil | | | | | 1 | | | | | | 1 |
| Cetiol ® 868 | | 2 | | | | | | | | | |
| Cetiol ® J 600 | | 2 | | 2 | | | | | | | |
| Ceraphyl ® 45 | | | | | | | 3 | | | | |
| Cetiol ® SN | | | | 5 | | | | | | | |
| Cetiol ® B | | | | | | 5 | | 4 | | | 3 |
| Eutanol ® G | | 3 | | | 5 | | | | | | |
| Cetiol ® PGL | | | | | | | | 5 | 2 | | |
| Dry Flo ® Plus | | | 1 | | | | | | | | 1 |
| SFE 839 | 1 | 1 | | | | | | | | | |
| Almond oil | | | | | | 2 | | | | | |
| Photonyl ® LS | | | | | | 2 | | | | | |
| Panthenol | | | | | | 1 | | | | | |
| Bisabolol | | | | | | 0.2 | | | | | |
| Tocopherol/Tocopheryl acetate | | | | | | 1 | | | | | |
| Veegum ® Ultra | | | | | | | | | 1 | | |
| Keltrol ® T | | | | | | | | | 0.5 | | |
| Cosmedia ® SP | 0.1 | | 1 | | 0.2 | 0.2 | 0.2 | 0.2 | | | 0.5 |
| Carbopol ® ETD 2001 | | 0.3 | | 0.3 | | | | | | | |
| Pemulen ® TR 2 | | | | | 0.3 | | | | | | |
| Ethanol | | | 5 | | 8 | | | | | 10 | |
| Butylene glycol | 5 | | | 3 | 3 | | | | 8 | | |
| Glycerin | 2 | 4 | 3 | 3 | | 7 | 5 | 3 | 5 | | |
| Water, preservative, NaOH | ad 100, q.s., (pH 6.5-7.5) | | | | | | | | | | |

TABLE 14

Examples of tinted day cream of the O/W type

| Ingredient | 1 | 2 | 3 | 4 | 5 | 6 | 7 | 8 |
|---|---|---|---|---|---|---|---|---|
| Eumulgin ® PRISMA | 0.5 | 1.0 | 2.0 | 0.5 | 0.5 | 2.0 | 2.0 | 1.0 |
| Emulgade ® Sucro | 1.0 | 1.0 | 1.5 | 1.5 | 2.0 | 1.0 | 2.0 | 1.5 |
| Cutina ® GMS-SE | 5.5 | | | | | | | 3.0 |
| Emulgade ® PL 68/50 | | | 5.0 | | | 2.0 | | |
| Eumulgin ® VL 75 | | | | 3.0 | | | 5.0 | |
| Tego Care ® 450 | | | | | 2.0 | 2.0 | | |
| Crodesta ® F-50 | | | | | 6.0 | | | |
| Amphisol ® K | | | | 2.0 | | | | |
| Lanette ® E | | 0.25 | | | 1.0 | 1.0 | | |
| Cutina ® FS 45 | 1.5 | | | | | | | |
| Eumulgin ® B 2 | | | 2.0 | | | | | 2.0 |
| Cutina ® PES | 1.0 | | 0.5 | 2.0 | | 0.2 | 0.5 | |
| Lanette ® O | | | 2.0 | | | | | 1.0 |
| Cutina ® MD | | 0.5 | 3.0 | 3.0 | | | | |
| Cetiol ® LC | 4.0 | 5.0 | | | | | | |
| Cosmedia ® DC | 0.5 | | 1.0 | | | | | 1.0 |
| Cetiol ® CC | 4.0 | | 4.0 | | 7.0 | 5.0 | 10.0 | |
| Tegosoft ® DEC | | 5.0 | 2.0 | 4.0 | 2.0 | 2.0 | | 6.0 |

TABLE 14-continued

Examples of tinted day cream of the O/W type

| Ingredient | 1 | 2 | 3 | 4 | 5 | 6 | 7 | 8 |
|---|---|---|---|---|---|---|---|---|
| Dow Corning ® 245 | | 2.0 | | 2.0 | | | | 2.0 |
| Eutanol ® G 16 | 4.0 | | | | 3.0 | 3.0 | | |
| Myritol ® 331 | | 5.0 | | | 2.0 | 2.0 | 5.0 | |
| Uvinul ® T 150 | | | | 0.5 | | | | 0.5 |
| Uvasorb ® HEB | 2.0 | | | | | | 1.0 | 1.0 |
| Tinosorb ® M | | | 2.0 | | | | | |
| Tinosorb ® S | | | | 3.0 | | | | 2.0 |
| Neo Heliopan ® AV | | | | 2.0 | | 2.0 | | |
| Heo Heliopan ® AP | | | | 1.0 | | 1.0 | | |
| Uvinul ® A plus | | | 1 | | | | 2.0 | 2.0 |
| Microna ® Matte White | 5.0 | 5.0 | | 5.0 | 5.0 | 5.0 | | 5.0 |
| Microna ® Matte Black | 0.3 | 0.3 | 0.1 | 0.3 | 0.3 | 0.3 | 0.4 | 0.3 |
| Microna ® Matte Yellow | 3.0 | 3.0 | | 3.0 | 3.0 | 3.0 | 2.0 | 3.0 |
| Microna ® Matte Red | 0.6 | 0.6 | 1.0 | 0.6 | 0.6 | 0.6 | 1.0 | 0.6 |
| Ronasphere ® LDP | 1.0 | 1.0 | | 1.0 | 1.0 | 1.0 | | 1.0 |
| Pigment White 6 | | | 6.0 | | | | 6.0 | |
| Dry Flow PC | | | | | | | 2.0 | 2.0 |
| Glycerin | 5.0 | 5.0 | 3.0 | 5.0 | 5.0 | 5.0 | 3.0 | |
| Cosmedia ® SP | | | 0.3 | | 0.2 | | | |
| Water, deionized, Preservative | ad 100 | | | | | | | |

TABLE 15

Examples of tinted day cream of the W/O type

| Ingredient | 1 | 2 | 3 | 4 | 5 | 6 | 7 | 8 |
|---|---|---|---|---|---|---|---|---|
| Eumulgin ® SG | 0.1 | 0.2 | 0.15 | 0.3 | 0.1 | 0.05 | 0.1 | 0.01 |
| Emulgade ® Sucro | 0.1 | 0.2 | 0.1 | 0.3 | 0.2 | 0.4 | 0.1 | 0.1 |
| Dehymuls ® PGPH | 5.5 | | 4.0 | | | | | 3.0 |
| Lameform ® TGI | | 5.0 | | | | 2.0 | | |
| Abil ® EM 90 | | | | | 3.0 | | 5.0 | |
| Isolan ® GI 34 | | | | | | 2.0 | 2.0 | |
| Isolan ® PDI | | | | | 6.0 | | | |
| Admul ® WOL 1403 | | | | 2.0 | | | | |
| Dehymuls ® HRE 7 | | 1.0 | | | 1.0 | 1.0 | | |
| Monomuls ® 90-O18 | 1.5 | | | | | | | 2.0 |
| Cutina ® PES | 2.0 | 1.0 | | 4.0 | | 1.0 | 2.5 | 2.0 |
| Cera Bellina | | | 2.0 | | | | | 2.0 |
| Beeswax | | | 2.0 | | | 2.0 | | 1.0 |
| Microcrystalline Wax | | 1.5 | 3.0 | 3.0 | | | | |
| Cetiol ® LC | 4.0 | 5.0 | | | | | | |
| Cosmedia ® DC | 1.0 | | | | 0.5 | | 1.0 | |
| Cetiol ® CC | 4.0 | | | | 7.0 | 5.0 | 10.0 | |
| Tegosoft ® DEC | | 5.0 | 2.0 | 4.0 | 2.0 | 2.0 | | 6.0 |
| Dow Corning ® 245 | | 2.0 | | 2.0 | | | | 2.0 |
| Eutanol ® G 16 | 4.0 | | | | 3.0 | 3.0 | | |
| Myritol ® 331 | | 5.0 | | | 2.0 | 2.0 | 5.0 | |
| Uvinul ® T 150 | | | | 0.5 | | | | 0.5 |
| Uvasorb ® HEB | | | 2.0 | | | | 1.0 | 1.0 |
| Tinosorb ® M | | | 2.0 | | | | | 2.0 |
| Tinosorb S | | | | 3.0 | | | | 2.0 |
| Neo Heliopan ® AV | | | | 2.0 | | | 2.0 | |
| Heo Heliopan ® AP | | | | 1.0 | | | 1.0 | |
| Uvinul ® A plus | | | 1.0 | | | | 2.0 | 2.0 |
| Microna ® Matte White | 5.0 | 5.0 | | 5.0 | 5.0 | 5.0 | | 5.0 |
| Microna ® Matte Black | 0.3 | 0.3 | 0.1 | 0.3 | 0.3 | 0.3 | 0.4 | 0.3 |
| Microna ® Matte Yellow | 3.0 | 3.0 | 3.5 | 3.0 | 3.0 | 3.0 | 2.0 | 3.0 |
| Microna ® Matte Red | 0.6 | 0.6 | 1.0 | 0.6 | 0.6 | 0.6 | 1.0 | 0.6 |
| Ronasphere ® LDP | 1.0 | 1.0 | | 1.0 | 1.0 | 1.0 | | 1.0 |
| Pigment White 6 | | | 6.0 | | | | 6.0 | |
| Dry Flow PC | | | | | | | 2.0 | 2.0 |
| Glycerin | 5.0 | 5.0 | 3.0 | 5.0 | 5.0 | 5.0 | 3.0 | |
| Water, deionized, Preservative | ad 100 | | | | | | | |

TABLE 16

| Components (INCI) | 1 | 2 | 3 | 4 | 5 | 6 | 7 | 8 |
|---|---|---|---|---|---|---|---|---|
| Disodium Cetearyl Sulfosuccinate (Eumulgin ® PRISMA) | 0.1 | 0.05 | 0.2 | 0.15 | 0.2 | 0.9 | 1.1 | 0.05 |
| Sucrose Polystearate, Hydrogenated Polyisobutene (Emulgade ® Sucro) | 0.5 | 0.1 | 0.4 | 0.6 | 0.2 | 0.3 | 0.5 | 0.1 |
| Glyceryl Stearate, Ceteareth-20, Ceteareth-12, Cetearyl Alcohol, Cetyl Palmitate (Emulgade ® SE) | 6 | | 4.5 | | | | 6 | |
| Ceteareth-12 (Eumulgin ® B1) | | | | | | | | |
| Ceteareth-20 (Eumulgin ® B2) | | | | 1 | | | | |
| Agua, Cetearyl Isononanoate, Glyceryl Stearate, Ceteareth-20, Ceteareth-12, Cetearyl Alcohol, | | | | | 20 | | | |

TABLE 16-continued

| Components (INCI) | 1 | 2 | 3 | 4 | 5 | 6 | 7 | 8 |
|---|---|---|---|---|---|---|---|---|
| Cetyl Palmitate (Emulgade ® CM) | | | | | | | | |
| Polyglyceryl-3 Diisostearate (Lameform TGI) | | 3 | | | | | | 3 |
| Cocoglycerides (Novata ® AB) | | | | | | | 4 | |
| Stearyl alcohol (Lanette ® 18) | | | | 10 | | | | |
| Hydrogenated Castor Oil (Cutina ® HR) | | | | 3.7 | | | 6.5 | |
| Polyglyceryl-2 Dipolyhydroxystearate (Dehymuls ® PGPH) | | 1 | | | | | | |
| PEG-30 Dipolyhydroxystearate (Dehymuls ® LE) | | | | | | | | 1 |
| Cetyl PEG/PPG-10/1 Dimethicone (Degussa) | | | | | | | | 0.5 |
| Sodium Cetearyl Sulfate (Lanette ® E) | 0.3 | | | | | 0.3 | | |
| Pentaerythrityl Distearate (Cutina ® PES) | 1.0 | 2 | 0.7 | 4.7 | 2 | 5 | 3.5 | 2 |
| Behenyl Alcohol (Lanette ® 22) | 2 | | | | | 4 | | |
| Dicaprylyl Carbonate (Cetiol ® CC) | | 7 | | | | | | 7 |
| Dicaprylyl ether (Cetiol ® OE) | 6 | | 5 | 9 | | 6 | 9 | |
| Cocoglycerides (Myritol ® 331) | | | | | | | | |
| Diethylhexylcyclohexane (Cetiol ® S) | | | 5 | 14.7 | | | 35 | |
| Cyclopentasiloxane | 3 | 5 | | 34 | | 3 | 14 | 5 |
| Cyclopentasiloxane and Dimethicone/Vinyldimethicone Crosspolymer SFE 839 (GE Bayer) | | 3 | | | | | | 3 |
| Dimethicone | 1 | | | | | | | |
| Hydrogenated Dimer Dilinoleyl/ Dimethylcarbonate Copolymer (Cosmedia ® DC) | 0.5 | 1 | 1.5 | 1 | 0.5 | 2 | 1 | 1 |
| Triethyl Citrate (Hydagen ® C.A.T) | | | 2 | | | | | |
| PEG-40 Hydrogenated Castor Oil | | | | | 1 | | | |
| Tocopheryl Acetate | | | | 1 | | | | |
| Aluminium Zirconium Tetrachlorohydrex GLY (Rezal 36) | 30 | 40 | | 22.9 | | 30 | 25 | 40 |
| Aluminum Chlorohydrate (Locron L) | | | 10 | | | | | |
| Chitosan (Hydagen ® DCMF) | 0.05 | | | | | | | |
| Glycolic Acid | 0.02 | | | | | | | |
| Glycerin | | 5 | 5 | | | | | 5 |
| Propylene Carbonate (Fluka) | | | | | | | 0.5 | |
| Quaternium-18 Hectorite (Bentone 18) | | | | | | | 1 | |
| Talc (Merck) | | | | | | 5 | 5 | |
| MgSO$_4$ × 7H$_2$O | | 1 | | | | | | 1 |
| Water | | | | Ad 100 | | | | |
| Perfume, Preservatives | q.s. | q.s. | q.s. | q.s. | q.s. | q.s. | q.s. | q.s. |

1—Antiperspirant/Deodorant cream; 2—Antiperspirant cream (W/O); 3—Antiperspirant/Deodorant spray; 4—Antiperspirant stick with Vitamin E; 5—Deodorant wipe formulation; 6—Antiperspirant cream; 7—Antiperspirant "Soft solid" cream; 8—Antiperspirant spray

TABLE 17

O/W sunscreen emulsions

| Component | | | | | | | | | | | |
|---|---|---|---|---|---|---|---|---|---|---|---|
| | 1 | 2 | 3 | 4 | 5 | 6 | 7 | 8 | 9 | 10 | 11 |
| | \multicolumn{11}{c}{C—Cream, L—Emulsion, S—Spray} |
| | L | C | S | L | C | L | L | C | L | C | L |
| Eumulgin ® PRISMA | 0.5 | 1.0 | 0.2 | 0.1 | 1.0 | 0.5 | 0.5 | 2.0 | 0.5 | 0.1 | 0.5 |
| Eumulgin ® Sucro | 2 | 2.5 | 2.5 | 1.0 | 2.5 | 2.5 | 2.5 | 2 | 2.5 | 1.7 | 1.5 |
| Tween ® 60 | | | | 0.2 | | | | | | | |
| Myrj ® 51 | | | | 0.5 | | | | | | | |
| Cutina ® E 24 | | | | 0.1 | | | | | | | |
| Hostaphat ® KL 340 N | | | | | | | | | 0.6 | | |
| Lanette ® E | | | 0.2 | | | | | | | | |
| Amphisol ® K | | | | | | | | | | 1 | |
| Sodium Stearate | | | | | 1 | | | | | | |

TABLE 17-continued

| O/W sunscreen emulsions | | | | | | | | | | | |
|---|---|---|---|---|---|---|---|---|---|---|---|
| Component | 1 | 2 | 3 | 4 | 5 | 6 | 7 | 8 | 9 | 10 | 11 |
| C—Cream, L—Emulsion, S—Spray | L | C | S | L | C | L | L | C | L | C | L |
| Emulgade ® PL 68/50 | | | 1 | | | | | | | | |
| Tego ® Care 450 | | | | | | | | | | 1 | |
| Cutina ® PES | | 0.2 | | | 0.4 | | | | | | |
| Cutina ® MD | 2 | | | 2 | | | 2 | | | 6 | |
| Lanette ® 14 | 1 | | | 1 | | | | 2 | | | 2 |
| Lanette ® O | 1 | 6 | | | 5 | 2 | | 2 | | | |
| Cosmedia ® DC | 1 | 1.5 | | 1 | 1 | | 2 | 2 | | | 2 |
| Antaron ® V 216 | | | 2 | | | 1.5 | | | 1 | 1 | |
| Emery 1780 | | | | | 0.5 | 0.5 | | | | | |
| Lanolin, anhydrous USP | | | | | | | 5 | | | | |
| Myritol ® PC | | | | | 5 | | | | | | |
| Myritol ® 331 | 5 | | 8 | | | 6 | | 10 | | 2 | |
| Finsolv ® TN | | | 1 | | | | | 1 | 8 | | |
| Cetiol ® CC | | 2 | 5 | | | 4 | 4 | 2 | | 2 | |
| Cetiol ® OE | | | 3 | | | | | | 2 | 3 | |
| Dow Corning DC ® 244 | 4 | | 1 | | 5 | | | 2 | | | 2 |
| Dow Corning DC ® 2502 | | 1 | | | 2 | | | | | | |
| Squatol ® S | | | | | | | 4 | | | | |
| Wacker AK ® 350 Silicone Oil | | 2 | | | | | | | | | |
| Cetiol ® 868 | | | | | 2 | | 4 | | | | 7 |
| Cetiol ® J 600 | | | | | 3 | 2 | | | | 5 | |
| Mineral Oil | | | 9 | | | | | | | | |
| Cetiol ® B | | | 1 | | | | | | | 2 | |
| Eutanol ® G | | | | | 2 | | | | 4 | | |
| Eutanol ® G 16 | 4 | | | | | 4 | | | | | |
| Cetiol ® PGL | | 5 | | | | | | | | 5 | |
| Almond Oil | | | 2 | | | | | 1 | | | |
| Photonyl ® LS | | | | | 2 | | | | | 2 | |
| Panthenol | | | | | | | 1 | | | | |
| Bisabolol | | | | | | | 0.2 | | | | |
| Tocopherol/Tocopheryl Acetate | | | | | | | 1 | | | | |
| Photonyl ® LS | | | | | | | | | | | |
| Neo Heliopan ® AP (Na-salt) | | 1 | | | | | | | 1 | | |
| Neo Heliopan ® Hydro (Na-salt) | 2 | | 2.2 | | | | | | 1 | | |
| Neo Heliopan ® 303 | 3 | 5 | 9 | 4 | | | | | | | |
| Neo Heliopan ® BB | | | | | 1 | | | | | | 2 |
| Neo Heliopan ® MBC | 2 | | 3 | | | 2 | 2 | 2 | | | 1 |
| Neo Heliopan ® OS | | | | | | | | 10 | 7 | | |
| Neo Heliopan ® E 1000 | | 7.5 | | 6 | | | | | | | 6 |
| Neo Heliopan ® AV | | | 7.5 | | | 7.5 | 4 | 5 | | | |
| Uvinul ® A PLUS | | | | 2 | 1 | | | | | | |
| Uvinul ® T 150 | 2 | | | | 2.5 | | | 1 | | | |
| Tinosorb ® M | | | 3 | | | | 2 | | | | 3 |
| Tinosorb ® S | | | 1 | | | | 1.5 | | | | |
| Uvasorb ® HEB | | 1 | | | 1 | | | | | | |
| Parsol ® 1789 | | 1 | 1 | | | | 2 | | 2 | 2 | |
| Zincoxide NDM | 10 | | 5 | | | 10 | | 3 | | 5 | 4 |
| Eusolex ® T 2000 | | | | | 5 | | 3 | 3 | | | 4 |
| Veegum ® Ultra | 1.5 | | 0.75 | | | | | 1 | 1 | | |
| Keltrol ® T | 0.5 | | 0.25 | | | | | 0.5 | 0.5 | | |
| Cosmedia ® SP | | 0.5 | | | 0.5 | | 0.2 | 0.2 | | 0.2 | 0.2 |
| Carbopol ® 980 | | | | 0.2 | | 0.2 | | | 0.1 | 0.3 | 0.2 |
| Ethanol | | | | | | | | | 10 | | |
| Butylene glycol | | 2 | | 4 | 3 | | 2 | 5 | 2 | | 2 |
| Glycerin | 5 | 5 | 5 | | 3 | 3 | 2 | | 4 | | 3 |
| Preservative, NaOH, Water | | | | | q.s. ad 100 | | | | | | |

TABLE 18

| | O/W sunscreen emulsions | | | | | | | | | | |
|---|---|---|---|---|---|---|---|---|---|---|---|
| | Component | | | | | | | | | | |
| | 12 | 13 | 14 | 15 | 16 | 17 | 18 | 19 | 20 | 21 | 22 |
| | L = Emulsion, C = Cream | | | | | | | | | | |
| | L | C | L | C | L | C | S | C | C | L | L |
| Eumulgin ® SG | 0.4 | 1.0 | 0.3 | 1.5 | 0.6 | 1.2 | 0.3 | 0.6 | 2.0 | 0.4 | 0.4 |
| Emulgade ® Sucro | 2 | 1.8 | 2.5 | 1.5 | 1 | 2 | 2.5 | 3 | 2 | 1.5 | 1.5 |
| Cutina ® E 24 | | | | 0.5 | | | | | | | |
| Lanette ® E | | | | | | | 0.1 | | | | |
| Amphisol ® K | 0.5 | | | | | | 1 | | | | |
| Sodium stearate | | | | | 1 | | | | | | |
| Emulgade ® PL 68/50 | | 1.5 | | | | | | | | | |
| Tego ® Care 450 | | | | | | | | | 0.3 | | |
| Cutina ® PES | | 1 | | | 0.5 | | | 0.5 | | | |
| Cutina ® MD | 1 | | | 4 | 1 | 3 | | | | | 1 |
| Lanette ® 14 | | 2 | | | | | | | | 1 | |
| Lanette ® O | | | 2 | | | | | 2 | 1 | 1 | |
| Allianz ® OPT | 1 | | | 1 | 1 | | | 2 | | | 2 |
| Cosmedia ® DC | | 1.5 | 2 | | | 1.5 | 2 | | 1.5 | 1.5 | |
| Emery ® 1780 | | | | 1 | 1 | | | | | | |
| Lanolin, anhydrous, USP | | | | | | 1 | 1 | | | | |
| Myritol ® PC | | | | | | | | | 5 | | |
| Myritol ® 331 | 12 | | 12 | | | 8 | 8 | | | 10 | 8 |
| Finsolv ® TN | | | | | 5 | | | 3 | 3 | | |
| Cetiol ® CC | 6 | | 6 | | | 5 | 5 | | | | |
| Cetiol ® OE | | | | | 2 | | | | | | 2 |
| Dow Corning DC ® 244 | | 2 | | | 1 | | | | | | |
| Dow Corning DC ® 2502 | | 1 | | | 1 | | | 3 | | | |
| Ceraphyl ® 45 | | | | | | | | | | 2 | 2 |
| Wacker AK ® 350 silicone oil | | | | | 1 | | | | | | |
| Cetiol ® 868 | | 2 | | | | | | | | | |
| Cetiol ® J 600 | | 2 | | | | | | | | | |
| Mineral oil | | | | 10 | | | | | | | |
| Cetiol ® B | 4 | | 4 | | | | | 4 | | | |
| Eutanol ® G | | 3 | | | | 3 | | | | | |
| Eutanol ® G 16 S | 10 | | | | | | | | | | |
| Cetiol ® PGL | | | | | | | | | 2 | | |
| Photonyl ® LS | | | | | | | | | | 2 | |
| Panthenol | | | | | | 1 | | | | | |
| Bisabolol | | | | | | 0.2 | | | | | |
| Tocopherol/Tocopheryl acetate | | | | | | 1 | | | | | |
| Neo Heliopan ® Hydro (Na salt) | | | | | | | | | | 3 | |
| Eusolex ® OCR | 6 | | 9 | | 5 | 7 | 9 | | 4 | | 7 |
| Neo Heliopan ® AP (Na salt) | | | | 0.5 | | 1 | | | | | |
| Neo Heliopan ® BB | | | | | | | | 1 | 1 | | 1 |
| Neo Heliopan ® MBC | | 2 | | 1 | | | | 3 | 1 | | 3 |
| Neo Heliopan ® OS | 2 | | | | | | | | 7 | | |
| Neo Heliopan ® E1000 | | 4 | | | | | | 5 | | | |
| Neo Heliopan ® AV | | 4 | 7.5 | 5 | | | | 5 | 4 | 7.5 | |
| Uvinul ® A PLUS | | | | | | 1 | | 2 | | | |
| Uvinul ® T 150 | 1 | | | | | | | | 1.3 | 1 | 1 |
| Tinosorb ® M | | | 6.5 | | | | | | | 4 | |
| Tinosorb ® S | | | | 1 | | 2 | | | | | |
| Uvasorb ® HEB | 1 | | | | | | | | | | 2 |
| Parsol ® 1789 | 1 | | | | | | | | 2 | | 1 |
| Z-Cote ® HP 1 | 7 | 2 | 5 | | | 7 | 5 | | 6 | 2 | |
| Eusolex ® T 2000 | 5 | 2 | | | 10 | | 10 | | | 2 | |
| Veegum ® Ultra | 1.5 | | 1.5 | | | 1.5 | 1.2 | | 1 | | |
| Keltrol ® T | 0.5 | | 0.5 | | | 0.5 | 0.4 | | 0.5 | | |
| Cosmedia ® SP | | | 0.2 | 0.3 | | | 0.1 | | | 0.2 | |
| Pemulen ® TR 2 | | 0.3 | | 0.3 | | | | | 0.2 | | 0.3 |
| Ethanol | | 5 | | 8 | | | | | | | |
| Butylene glycol | 1 | | | 3 | 3 | | | | | 8 | 1 |
| Glycerin | 2 | 4 | 3 | 3 | | 3 | 3 | 3 | 5 | | 3 |
| Water/Preservative /NaOH | | | | | ad 100/q.s./q.s | | | | | | |

TABLE 19

| | W/O sunscreen emulsions | | | | | | | | | | |
|---|---|---|---|---|---|---|---|---|---|---|---|
| | Component | | | | | | | | | | |
| | 23 | 24 | 25 | 26 | 27 | 28 | 29 | 30 | 31 | 32 | 34 |
| | C—Cream, L—Lotion | | | | | | | | | | |
| | C | L | C | L | C | L | L | L | L | C | C |
| Eumulgin ® SG | 0.05 | 0.1 | 0.2 | 0.1 | 0.2 | 0.1 | 0.3 | 0.1 | 0.1 | 0.1 | 0.2 |
| Emulgade ® Sucro | 0.2 | 0.4 | 0.3 | 0.2 | 0.5 | 0.1 | 0.4 | 0.5 | 0.2 | 0.3 | 0.4 |
| Dehymuls ® PGPH | 4 | 2 | 1 | 3 | 3 | 1 | 1 | 2 | | 4 | 1 |
| Dehymuls ® LE | | | | | | | | | 2 | | |
| Monomuls ® 90-O18 | | | 2 | | | | | | | | |
| Lameform ® TGI | 2 | | 4 | | 3 | | | | | 1 | 3 |
| Abil ® EM 90 | | | | | | | 4 | | | | |
| Isolan ® PDI | | | | | | 4 | | 2 | 2 | | |
| Zinc Stearate | 1 | | | 1 | 1 | | | 1 | 1 | 1 | |
| Beeswax | 1 | | 5 | 1 | | | | 5 | 5 | 7 | 5 |
| Tego ® Care CG | | | | | 1 | | | | | | 0.5 |
| Cutina ® PES | 2 | 3 | 2 | 1 | 2 | | 1 | 1 | 1 | 1 | 4 |
| Prisorine ® 3505 | | | 1 | | | | 1 | 1 | | | 1 |
| Cosmedia ® DC | 3 | 4 | 2 | 1 | 1 | 2 | 2 | 2 | 2 | 1 | 1 |
| Myritol ® 331 | 2 | | | | 3 | 6 | | | | | 8 |
| Finsolv ® TN | | | | 5 | | | 5 | | | | |
| Cetiol ® CC | 10 | 4 | 2 | | 4 | 2 | | | | 3 | 5 |
| Tegosoft DEC | | 4 | | 3 | 2 | | 5 | 5 | 5 | 3 | |
| Cetiol ® OE | | | | | 4 | | 5 | | | 2 | |
| Dow Corning ® DC 244 | | | 3 | | | | 2 | | | 4 | |
| Dow Corning ® DC 2502 | 1 | | 1 | | 2 | 1 | | | | | 1 |
| Wacker AK 350 silicone oil | | 1 | | 4 | | | | 3 | 3 | | |
| Cetiol ® PGL | | 3 | | | | 4 | | | | | |
| Copherol ® F 1300 | | | | | | 1 | | | | | |
| Magnesium sulfate × 7 Water | | | | | | 1 | | | | | |
| Neo Heliopan ® Hydro (Na salt) | 2 | | 2.2 | | 3 | 3 | | | | | 2 |
| Neo Heliopan ® 303 | | 5 | | | | | | | | | 4 |
| Uvasorb ® HEB | 1 | | | 1 | 1 | | | | | | 2 |
| Neo Heliopan ® MBC | 2 | | | | | 2 | 2 | 2 | 2 | | |
| Uvinul ® A plus | | | | | 2 | | | | | 3 | |
| Neo Heliopan ® AP (Na salt) | | 2 | 2 | | 1 | | | | | | 6 |
| Neo Heliopan ® AV | 3 | | 4 | 6 | 4 | 7.5 | 4 | 5 | 5 | | 1 |
| Uvinul ® T 150 | 1 | 1 | | | 2.5 | | | 1 | 1 | | |
| Parsol ® 1789 | 2 | 1 | | | | | 2 | | | 2 | |
| Zinc oxide NDM | | | | | | 10 | | 3 | | | 4 |
| Tinosorb ® M | | 3 | | 3 | | | | 2 | 2 | 2 | |
| Tinosorb ® S | | 3 | | 3 | | | | 2 | 2 | 2 | |
| Eusolex ® T Agua | | | 8 | | | | | 5 | | | |
| Eusolex ® T 2000 | | | | | 5 | | 3 | 3 | 3 | | 4 |
| Ethanol | | | | | | | | | | 8 | |
| Glycerin | 5 | 3 | 3 | 3 | 5 | 3 | 2 | 3 | 3 | 4 | 3 |
| Water ad 100, Preservative q.s. | | | | | | | | | | | |

| Sporty Looking Face Cream | | | | |
|---|---|---|---|---|
| Phase | Component | | % | Function |
| I. | EUMULGIN ® PRISMA | Disodium Cetearyl Sulfosuccinate | 0.10 | Emulsifier (W/O) |
| | ULTRAGEL ™ 300 | Polyquaternium-37 (EU 2006/257/EC) Polyquaternium-37 (CTFA) | 0.90 | Polymer, cationic |
| | CUTINA ® PES | Pentaerythrityl Distearate | 2.00 | Consistency factor |
| | CUTINA ® MD | Glyceryl Stearate | 2.00 | Consistency factor |
| | CETIOL ® CC | Dicaprylyl Carbonate | 2.00 | Emollient |
| | CETIOL ® SENSOFT | Propylheptyl Caprylate | 2.00 | Emollient |
| | COPHEROL ® F 1300 C | Tocopherol | 0.50 | Active ingredient |
| | Eusolex OCR (Merck) | Octocrylene | 2.00 | UV filter, UV-B |
| | Parsol 1789 (DSM Nutritional Products, Inc.) | Butyl Methoxydibenzoylmethane | 0.60 | UV filter, UV-A |
| II. | Water, demin. | Aqua | 72.70 | |
| | Glycerin | Glycerin | 5.00 | Active, moisturizing |
| III. | Dihydroxyacetone | Dihydroxyacetone | 1.50 | Active ingredient |
| | Water, demin. | Aqua | 5.00 | |

Sporty Looking Face Cream

| Phase | Component | | % | Function |
|---|---|---|---|---|
| IV. | Ethanol (denatured) | Ethanol | 3.00 | Active, cooling |
| | HERBALIA ® GINKGO CG | Ginkgo Biloba Extract (EU); Ginkgo Biloba Leaf Extract (US) | 0.20 | Active ingredient |
| | Tapioca Starch (National Starch) | Tapioca Starch | 0.5 | Skin feel modifier |
| | Preservative | Preservative | q.s. | |
| | Perfume | Perfume | q.s. | | pH value (as is) 4.0
Viscosity (Brookfield RVF, 23° C., spindle TE; 4 rpm, Helipath) 50 000 mPas

Self-tanning après lotion

| Phase | Component | | % | Function |
|---|---|---|---|---|
| I. | EUMULGIN ® PRISMA | Disodium Cetearyl Sulfosuccinate | 0.08 | Emulsifier (O/W) |
| | ULTRAGEL ® 300 | Polyquaternium-37 | 0.75 | Polymer, cationic |
| | CUTINA ® PES | Pentaerythrityl Distearate | 2.00 | Consistency factor |
| | CUTINA ® MD | Glyceryl Stearate | 2.00 | Consistency factor |
| | CETIOL ® SB 45 | Butyrospermum Parkii (Shea Butter) | 1.50 | Emollient |
| | CETIOL ® CC | Dicaprylyl Carbonate | 2.00 | Emollient |
| | CETIOL ® 868 | Ethylhexyl Stearate | 1.00 | Emollient |
| | CETIOL ® SenSoft | Propylheptyl Caprylate (proposed) | 2.00 | Emollient |
| II. | Glycerin | Glycerin | 5.00 | Active, moisturizing |
| | Water, demin. | Aqua | 70.67 | |
| III. | Water, demin. | Aqua | 5.00 | |
| | Dihydroxyacetone (Merck) | Dihydroxyacetone | 1.50 | Active ingredient |
| IV. | Ethanol (denatured) | Ethanol | 5.00 | Active, cooling |
| | ALOVERIA ® | Aloe Barbadensis (EU); Aloe Barbadensis Leaf Extract (US) | 1.00 | Active ingredient |
| | Tapioca Starch (National Starch) | Tapioca Starch | 0.50 | Active ingredient |
| | Preservative | Preservative | q.s. | |
| | Perfume | Perfume | q.s. | |

Viscosity (Brookfield RVF, 23° C., spindle 5, 10 rpm) 12 400 mPas
pH value (as is) 4.0

Self-tanning body lotion

| Phase | Component | | % | Function |
|---|---|---|---|---|
| I. | EUMULGIN ® PRISMA | Disodium Cetearyl Sulfosuccinate | 0.08 | Emulsifier (W/O) |
| | ULTRAGEL ® 300 | Polyquaternium-37 | 0.70 | Polymer, cationic |
| | CUTINA ® PES | Pentaerythrityl Distearate | 2.00 | Consistency factor |
| | CUTINA ® MD | Glyceryl Stearate | 2.00 | Consistency factor |
| | MYRITOL ® 331 | Cocoglycerides | 3.00 | Emollient |
| | CETIOL ® CC | Dicaprylyl Carbonate | 3.00 | Emollient |
| | COPHEROL ® F 1300 C | Tocopherol | 0.50 | Active ingredient |
| II. | Glycerin | Glycerin | 5.00 | Active, moisturizing |
| | Water, demin. | Aqua | 75.02 | |
| III. | Dihydroxyacetone (Merck) | Dihydroxyacetone | 3.00 | Active ingredient |
| | Water, demin. | Aqua | 5.00 | |
| IV. | Tapioca Starch (National Starch) | Tapioca Starch | 0.50 | Active ingredient |
| | PLANTACTIV ® CENTELLA | Asiaticoside (and) Asiatic Acid (and) Madecassic Acid | 0.20 | Active ingredient |
| | Preservative | Preservative | q.s. | |
| | Perfume | Perfume | q.s. | |

Viscosity (Brookfield RVF, 23° C., spindle 5, 10 rpm) 14 000 mPas
pH value (as is) 3.9

Cosmetic formulations:

| | 1 | 2 | 3 | 4 | 5 | 6 | 7 |
|---|---|---|---|---|---|---|---|
| Eumulgin ® Prisma | 0.25 | 0.25 | 0.25 | 0.25 | 0.25 | 0.25 | 0.25 |
| Cetiol ® SenSoft | 4.00 | 4.00 | 4.00 | 4.00 | 4.00 | 3.00 | 4.00 |
| Cetiol ® LC | 5.00 | 5.00 | 5.00 | 5.00 | 5.00 | 3.00 | 4.00 |
| Myritol ® 331 | 5.00 | 5.00 | 5.00 | 5.00 | 5.00 | 5.00 | 5.00 |
| Cegesoft ® PS 6 | | 5.00 | 5.00 | 5.00 | 5.00 | 5.00 | 3.00 |
| Zinc Oxide NDM | | 5.00 | 5.00 | 5.00 | 5.00 | 5.00 | |
| Copherol ® 1250 | 0.50 | 0.50 | 0.50 | 0.50 | 0.50 | 0.50 | 0.50 |
| Cutina ® PES | | | 3.00 | 3.00 | 3.00 | 3.00 | 3.00 |
| Cegesoft ® SBE | | | | | | 2.00 | 2.00 |
| Eusolex ® OCR | | | | | | | 10.00 |
| Parsol ® 1789 | | | | | | | 5.00 |
| Parsol ® SLX | | | | | | | 3.00 |
| Eusolex ® T-AVO | | | | | | | 8.00 |
| Glycerin 99.5% | 5.00 | 5.00 | 5.00 | 5.00 | 5.00 | 5.00 | 5.00 |
| Water | 57.15 | 40.15 | 44.15 | 45.15 | 44.65 | 45.65 | 35.65 |
| Rheocare ® TTN | 2.00 | 4.00 | 2.00 | 1.00 | 1.50 | 1.50 | 0.50 |
| Neo Heliopan ® Hydro (15%) | 10.00 | 10.00 | 10.00 | 10.00 | 10.00 | 10.00 | 5.00 |
| Neo Heliopan ® AP (15%) | 10.00 | 10.00 | 10.00 | 10.00 | 10.00 | 10.00 | 5.00 |
| Phenonip ® XB | 1.00 | 1.00 | 1.00 | 1.00 | 1.00 | 1.00 | 1.00 |
| Euxyl ® K 100 | 0.10 | 0.10 | 0.10 | 0.10 | 0.10 | 0.10 | 0.10 |
| Ethanol | | 5.00 | | | | | |
| NaOH (50%) | q.s. | q.s. | q.s. | q.s. | q.s. | q.s. | q.s. |
| pH | 7.2 | 8.1 | 8.1 | 7.5 | 8.4 | 8.0 | 6.9 |
| Viscosity (Brookfield, RVF, 23° C., spindle TE with helipath, 4 rpm) | | | 362500 | | 362500 | 162500 | 162500 |
| Viscosity (Brookfield, RVF, 23° C., spindle 5, 10 rpm) | 6000 | 12000 | | 5200 | | | |

Cosmetic formulations:

| | 8 | 9 | 10 | 11 | 12 | 13 | 14 |
|---|---|---|---|---|---|---|---|
| Eumulgin ® Prisma | 0.25 | 0.25 | 0.25 | 0.25 | 0.25 | 0.25 | 0.25 |
| Cetiol ® SenSoft | 4.00 | 4.00 | 4.00 | 4.00 | 4.00 | 3.00 | 4.00 |
| Cetiol ® LC | 5.00 | 5.00 | 5.00 | 5.00 | 5.00 | 3.00 | 4.00 |
| Myritol ® 331 | 5.00 | 5.00 | 5.00 | 5.00 | 5.00 | 5.00 | 5.00 |
| Cegesoft ® PS 6 | | 5.00 | 5.00 | 5.00 | 5.00 | 5.00 | 3.00 |
| Zinc Oxide NDM | | 5.00 | 5.00 | 5.00 | 5.00 | 5.00 | |
| Copherol ® 1250 | 0.50 | 0.50 | 0.50 | 0.50 | 0.50 | 0.50 | 0.50 |
| Cutina ® PES | | | 3.00 | 3.00 | 3.00 | 3.00 | 3.00 |
| Cegesoft ® SBE | | | | | | 2.00 | 2.00 |
| Eusolex ® OCR | | | | | | | 10.00 |
| Parsol ® 1789 | | | | | | | 5.00 |
| Parsol ® SLX | | | | | | | 3.00 |
| Eusolex ® T-AVO | | | | | | | 8.00 |
| Glycerin 99.5% | 5.00 | 5.00 | 5.00 | 5.00 | 5.00 | 5.00 | 5.00 |
| Water | 57.15 | 40.15 | 42.15 | 44.15 | 43.65 | 44.65 | 34.65 |
| Rheocare ® TTN | 2.00 | 4.00 | 4.00 | 2.00 | 2.50 | 2.50 | 1.50 |
| Neo Heliopan ® Hydro (15%) | 10.00 | 10.00 | 10.00 | 10.00 | 10.00 | 10.00 | 5.00 |
| Neo Heliopan ® AP (15%) | 10.00 | 10.00 | 10.00 | 10.00 | 10.00 | 10.00 | 5.00 |
| Phenonip ® XB | 1.00 | 1.00 | 1.00 | 1.00 | 1.00 | 1.00 | 1.00 |
| Euxyl ® K 100 | 0.10 | 0.10 | 0.10 | 0.10 | 0.10 | 0.10 | 0.10 |
| Ethanol | | 5.00 | | | | | |
| NaOH (50%) | q.s. | q.s. | q.s. | q.s. | q.s. | q.s. | q.s. |
| pH | 7.2 | 8.2 | 8.2 | 7.6 | 8.3 | 8.4 | 6.8 |
| Viscosity (Brookfield, RVF, 23° C., spindle TE with helipath, 4 rpm) | | | 362500 | | 300000 | 162500 | 287500 |
| Viscosity (Brookfield, RVF, 23° C., spindle 5, 10 rpm) | 3200 | 6000 | | 5200 | | | |

Cosmetic formulations:

| | 15 | 16 | 17 | 18 | 19 | 20 | 21 |
|---|---|---|---|---|---|---|---|
| Eumulgin ® Prisma | 0.25 | 0.25 | 0.25 | 0.25 | 0.25 | 0.25 | 0.25 |
| Cetiol ® SenSoft | 4.00 | 4.00 | 4.00 | 4.00 | 4.00 | 3.00 | 4.00 |
| Cetiol ® LC | 5.00 | 5.00 | 5.00 | 5.00 | 5.00 | 3.00 | 4.00 |
| Myritol ® 331 | 5.00 | 5.00 | 5.00 | 5.00 | 5.00 | 5.00 | 5.00 |

-continued

Cosmetic formulations:

| | 15 | 16 | 17 | 18 | 19 | 20 | 21 |
|---|---|---|---|---|---|---|---|
| Cegesoft ® PS 6 | | 5.00 | 5.00 | 5.00 | 5.00 | 5.00 | 3.00 |
| Zinc Oxide NDM | | 5.00 | 5.00 | 5.00 | 5.00 | 5.00 | |
| Copherol ® 1250 | 0.50 | 0.50 | 0.50 | 0.50 | 0.50 | 0.50 | 0.50 |
| Cutina ® PES | | | 3.00 | 3.00 | 3.00 | 3.00 | 3.00 |
| Cegesoft ® SBE | | | | | | 2.00 | 2.00 |
| Eusolex ® OCR | | | | | | | 10.00 |
| Parsol ® 1789 | | | | | | | 5.00 |
| Parsol ® SLX | | | | | | | 3.00 |
| Eusolex ® T-AVO | | | | | | | 8.00 |
| Glycerin 99.5% | 5.00 | 5.00 | 5.00 | 5.00 | 5.00 | 5.00 | 5.00 |
| Water | 57.15 | 40.15 | 42.15 | 44.15 | 43.65 | 44.65 | 34.65 |
| Rheocare ® TTN | 2.00 | 4.00 | 4.00 | 2.00 | 2.50 | 2.50 | 1.50 |
| Neo Heliopan ® Hydro (15%) | 10.00 | 10.00 | 10.00 | 10.00 | 10.00 | 10.00 | 5.00 |
| Neo Heliopan ® AP (15%) | 10.00 | 10.00 | 10.00 | 10.00 | 10.00 | 10.00 | 5.00 |
| Phenonip ® XB | 1.00 | 1.00 | 1.00 | 1.00 | 1.00 | 1.00 | 1.00 |
| Euxyl ® K 100 | 0.10 | 0.10 | 0.10 | 0.10 | 0.10 | 0.10 | 0.10 |
| Ethanol | | 5.00 | | | | | |
| NaOH (50%) | q.s. | q.s. | q.s. | q.s. | q.s. | q.s. | q.s. |
| pH | 7.2 | 7.5 | 7.7 | 7.6 | 8.0 | 7.9 | 6.8 |
| Viscosity (Brookfield, RVF, 23° C., spindle TE with helipath, 4 rpm) | | | 162500 | | 162500 | 150000 | 150000 |
| Viscosity (Brookfield, RVF, 23° C., spindle 5, 10 rpm) | 1800 | 3000 | | 3000 | | | |

APPENDIX—INGREDIENTS: TRADE NAME AND INCI NAME

AMP-95, INCI: Aminomethyl Propanol, Dow Chemical Co; Abil® EM 90, INCI: Cetyl Dimethicone Copolyol, Tego Cosmetics (Goldschmidt); Allianz® OPT, INCI: Acrylates/C12-22 Alkyl Methacrylate Copolymer, Rohm and Haas; Amphisol® K, INCI: Potassium Cetyl Phosphate, Hoffmann La Roche; Admul® WOL 1403, INCI: Polyricinoleate of polyglycerol, Quest; Antaron® V 220, INCI: PVP/Eicosene Copolymer, GAF General Aniline Firm Corp. (IPS-Global); Antaron® V 216, INCI: PVP/Hexadecene Copolymer, GAF General Aniline Firm Corp. (IPS-Global); Arlacel® 83, INCI: Sorbitan Sesquioleate, Uniqema (ICI Surfactants); Arlacel® P 135, INCI: PEG-30 Dipolyhydroxystearate, Uniqema (ICI Surfactants); Carbopol® 980, INCI: Carbomer, Goodrich; Carbopol® 2984, INCI: Carbomer, Noveon, Inc.; Carbopol® ETD 2001, INCI: Carbomer, Noveon, Inc.; Carbopol® Ultrez 10, INCI: Carbomer, Noveon, Inc.; Cegesoft® C17, Myristyl Lactate, Cognis GmbH; Cegesoft® PFO, INCI: Passiflora Incarnata (EU), Cognis GmbH; Cegesoft® PS 6, INCI: Olus, Cognis GmbH; Cegesoft® SH, INCI: Shorea Stenoptera Seed Butter, Cognis GmbH; Ceraphyl® 45, INCI: Diethylhexyl Malate, International Specialty Products; Cetiol® 868, INCI: Ethylhexyl Stearate, Manufacturer: Cognis GmbH; Cetiol® A, INCI: Hexyl Laurate, Cognis GmbH; Cetiol® B, INCI: Dibutyl Adipate, Cognis GmbH; Cetiol® CC, INCI: Dicaprylyl Carbonate, Cognis GmbH; Cetiol® J 600, INCI: Oleyl Erucate, Cognis GmbH; Cetiol® LC, INCI: Coco-Caprylate/Caprate, Cognis GmbH; Cetiol® MM, INCI: Myristyl Myristate, Cognis GmbH; Cetiol® OE, INCI: Dicaprylyl Ether, Cognis GmbH; Cetiol® PGL, INCI: Hexyldecanol, Hexyldecyl Laurate, Cognis GmbH; Cetiol® S, INCI: Diethylhexylcyclohexane, Cognis GmbH; Cetiol® SB 45, INCI: Shea Butter Butyrospermum Parkii (Linne), Cognis GmbH; Cetiol® SN, INCI: Cetearyl Isononanoate, Cognis GmbH; Cetiol®Sensoft INCI: Propylheptyl Caprylate; Copherol® F 1300 C, INCI: Tocopherol, Cognis GmbH; Copherol 1250 C, INCI: Tocopheryl Acetate, Cognis GmbH; Cosmedia® DC, INCI: Hydrogenated Dimer Dilinoleyl/Dimethylcarbonate Copolymer, Cognis GmbH; Cosmedia® SP, INCI: Sodium Polyacrylate, Cognis GmbH; Crodesta® F-50, INCI: Sucrosedistearate, Croda; Cutina® E 24, INCI: PEG-20 Glyceryl Stearate, Cognis GmbH; Cutina® HR, INCI: Hydrogenated Castor Oil, Cognis GmbH; Cutina® MD, INCI: Glyceryl Stearate, Cognis GmbH; Cutina® PES, INCI: Pentaerythrityl Distearate, Cognis GmbH; Cutina® FS-45, INCI: Palmitic Acid, Stearic Acid, Cognis GmbH; Cutina® GMS-SE, INCI: Glyceryl Stearate SE, Cognis GmbH; Cutina® LM conc, INCI: Polyglyceryl-2 Dipolyhydroxystearate, Octyldodecanol, Copernicia Cerifera (Carnauba) Wax, Euphorbia Cerifera (Candelilla) Wax, Beeswax, Cetearyl Glucoside, Cetearyl Alcohol, Cognis GmbH; Dehymuls® FCE, INCI: Dicocoyl Pentaerythrityl Distearyl Citrate, Cognis GmbH; Dehymuls® HRE 7, INCI: PEG-7 Hydrogenated Castor Oil, Cognis GmbH; Dehymuls® PGPH, INCI: Polyglyceryl-2 Dipolyhydroxystearate, Cognis GmbH; Dehymuls® LE, INCI: PEG-30 Dipolyhydroxystearate, Cognis GmbH; Dow Corning® 244 Fluid, INCI: Cyclomethicone, Dow Corning; Dow Corning® 1503 Fluid, INCI: Dimethicone and Dimethiconol, Dow Corning; Dow Corning® 246 Fluid, Cyclopentasiloxane, Dow Corning; Dow Corning® 2502, INCI: Cetyl Dimethicone, Dow Corning; Dow Corning DC® 245 INCI: Cyclopentasiloxane, Dow Corning; Dehyquart® C 4046, INCI: Cetearyl Alcohol, Dipalmitoylethyl Hydroxyethylammonium Methosulfate, Ceteareth-20, Cognis GmbH; Dry®Flo Plus, INCI: Aluminum Starch Octenylsuccinate, National Starch; Dry®Flo PC, INCI: Aluminum Starch Octenylsuccinate, Akzo Nobel; Elfacos®ST 37, INCI: PEG-22 Dodecyl Glycol Copolymer, Akzo-Nobel; Elfacos®ST 9, INCI: PEG-45 Dodecyl Glycol Copolymer, Akzo-Nobel; Emery® 1780, INCI: Lanolin Alcohol, Cognis Corp.; Emulgade® CM, INCI: Cetearyl Isononanoate and Ceteareth-20 and Cetearyl Alcohol and Glyceryl Stearate and Glycerin and Ceteareth-12 and Cetyl Palmitate, Cognis GmbH; Emulgade®PL 68/50, INCI: Cetearyl Glucoside, Cetearyl Alcohol, Cognis GmbH; Emulgade® SE-PF, INCI: Glyceryl Stearate (and) Ceteareth-20 (and) Ceteareth-12

(and) Cetearyl Alcohol (and) Cetyl Palmitate, Cognis GmbH; Emulgade®SUCRO, INCI: Sucrose Polystearate (and) Hydrogenated Polyisobutene, Cognis GmbH; Eumulgin®B1, INCI: Ceteareth-12, Cognis GmbH; Eumulgin® B 2, INCI: Ceteareth-20, Cognis GmbH; Eumulgin®HRE 40, INCI: PEG-40 Hydrogenated Castor Oil, Cognis GmbH; Eumulgin® Prisma INCI: Disodium Cetearyl Sulfosuccinate; Eumulgin®SG, INCI: Sodium Stearoyl Glutamate, Cognis GmbH; Eumulgin® VL 75, INCI: Lauryl Glucoside (and) Polyglyceryl-2 Dipolyhydroxystearate (and) Glycerin, Cognis GmbH; Eusolex® OCR, INCI: Octocrylene, Merck; Eusolex® 2292, INCI: Ethylhexyl Methoxycinnamate and BHT, Merck; Eusolex®T-AVO, INCI: Titanium Dioxide (and) Silica, Merck; Eusolex® T 2000, INCI: Titanium Dioxide, Alumina, Simethicone, Merck; Eusolex® AQUA, INCI: Water and Titanium Dioxide and Alumina and Sodium Metaphosphate and Phenoxyethanol and Sodium Methylparaben, Merck; Eutanol®G, INCI: Octyldodecanol, Cognis GmbH; Eutanol®G 16, INCI: Hexyldecanol, Cognis GmbH; Eutanol®G 16 S, INCI: Hexyldecyl Stearate, Cognis GmbH; Euxyl® K100: INCI: Benzyl Alcohol and Methylchloroisothiazolinone and Methylisothiazolinone; Finsolv® TN, INCI: C 12/15 Alkyl Benzoate, Findex (Nordmann/Rassmann); Fitoderm®, INCI: Squalane, Cognis GmbH; Generol® R, INCI: Brassica Campestris (Rapeseed) Sterols, Cognis GmbH; Glucate®DO, INCI: Methyl Glucose Dioleate, NRD Nordmann/Rassmann; Hispagel® 200, INCI: Glycerin, Glyceryl Polyacrylate, Cognis GmbH; Hostaphat® KL 340 N, INCI: Trilaureth-4 Phosphate, Clariant; Hydagen® C.A.T., INCI: Triethyl Citrate, Cognis GmbH; Hydagen®CMF, INCI: Chitosan Glycolate, Cognis GmbH; Hydagen®DCMF, INCI: Chitosan, Cognis GmbH; Imwitor® 372 P, INCI: Glyceryl Stearate Citrate; Insect Repellent®3535, INCI: Ethyl Butylacetylaminopropionate, EMD Chemicals Inc; Isolan®PDI, INCI: Diisostearoyl Polyglyceryl-3 Diisostearate, Goldschmidt AG; Isolan® GPS, INCI: Polyglyceryl-4 Diisostearate/Polyhydroxystearate/Sebacate, Evonik Goldschmidt; Isolan® GI 34, INCI: Polyglyceryl-4 Isostearate, Evonik Goldschmidt; Irwinol® LS 9319, INCI: Octyldecanol, Irvingia Gabonensis Kernel Butter, Hydrogenated Coco-Glycerides; Keltrol®, INCI: Xanthan Gum, CP Kelco; Lameform®TGI, INCI: Polyglyceryl-3 Diisostearate, Cognis GmbH; Lanette®14, INCI: Myristyl Alcohol, Cognis GmbH; Lanette®18, INCI: Stearyl Alcohol, Cognis GmbH; Lanette®22, INCI: Behenyl Alcohol, Cognis GmbH; Lanette®E, INCI: Sodium Cetearyl Sulfate, Cognis GmbH; Lanette0, INCI: Cetearyl Alcohol, Cognis GmbH; Locron® L, INCI: Aluminum Chlorohydrate, Clariant; Lucentite® SAN, INCI: Quaternium-18 Hectorit, Co-Op Chemical Co. Ltd.; Microna® Matte White (INCI: Titanium Dioxide, Zinc Oxide); Microna® Matte Black (INCI: Iron Oxide; Mica); Microna® Matte Yellow (INCI: Iron Oxide; Mica); Microna® Matte Red (INCI: Iron Oxide; Mica); Cosmetic white C47056 (INCI: Titanium Dioxide, Mica); FDC Yellow 6 Al Lake C705270 (INCI: Colour Index 15985); DC Red 7 Ca Lake C19003 (INCI: Colour Index 15850); Irodin 100 Silverpearl (INCI: Mica, Titanium dioxide); Colophane Claire type Y (INCI: Colophonium); Mexoryl®XL: 2-(2H-Benzotriazol-2-yl)-4-methyl-6-(2-methyl-3-(1,3,3,3-tetramethyl-1-(trimethylsilyloxy)-disiloxanyl)propyl)phenol, INCI: Drometrizole trisiloxane; Monomuls® 90-0 18, INCI: Glyceryl Oleate, Cognis GmbH; Monomuls® 90 L 12, INCI: Glyceryl Laurate, Cognis GmbH; Myrj® 51, INCI: PEG-30-Stearate, Uniqema; Myritol® 312, INCI: Caprylic/Capric Triglyceride, Cognis GmbH; Myritol®331, INCI: Cocoglycerides, Cognis GmbH; Myritol®PC, INCI: Propylene Glycol Dicaprylate/Dicaprate, Cognis GmbH; Neo Heliopan® 303, INCI: Octocrylene, Symrise; Neo Heliopan AP, INCI: Disodium Phenyl Dibenzimidazole Tetrasulfonate, Symrise; Neo Heliopan AV, INCI: Ethylhexyl Methoxycinnamate, Symrise; Neo Heliopan® BB, INCI: Benzophenone-3, Symrise; Neo Heliopan® E 1000, INCI: Isoamyl-p-Methoxycinnamate, Symrise; Neo Heliopan®Hydro, INCI: Phenylbenzimidazole Sulfonic Acid, Symrise; Neo Heliopan® HMS INCI: Homosalate; Neo Heliopan® MBC, INCI: 4-Methylbenzylidene Camphor, Symrise; Neo Heliopan® OS, INCI: Ethylhexyl Salicylate, Symrise; Novata® AB, INCI: Cocoglycerides, Cognis GmbH; Parsol® 1789, INCI: Butyl Methoxydibenzoylmethane, Hoffmann-La Roche (Givaudan); Phenonip® XB: INCI: Phenoxyethanol and Methylparaben and Propylparaben and Ethylparaben; Pemulen® TR-2 Polymer, INCI: Acrylates/C10-30 Alkylacrylate Crosspolymer, Noveon, Inc.; Photonyl®LS, INCI: Arginine, Disodium Adenosine Triphosphate, Mannitol, Pyridoxine HCL, Phenylalanine, Tyrosine, Laboratoires Serobiologiques (Cognis); Prisorine® 3505, INCI: Isostearic Acid, Uniqema; Prisorine® 3758, INCI: Hydrogenated Polyisobutene, Uniqema; Rezal 36G, INCI: Aluminum Zirconium Tetrachlorohydrex GLY, Reheis, Inc.; Rheocare® C Plus, INCI: Carbomer, Cognis GmbH; Rheocare® TTN, INCI: Acrylates Copolymer, Cognis GmbH; Ronasphere® LDP (INCI: Silica, Titaniumdioxide, Iron Oxides); Squatol® S, INCI: Hydrogenated Polyisobutene, BASF Corp.; Poloxamer® 101, INCI: Poloxamer, BASF SE; SFE®839, INCI: Cyclopentasiloxane and Dimethicone/Vinyl Dimethicone Crosspolymer, GE Silicones; Wacker AK®350 silicone oil, INCI: Dimethicone, Wacker; Tego®Care 450, INCI: Polyglyceryl-3 Methylglucose Distearate, Goldschmidt; Tego®Care CG 90, INCI: Cetearyl Glucoside, Goldschmidt; Tegosoft® DEC, INCI: Diethylhexyl Carbonate, Goldschmidt; Tinosorb® S, INCI: Bis-Ethylhexyloxyphenol Methoxyphenyl Triazine, Ciba Specialty Chemicals Corporation; Tinosorb® M, INCI: Methylene Bis-Benzotriazolyl Tetramethylbutylphenol, Ciba Specialty Chemicals Corporation; Tween® 60, INCI: Polysorbate 60, Uniqema (ICI Surfactants); Uvasorb® HEB, INCI: Diethylhexyl Butamido Triazone, 3V Inc.; Ultragel® 300, INCI: Polyquaternium-37; Unirep® U-18, INCI: Dimethyl Phthalate and Diethyl Toluamide and Ethyl Hexanediol, Induchem AG; Uvinul® T 150, INCI: Ethylhexyl Triazone, BASF; Uvinul® A plus, INCI: Diethylamino Hydroxybenzoyl Hexyl Benzoate, BASF; Veegum® Ultra, INCI: Magnesium Aluminium Silicate, R. T. Vanderbilt Company, Inc.; Veegum® Plus, INCI: Magnesium Aluminum Silicate and Cellulose Gum, R. T. Vanderbilt Company, Inc.; Z-Cote® HP 1, INCI: Zinc Oxide and Triethoxy-caprylylsilane, BASF; Zinc Oxide NDM, INCI: Zinc Oxide, Symrise.

The invention claimed is:
1. A powder composition consisting of:
a) at least 70% by weight of a mixture of alkyl sulfosuccinate monoesters, the mixture consisting of C16- and C18-alkyl sulfosuccinate monoesters of the general formula (I) and/or (II), based on the total alkyl sulfosuccinate monoesters of formula (I) and (II):

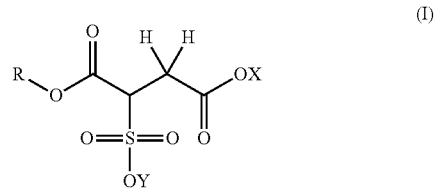

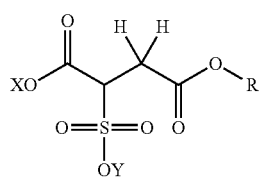
(II)

wherein R is a linear C16 or C18 alkyl radical, and X and Y are each independently a hydrogen atom or a cation capable of forming a water soluble salt selected from the group consisting of alkali metal, ammonium and organic ammonium; and b) 0-30% by weight of secondary constituents selected from the group consisting of unconverted reactants from esterification and by-products of esterification, wherein unconverted fatty alcohols from esterification are present in an amount less than or equal to 5% by weight, based on the total amount of alkyl sulfosuccinate monoester; and C16-alkyl sulfosuccinate monoesters and C18-alkyl sulfosuccinate monoesters are each present in the mixture in an amount of 45-55% by weight, based on the total amount of C16- and C18-alkyl sulfosuccinate monoester.

2. The powder composition according to claim 1, wherein X and Y are each independently selected from the group consisting of Na, K, and $NH_4$.

3. The powder composition according to claim 2, wherein X and Y are identical.

4. The powder composition according to claim 3, wherein X and Y are each Na.

5. The powder composition according to claim 1, wherein the unconverted reactants from esterification include maleic anhydride.

6. The powder composition according to claim 1, wherein the by-products of esterification include diesters.

7. The powder composition according to claim 1, wherein C16- and C18-alkyl sulfosuccinate monoesters are at least 80% by weight.

8. The powder composition according to claim 1 which is produced by reaction of maleic anhydride with a fatty alcohol mixture.

9. The powder composition according to claim 1 which is produced by mixing C16- and C18-alkyl sulfosuccinate monoesters.

10. A method of producing a cosmetic and/or pharmaceutical formulation, the method comprising incorporating the powder composition according to claim 1 into the cosmetic and/or pharmaceutical formulation.

11. A method of dispersing UV photoprotective filters in a cosmetic and/or pharmaceutical formulation, the method comprising incorporating the powder composition according to claim 1 and a UV photoprotective filter as into the cosmetic and/or pharmaceutical formulation.

* * * * *